United States Patent
Kielian et al.

(10) Patent No.: US 10,876,134 B2
(45) Date of Patent: Dec. 29, 2020

(54) GENE THERAPY FOR JUVENILE BATTEN DISEASE

(71) Applicants: BOARD OF REGENTS OF THE UNIVERSITY OF NEBRASKA, Lincoln, NE (US); OHIO STATE INNOVATION FOUNDATION, Columbus, OH (US)

(72) Inventors: Tammy Kielian, La Vista, NE (US); Kevin Foust, New Albany, OH (US)

(73) Assignees: BOARD OF REGENTS OF THE UNIVERSITY OF NEBRASKA, Lincoln, NE (US); OHIO STATE INNOVATION FOUNDATION, Columbus, OH (US)

(*) Notice: Subject to any disclaimer, the term of this patent is extended or adjusted under 35 U.S.C. 154(b) by 0 days.

(21) Appl. No.: 15/537,384

(22) PCT Filed: Dec. 16, 2015

(86) PCT No.: PCT/US2015/066206
§ 371 (c)(1),
(2) Date: Jun. 16, 2017

(87) PCT Pub. No.: WO2016/100575
PCT Pub. Date: Jun. 23, 2016

(65) Prior Publication Data
US 2019/0032078 A1    Jan. 31, 2019

Related U.S. Application Data

(60) Provisional application No. 62/092,501, filed on Dec. 16, 2014, provisional application No. 62/146,793, filed on Apr. 13, 2015.

(51) Int. Cl.
| | | |
|---|---|---|
| *A61K 48/00* | (2006.01) | |
| *C12N 15/864* | (2006.01) | |
| *C12N 15/86* | (2006.01) | |
| *A61P 25/00* | (2006.01) | |

(52) U.S. Cl.
CPC .......... *C12N 15/8645* (2013.01); *A61K 48/00* (2013.01); *A61P 25/00* (2018.01); *C12N 15/86* (2013.01); *C12N 2750/14143* (2013.01); *C12N 2750/14171* (2013.01); *C12N 2830/008* (2013.01)

(58) Field of Classification Search
USPC ........................................................ 424/93.2
See application file for complete search history.

(56) References Cited

U.S. PATENT DOCUMENTS

| | | | |
|---|---|---|---|
| 6,582,692 B1 | 6/2003 | Podsakoff et al. | |
| 7,906,111 B2 | 3/2011 | Wilson et al. | |
| 9,926,574 B2 | 3/2018 | Barkats | |
| 10,208,318 B2 | 2/2019 | Barkats | |
| 10,301,648 B2 | 5/2019 | Vandenberghe et al. | |
| 10,738,326 B2 | 8/2020 | Muramatsu | |
| 2003/0083299 A1 | 5/2003 | Ferguson | |
| 2005/0014262 A1 | 1/2005 | Gao et al. | |
| 2007/0036760 A1 | 2/2007 | Wilson et al. | |
| 2009/0202490 A1 | 8/2009 | Schaffer et al. | |
| 2010/0240739 A1 | 9/2010 | Barkats | |
| 2012/0177605 A1 | 7/2012 | Kaspar et al. | |
| 2013/0039888 A1 | 2/2013 | McCarty et al. | |
| 2013/0158104 A1 | 6/2013 | Tubert et al. | |
| 2013/0225666 A1* | 8/2013 | Kaspar ............... A61K 48/0075 514/44 R |
| 2013/0296532 A1 | 11/2013 | Hermens et al. | |
| 2015/0079038 A1* | 3/2015 | Deverman ......... C12N 15/1068 424/93.2 |
| 2015/0104863 A1 | 4/2015 | Bosch Tubert et al. | |
| 2017/0166926 A1* | 6/2017 | Deverman ............. A61K 38/43 |

FOREIGN PATENT DOCUMENTS

| | | | |
|---|---|---|---|
| EP | 1 620 133 A1 | | 2/2006 |
| WO | WO-97/08308 A1 | | 3/1997 |
| WO | WO 97/08308 | * | 8/1997 |
| WO | WO-2005/033321 A2 | | 4/2005 |
| WO | WO-2007/089632 A2 | | 8/2007 |
| WO | WO-2009/137006 A3 | | 11/2009 |
| WO | WO-2011/133890 A1 | | 10/2011 |
| WO | WO-2014/052789 A1 | | 4/2014 |

OTHER PUBLICATIONS

Edelstein (Journal Gene Med., 2004, vol. 6, p. 597-602).*
Wu (Mol. Therapy, 2008, vol. 16, No. 2, p. 280-289).*
Lu (Human Gene Therapy, Jun. 2008, vol. 19, No. 6, p. 648-654).*
Ishiwata (J. Gene Med., 2009, vol. 11, p. 1020-1029).*
McIntosh (Blood Apr. 2013, vol. 121, No. 17, p. 3335-3344.*
Rogers (Front Biosci., 2015, vol. 20, p. 556-603).*
Carter (Human Gene Therapy, 2005, vol. 16, p. 541-550).*
Crystal ("Administration of a replication-deficient adeno-associated virus gene transfer vector expressing the human CLN2 cDNA to the brain of children with late infantile neuronal ceroid lipofuscinosis" Hum. Gene Ther. 2004, vol. 15, 1131-1154).*
Cabrera-Salazar (Am. Soc. Gene Therapy, 2007, vol. 15, No. 10, p. 1782-1788).*
Garg (J. Neurosci., Aug. 21, 2013, vol. 33, No. 34, p. 13612-13620).*
Dyke (American J. Neuroradiol., 2013, vol. 34, p. 884-889).*
Schuster (Frontiers in Neuroanatomy, Jun. 2014, vol. 8, Article 42, p. 1-14).*
Wiley ("Genome editing and gene replacement: towards the treatment of Batten disease." IOVS, (Jun. 2015) vol. 56, No. 7, pp. 3593).*

(Continued)

*Primary Examiner* — Michael C Wilson
(74) *Attorney, Agent, or Firm* — Foley & Lardner LLP

(57) ABSTRACT

Compositions and methods for the treatment of Juvenile Neuronal Ceroid Lipofuscinosis (JNCL), also known as Juvenile Batten Disease, are provided herein. In certain embodiments the compositions include but are not limited to *adeno-associated viral* (AAV) constructs, including self-complementary adeno-associated viral (sc-AAV) constructs, that express the human gene CLN3 (or a CLN3 cDNA).

27 Claims, 34 Drawing Sheets

Specification includes a Sequence Listing.

(56) References Cited

OTHER PUBLICATIONS

Bosch (J. Neurosci., Sep. 2016, vol. 36, No. 37, p. 9669-9682).*
Flotte (J. Biol. Chem., 1993, vol. 268, No. 5, p. 3781-3790).*
Sondhi (Human Gene Therapy, Mar. 2014, vol. 25, p. 223-239).*
Lanoix (EMBO, 1988, vol. 7, No. 8, p. 2515-2522).*
Choi (Mol. Brain 2014, vol. 7, No. 7, p. 1-10).*
Sanders (Society of Neurosci. Abstract Viewer and Itinerary Planner, 2003, Abstract 335.8).*
Fu, H. et al. (2011) "Correction of Neurological Disease of Mucopolysaccharidosis IIIB in Adult Mice by rAAV9 Trans-Blood-Brain Barrier Gene Delivery," Molecular Therapy 19(6):1025-1033.
Gray, S.J. et al. (2011) "Preclinical Differences of Intravascular AAV9 Delivery to Neurons and Glia: A Comparative Study of Adult Mice and Nonhuman Primates," Molecular Therapy 19(6):1058-1069.
Griffey, M.A. et al. (2006) "CNS-Directed AAV2-Mediated Gene Therapy Ameliorates Functional Deficits in a Murine Model of Infantile Neuronal Ceroid Lipofuscinosis," Molecular Therapy 13(3):538-547.
Kielian, T. et al. (2016) "Adeno-associated virus 9 gene therapy for juvenile neuronal ceroid lipofuscinosis," Molecular Genetics and Metabolism 117(2):Abstract 161.
Sondhi, D. et al. (2012) "Long-Term Expression and Safety of Administration of AAVrh.10hCLN2 to the Brain of Rats and Nonhuman Primates for the Treatment of Late Infantile Neuronal Ceroid Lipfuscinosis," Human Gene Therapy Methods 23(5):324-335.
Worgall, S. et al. (2008) "Treatment of Late Infantile Neuronal Ceroid Lipofuscinosis by CNS Administration of a Serotype 2 Adeno-Associated Virus Expressing CLN2 cDNA," Human Gene Therapy 19(5):463-474.
International Search Report and Written Opinion (ISA/EP) in International Application No. PCT/US2015/066206, dated May 27, 2016.
Adachi et al., "A segment of the Mecp2 promoter is sufficient to drive expression in neurons", Human Molecular Genetics, 2005, vol. 14, No. 23, pp. 3709-3722.
Ballas et al., "Non-cell autonomous influence of MeCP2-deficient glia on neuronal dendritic morphology", Nat Neurosci., Mar. 2009, 12(3), pp. 311-317.
Foust et al., "Rescue of the spinal muscular atrophy phenotype in a mouse model by early postnatal delivery of SMN", Nat Biotechno., Mar. 2010, 28(3), pp. 271-274.
Garg et al., "Systemic Delivery of MeCP2 Recues Behavioral and Cellular Deficits in Female Mouse Models of Rett Syndrome", the Journal of Neuroscience, Aug. 21, 2013, 33(34), pp. 13612-13620.
McCarty et al., "Adeno-associated virus terminal repeat (TR) mutant generates self-complementary vectors to overcome the rate-limiting step to transduction in vivo", Gene Therapy, 2003, 10(26), pp. 2112-2118.
McCarty et al., "Self-complementary recombinant adeno-associated virus (scAAV) vectors promote efficient transduction independently of DNA synthesis", Gene Therapy, 2001, 8(16), pp. 1248-1254.
Skene et al., "Neuronal MeCP2 is expressed at near histone-octamer levels and globally alters the chromatin state", Mol Cell., Feb. 26, 2010, 37(4), pp. 457-468.

Storek et al., "Sensory neuron targeting by self-complementary AAV8 via lumbar puncture for chronic pain", PNAS, Jan. 22, 2008, vol. 105, No. 3, pp. 1055-1060.
Towne et al., "Recombinant adeno-associated virus serotype 6 (rAAV2/6)-mediated gene transfer to nociceptive neurons through different routes of delivery", Molecular Pain, 2009, 5:52, pp. 1-17.
Xiao et al., "Gene Therapy Vectors Based on Adeno-Associated Virus Type 1", Journal of Virology, vol. 73, No. 5, May 1999, pp. 3994-4003.
Snyder et al., "Comparison of Adeno-Associated Viral Vector Serotypes for Spinal Cord and Motor Neuron Gene Delivery", Human Gene Therapy, Sep. 2011, 22, pp. 1129-1135.
Fu et al., "Self-Complementary Adeno-associated Virus Serotype 2 Vector: Global Distribution and Broad Dispersion of AAV-Mediated Transgene Expression in Mouse Brain", Molecular Therapy, vol. 8, No. 6, Dec. 2003, pp. 911-917.
Zhang et al., "Several rAAV Vectors Efficiently Cross the Blood-brain Barrier and Transduce Neurons and Astrocytes in the Neonatal Mouse Central Nervous System", the American Society of Gene and Cell Therapy, vol. 19, No. 8, Aug. 2011, pp. 1440-1448.
Sondhi et al., "Partial Correction of the CNS Lysosomal Storage Defect in a Mouse Model of Juvenile Neuronal Ceroid Lipofuscinosis by Neonatal CNS Administration of an Adeno-Associated Virus Serotype rh.10 Vector Expressing the Human CLN3 Gene", Human Gene Therapy, Mar. 2014, vol. 25, pp. 223-239.
Gray et al., "Directed evolution of a novel adeno-associated virus (AAV) vector that crosses the seizure-comprised blood-brain barrier (BBB)", Mol. Ther., vol. 18, No. 3, Mar. 2010, 570-578.
Gray et al., "Gene Therapy and neurodevelopmental disorders", Neuropharmacology, vol. 68, Jun. 13, 2012, pp. 136-142.
Hutson et al., "Corticospinal tract transduction: a comparison of seven adenoassociated viral vector serotypes and a non-integrating lentiviral vector", Gene Therapy, vol. 19, No. 1, May 12, 2011, pp. 49-60.
Koerber et al., "Molecular Evolution of Adeno-associated Virus for Enhanced Glial Gene Delivery", Molecular Therapy: The Journal of the American Society of Gene Therapy, vol. 17, No. 12, Dec. 2009, pp. 2088-2095.
Maguire et al., "Directed evolution of adeno-associated virus for glioma cell transduction", Journal of Neuro-Oncology, vol. 96, No. 3, Jul. 19, 2009, pp. 337-347.
Manfredsson et al., "AAV9: a potential blood-brain barrier buster," Molecular Therapy, vol. 17, No. 3, 2009 pp. 403-405.
Perabo et al., "Combinatorial engineering of a gene therapy vector: directed evolution of adeno-associated virus", The journal of gene medicine, vol. 8, Nov. 14, 2005, pp. 155-162.
Powell et al., "Characterization of a novel adeno-associated viral vector with preferential oligodendrocyte tropism", Gene Therapy, vol. 23, No. 11, Sep. 15, 2016, pp. 807-814.
Wu et al., "Single amino acid changes can influence titer, heparin binding, and tissue tropism in different adeno-associated virus serotypes", Journal of Virology, vol. 80, No. 22, Aug. 22, 2006, pp. 11393-11397.
Yang et al., "Global CN Transduction of Adult Mice by Intravenously Delivered rAAVrh.8 and rAAVrh.10 and Nonhuman Primates by rAAVrh.10", Molecular Therapy: The Journal of the American Society of Gene Therapy, vol. 22, No. 7, Jul. 2014, pp. 1299-1309.

* cited by examiner scAAV9/β-actin-hCLN3 scAAV9/MeCP2-hCLN3 scAAV9/β-actin-GFP scAAV9/MeCP2-GFP

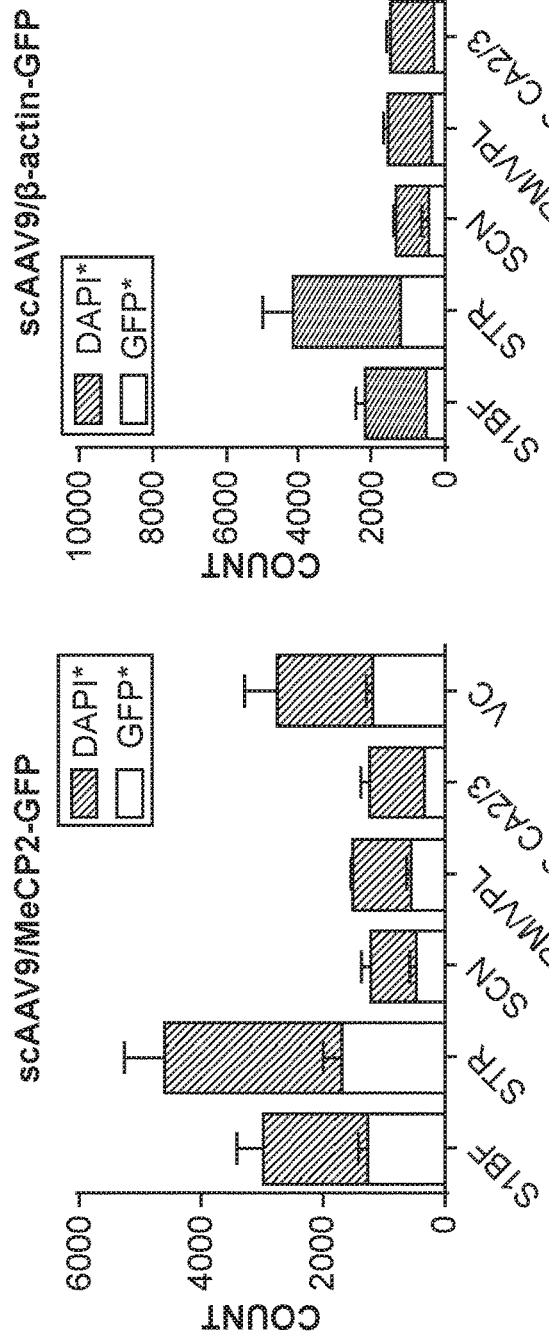
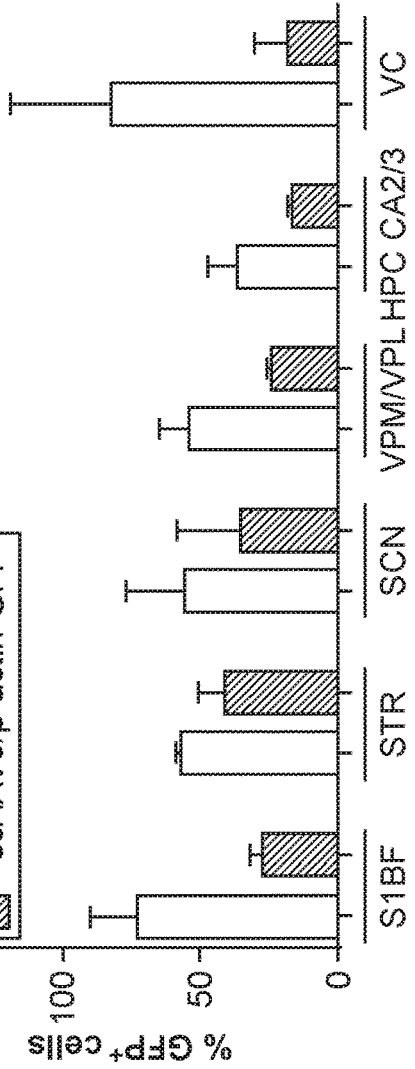
FIG. 6A
FIG. 6B

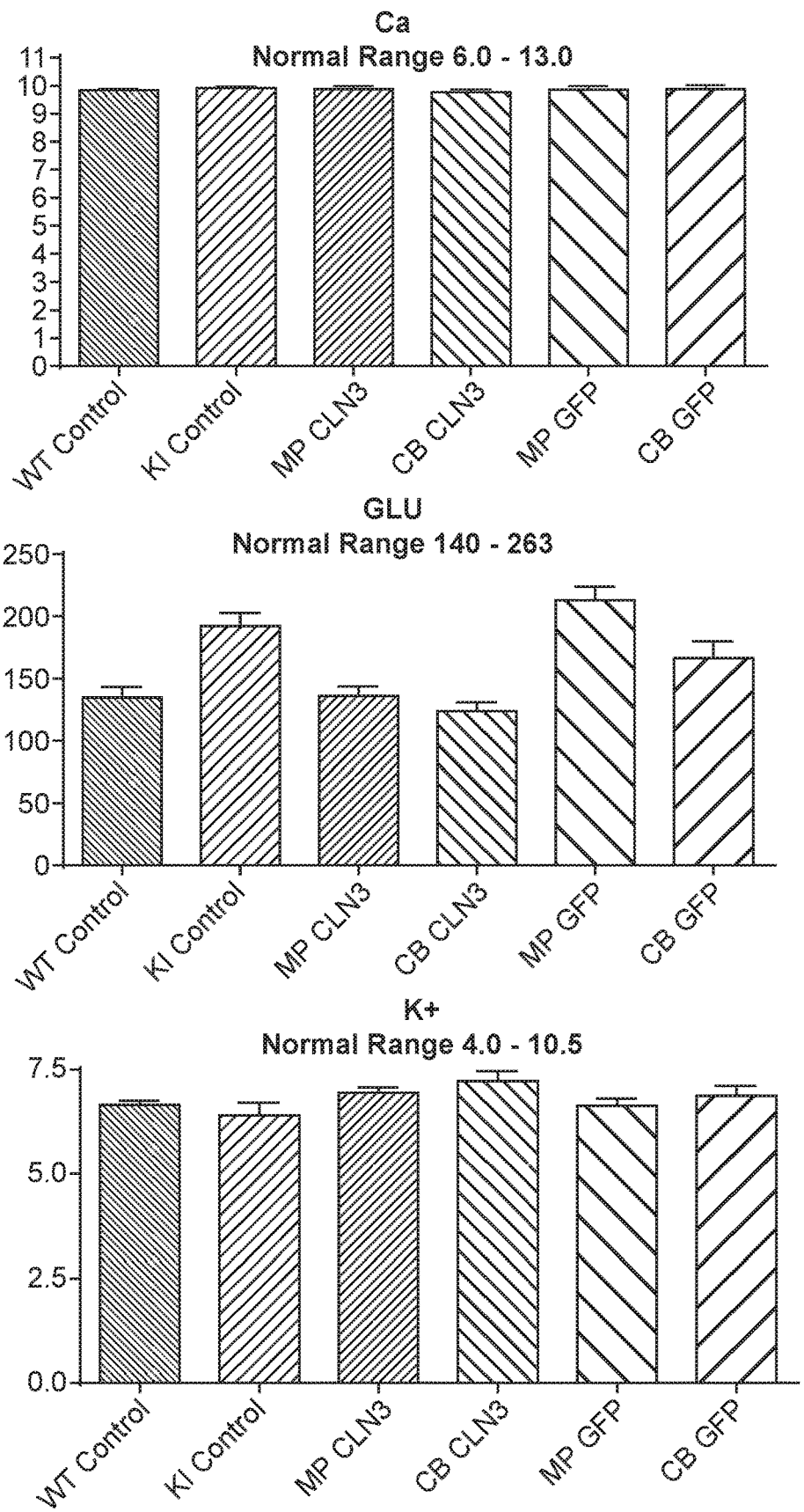
FIG. 12 (Cont. 1)

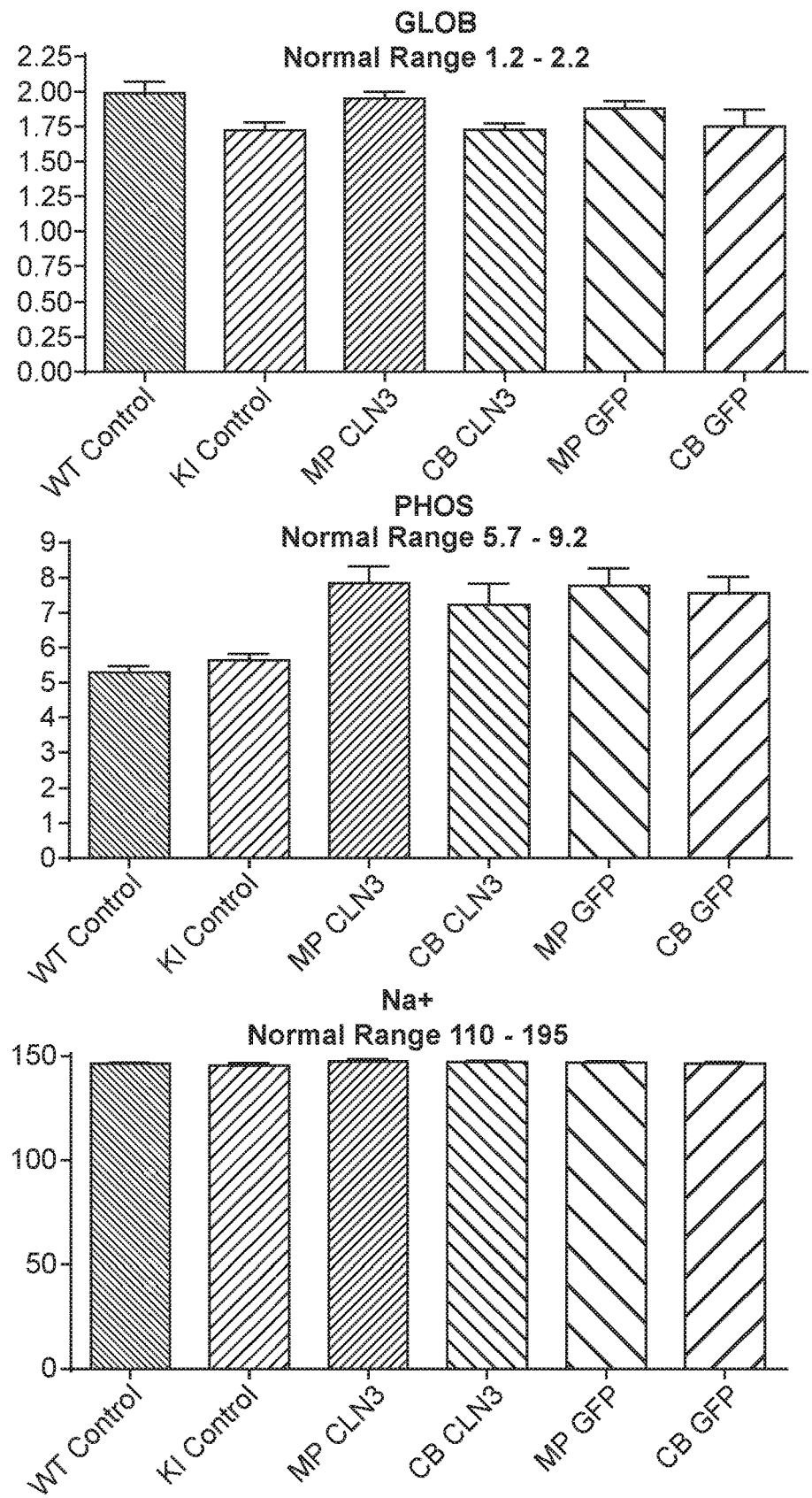
FIG. 12 (Cont. 2)

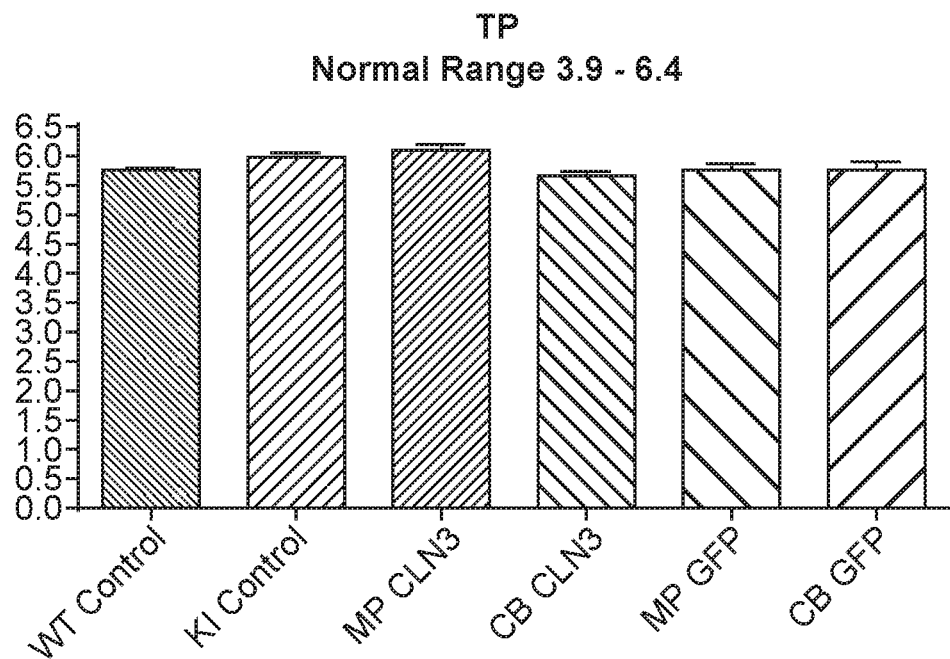
FIG. 12 (Cont. 3)

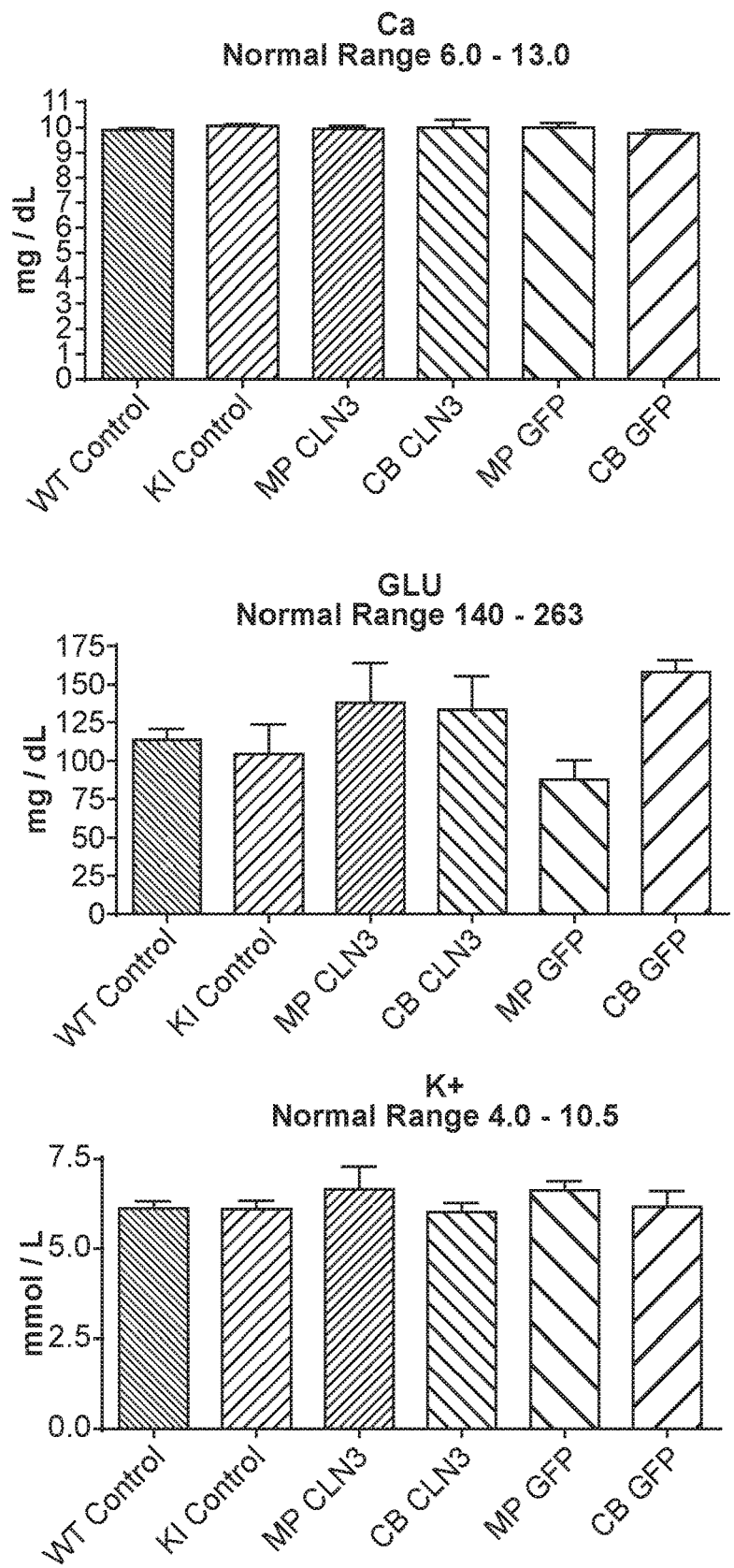
FIG. 13 (Cont. 1)

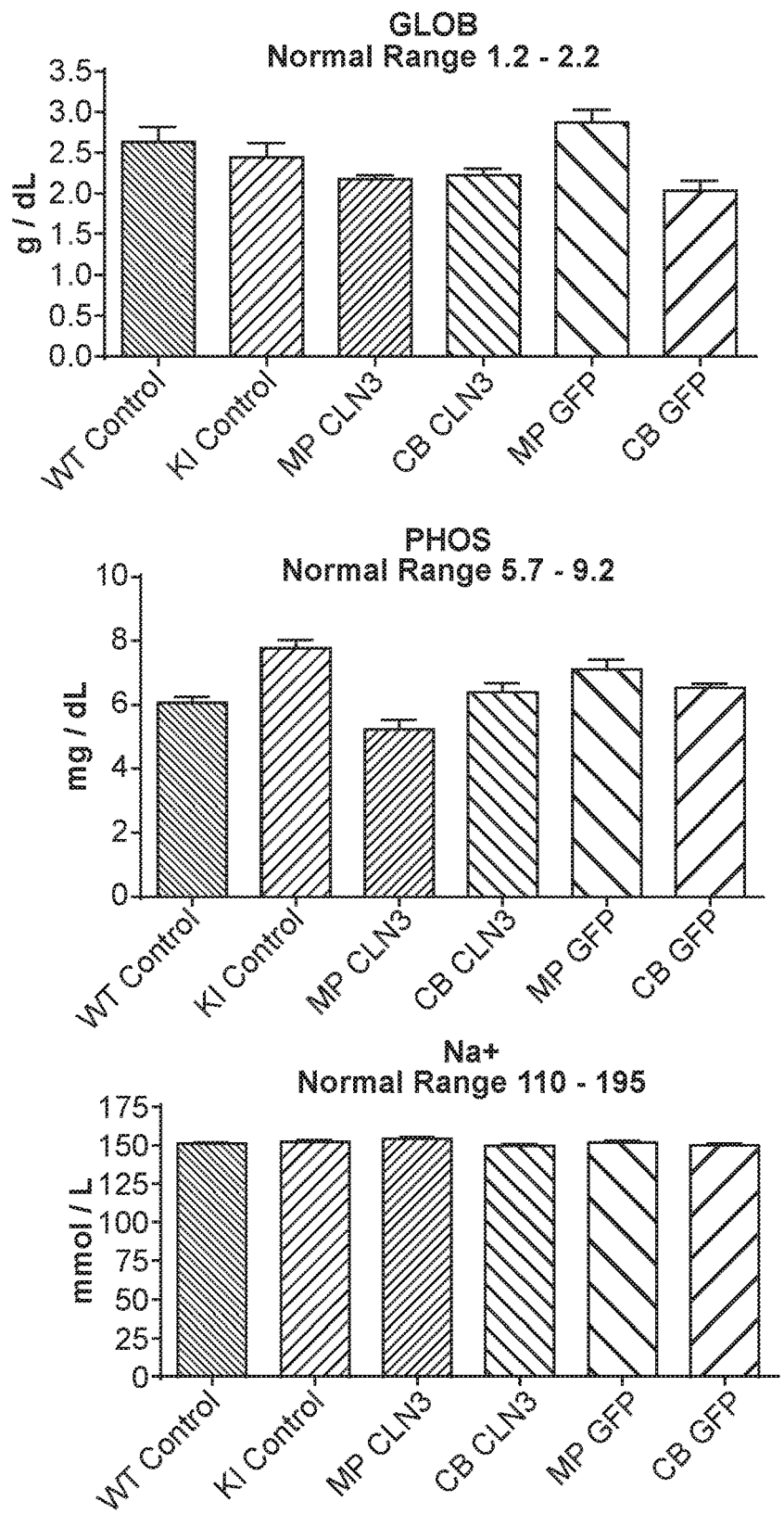
FIG. 13 (Cont. 2)

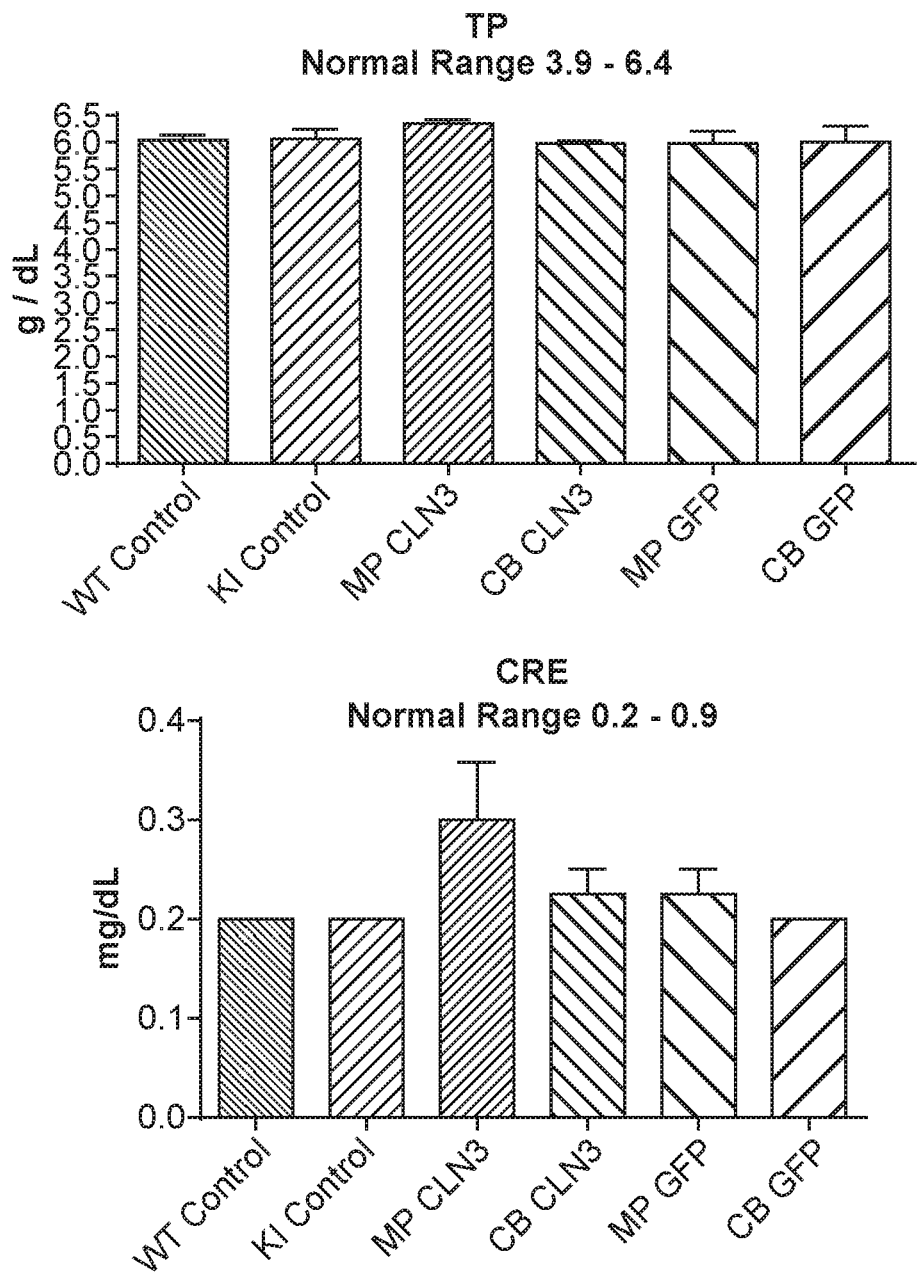
FIG. 13 (Cont. 3)

SEQUENCE LISTING

<160> NUMBER OF SEQ ID NOS: 38

<210> SEQ ID NO 1
<211> LENGTH: 438
<212> TYPE: PRT
<213> ORGANISM: Homo sapiens

<400> SEQUENCE: 1

Met Gly Gly Cys Ala Gly Ser Arg Arg Arg Phe Ser Asp Ser Glu Gly
1               5                   10                  15

Glu Glu Thr Val Pro Glu Pro Arg Leu Pro Leu Leu Asp His Gln Gly
            20                  25                  30

Ala His Trp Lys Asn Ala Val Gly Phe Trp Leu Leu Gly Leu Cys Asn
        35                  40                  45

```
Asn Phe Ser Tyr Val Val Met Leu Ser Ala Ala His Asp Ile Leu Ser
 50                  55                  60

His Lys Arg Thr Ser Gly Asn Gln Ser His Val Asp Pro Gly Pro Thr
 65                  70                  75                  80

Pro Ile Pro His Asn Ser Ser Ser Arg Phe Asp Cys Asn Ser Val Ser
                 85                  90                  95

Thr Ala Ala Val Leu Leu Ala Asp Ile Leu Pro Thr Leu Val Ile Lys
            100                 105                 110

Leu Leu Ala Pro Leu Gly Leu His Leu Leu Pro Tyr Ser Pro Arg Val
            115                 120                 125

Leu Val Ser Gly Ile Cys Ala Ala Gly Ser Phe Val Leu Val Ala Phe
130                 135                 140

Ser His Ser Val Gly Thr Ser Leu Cys Gly Val Val Phe Ala Ser Ile
145                 150                 155                 160

Ser Ser Gly Leu Gly Glu Val Thr Phe Leu Ser Leu Thr Ala Phe Tyr
                165                 170                 175

Pro Arg Ala Val Ile Ser Trp Trp Ser Ser Thr Gly Gly Ala Gly
            180                 185                 190

Leu Leu Gly Ala Leu Ser Tyr Leu Gly Leu Thr Gln Ala Gly Leu Ser
            195                 200                 205

Pro Gln Gln Thr Leu Leu Ser Met Leu Gly Ile Pro Ala Leu Leu Leu
210                 215                 220

Ala Ser Tyr Phe Leu Leu Leu Thr Ser Pro Glu Ala Gln Asp Pro Gly
225                 230                 235                 240

Gly Glu Glu Glu Ala Glu Ser Ala Ala Arg Gln Pro Leu Ile Arg Thr
                245                 250                 255

Glu Ala Pro Glu Ser Lys Pro Gly Ser Ser Ser Leu Ser Leu Arg
            260                 265                 270

Glu Arg Trp Thr Val Phe Lys Gly Leu Leu Trp Tyr Ile Val Pro Leu
            275                 280                 285

Val Val Val Tyr Phe Ala Glu Tyr Phe Ile Asn Gln Gly Leu Phe Glu
290                 295                 300

Leu Leu Phe Phe Trp Asn Thr Ser Leu Ser His Ala Gln Gln Tyr Arg
305                 310                 315                 320

Trp Tyr Gln Met Leu Tyr Gln Ala Gly Val Phe Ala Ser Arg Ser Ser
                325                 330                 335

Leu Arg Cys Cys Arg Ile Arg Phe Thr Trp Ala Leu Ala Leu Leu Gln
            340                 345                 350

Cys Leu Asn Leu Val Phe Leu Leu Ala Asp Val Trp Phe Gly Phe Leu
            355                 360                 365

Pro Ser Ile Tyr Leu Val Phe Leu Ile Ile Leu Tyr Glu Gly Leu Leu
370                 375                 380

Gly Gly Ala Ala Tyr Val Asn Thr Phe His Asn Ile Ala Leu Glu Thr
385                 390                 395                 400

Ser Asp Glu His Arg Glu Phe Ala Met Ala Thr Cys Ile Ser Asp
                405                 410                 415

Thr Leu Gly Ile Ser Leu Ser Gly Leu Leu Ala Leu Pro Leu His Asp
            420                 425                 430

Phe Leu Cys Gln Leu Ser
            435

<210> SEQ ID NO 2
<211> LENGTH: 6055
<212> TYPE: DNA
```

```
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (662)..(767)
<223> OTHER INFORMATION: Mutated ITR
<220> FEATURE:
<221> NAME/KEY: misc_feature
<222> LOCATION: (775)..(1511)
<223> OTHER INFORMATION: Promoter
<220> FEATURE:
<221> NAME/KEY: misc_feature
<222> LOCATION: (1520)..(1550)
<223> OTHER INFORMATION: SV40 late 19s insert
<220> FEATURE:
<221> NAME/KEY: misc_feature
<222> LOCATION: (1520)..(1616)
<223> OTHER INFORMATION: modSV40 late 16s insert
<220> FEATURE:
<221> NAME/KEY: misc_feature
<222> LOCATION: (1589)..(1610)
<223> OTHER INFORMATION: Seq primer
<220> FEATURE:
<221> NAME/KEY: CDS
<222> LOCATION: (1683)..(2999)
<223> OTHER INFORMATION: CLN3
<220> FEATURE:
<221> NAME/KEY: misc_feature
<222> LOCATION: (3052)..(3198)
<223> OTHER INFORMATION: BGHpA
<220> FEATURE:
<221> NAME/KEY: misc_feature
<222> LOCATION: (3278)..(3418)
<223> OTHER INFORMATION: ITR

<400> SEQUENCE: 2
gcccaatacg caaaccgcct ctccccgcgc gttggccgat tcattaatgc agctgattct      60
aacgaggaaa gcacgttata cgtgctcgtc aaagcaacca tagtacgcgc cctgtagcgg     120
cgcattaagc gcggcgggtg tggtggttac gcgcagcgtg accgctacac ttgccagcgc     180
cctagcgccc gctcctttcg ctttcttccc ttcctttctc gccacgttcg ccggctttcc     240
ccgtcaagct ctaaatcggg ggctcccttt agggttccga tttagtgctt tacggcacct     300
cgaccccaaa aaacttgatt agggtgatgg ttcacgtagt gggccatcgc cctgatagac     360
ggtttttcgc cctttgacgt tggagtccac gttctttaat agtggactct tgttccaaac     420
tggaacaaca ctcaacccta tctcggtcta ttcttttgat ttataaggga ttttgccgat     480
ttcggcctat tggttaaaaa atgagctgat ttaacaaaaa tttaacgcga attttaacaa     540
aatattaacg cttacaattt aaatatttgc ttatacaatc ttcctgtttt tggggctttt     600
ctgattatca accggggtac atatgattga catgctagtt ttacgattac cgttcatcgc     660
cctgcgcgct cgctcgctca ctgaggccgc ccgggcaaag cccggcgtc gggcgacctt     720 tggtcgcccg gcctcagtga gcgagcgagc gcgcagagag ggagtggaat tctatcaaac     780
catctgattc aacaatgaca daccgatctc ttatgggctt ggcacacacc atctgcccat     840
tataaacgtc tgcaaagacc aaggtttgat atgttgattt tactgtcagc cttaagagtg     900
cgacatctgc taatttagtg taataataca atcagtagac cctttaaaac aagtcccttg     960
gcttggaaca acgccaggct cctcaacagg caactttgct acttctacag aaaatgataa    1020
taaagaaatg ctggtgaagt caaatgctta tcacaatggt gaactactca gcagggaggc    1080
tctaataggc gccaagagcc tagacttcct taagcgccag agtccacaag ggcccagtta    1140
atcctcaaca ttcaaatgct gcccacaaaa ccagcccctg tgtgccctag ccgcctcttt    1200
```

-continued

```
tttccaagtg acagtagaac tccaccaatc cgcagctgaa tggggtccgc ctcttttccc      1260
tgcctaaaca gacaggaact cctgccaatt gagggcgtca ccgctaaggc tccgccccag      1320
cctgggctcc acaaccaatg aagggtaatc tcgacaaaga gcaaggggtg gggcgcgggc      1380
gcgcaggtgc agcagcacac aggctggtcg ggagggcggg gcgcgacgtc tgccgtgcgg      1440
ggtcccggca tcggttgcgc gcgcgctccc tcctctcgga gagagggctg tggtaaaacc      1500
cgtccggaaa agttaactgg taagtttagt cttttttgtct tttatttcag gtcccggatc      1560
cggtggtggt gcaaatcaaa gaactgctcc tcagtggatg ttgcctttac ttctaggcct      1620
gtacggaagt gttacttctg ctctaaaagc tgcggaattg tacccgcggc cgatccaccg      1680 gt atg gga ggc tgt gca ggc tcg cgg cgg cgc ttt tcg gat tcc gag         1727
   Met Gly Gly Cys Ala Gly Ser Arg Arg Arg Phe Ser Asp Ser Glu
   1               5                   10                  15 ggg gag gag acc gtc ccg gag ccc cgg ctc cct ctg ttg gac cat cag        1775
Gly Glu Glu Thr Val Pro Glu Pro Arg Leu Pro Leu Leu Asp His Gln
                20                  25                  30 ggc gcg cat tgg aag aac gcg gtg ggc ttc tgg ctg ctg ggc ctt tgc        1823
Gly Ala His Trp Lys Asn Ala Val Gly Phe Trp Leu Leu Gly Leu Cys
            35                  40                  45 aac aac ttc tct tat gtg gtg atg ctg agt gcc gcc cac gac atc ctt        1871
Asn Asn Phe Ser Tyr Val Val Met Leu Ser Ala Ala His Asp Ile Leu
        50                  55                  60 agc cac aag agg aca tcg gga aac cag agc cat gtg gac cca ggc cca        1919
Ser His Lys Arg Thr Ser Gly Asn Gln Ser His Val Asp Pro Gly Pro
    65                  70                  75 acg ccg atc ccc cac aac agc tca tca cga ttt gac tgc aac tct gtc        1967
Thr Pro Ile Pro His Asn Ser Ser Ser Arg Phe Asp Cys Asn Ser Val
80                  85                  90                  95 tct acg gct gct gtg ctc ctg gcg gac atc ctc ccc aca ctc gtc atc        2015
Ser Thr Ala Ala Val Leu Leu Ala Asp Ile Leu Pro Thr Leu Val Ile
                100                 105                 110 aaa ttg ttg gct cct ctt ggc ctt cac ctg ctg ccc tac agc ccc cgg        2063
Lys Leu Leu Ala Pro Leu Gly Leu His Leu Leu Pro Tyr Ser Pro Arg
            115                 120                 125 gtt ctc gtc agt ggg att tgt gct gct gga agc ttc gtc ctg gtt gcc        2111
Val Leu Val Ser Gly Ile Cys Ala Ala Gly Ser Phe Val Leu Val Ala
        130                 135                 140 ttt tct cat tct gtg ggg acc agc ctg tgt ggt gtg gtc ttc gct agc        2159
Phe Ser His Ser Val Gly Thr Ser Leu Cys Gly Val Val Phe Ala Ser
    145                 150                 155 atc tca tca ggc ctt ggg gag gtc acc ttc ctc tcc ctc act gcc ttc        2207
Ile Ser Ser Gly Leu Gly Glu Val Thr Phe Leu Ser Leu Thr Ala Phe
160                 165                 170                 175 tac ccc agg gcc gtg atc tcc tgg tgg tcc tca ggg act ggg gga gct        2255
Tyr Pro Arg Ala Val Ile Ser Trp Trp Ser Ser Gly Thr Gly Gly Ala
                180                 185                 190 ggg ctg ctg ggg gcc ctg tcc tac ctg ggc ctc acc cag gcc ggc ctc        2303
Gly Leu Leu Gly Ala Leu Ser Tyr Leu Gly Leu Thr Gln Ala Gly Leu
            195                 200                 205 tcc cct cag cag acc ctg ctg tcc atg ctg ggt atc cct gcc ctg ctg        2351
Ser Pro Gln Gln Thr Leu Leu Ser Met Leu Gly Ile Pro Ala Leu Leu
        210                 215                 220 ctg gcc agc tat ttc ttg ttg ctc aca tct cct gag gcc cag gac cct        2399
Leu Ala Ser Tyr Phe Leu Leu Leu Thr Ser Pro Glu Ala Gln Asp Pro
    225                 230                 235 gga ggg gaa gaa gaa gca gag agc gca gcc cgg cag ccc ctc ata aga        2447
Gly Gly Glu Glu Glu Ala Glu Ser Ala Ala Arg Gln Pro Leu Ile Arg
240                 245                 250                 255
```

```
acc gag gcc ccg gag tcg aag cca ggc tcc agc tcc agc ctc tcc ctt    2495
Thr Glu Ala Pro Glu Ser Lys Pro Gly Ser Ser Ser Ser Leu Ser Leu
                260                 265                 270 cgg gaa agg tgg aca gtg ttc aag ggt ctg ctg tgg tac att gtt ccc    2543
Arg Glu Arg Trp Thr Val Phe Lys Gly Leu Leu Trp Tyr Ile Val Pro
            275                 280                 285 ttg gtc gta gtt tac ttt gcc gag tat ttc att aac cag gga ctt ttt    2591
Leu Val Val Val Tyr Phe Ala Glu Tyr Phe Ile Asn Gln Gly Leu Phe
        290                 295                 300 gaa ctc ctc ttt ttc tgg aac act tcc ctg agt cac gct cag caa tac    2639
Glu Leu Leu Phe Phe Trp Asn Thr Ser Leu Ser His Ala Gln Gln Tyr
    305                 310                 315 cgc tgg tac cag atg ctg tac cag gct ggc gtc ttt gcc tcc cgc tct    2687
Arg Trp Tyr Gln Met Leu Tyr Gln Ala Gly Val Phe Ala Ser Arg Ser
320                 325                 330                 335 tct ctc cgc tgc tgt cgc atc cgt ttc acc tgg gcc ctg gcc ctg ctg    2735
Ser Leu Arg Cys Cys Arg Ile Arg Phe Thr Trp Ala Leu Ala Leu Leu
                340                 345                 350 cag tgc ctc aac ctg gtg ttc ctg ctg gca gac gtg tgg ttc ggc ttt    2783
Gln Cys Leu Asn Leu Val Phe Leu Leu Ala Asp Val Trp Phe Gly Phe
            355                 360                 365 ctg cca agc atc tac ctc gtc ttc ctg atc att ctg tat gag ggg ctc    2831
Leu Pro Ser Ile Tyr Leu Val Phe Leu Ile Ile Leu Tyr Glu Gly Leu
        370                 375                 380 ctg gga ggc gca gcc tac gtg aac acc ttc cac aac atc gcc ctg gag    2879
Leu Gly Gly Ala Ala Tyr Val Asn Thr Phe His Asn Ile Ala Leu Glu
    385                 390                 395 acc agt gat gag cac cgg gag ttt gca atg gcg gcc acc tgc atc tct    2927
Thr Ser Asp Glu His Arg Glu Phe Ala Met Ala Ala Thr Cys Ile Ser
400                 405                 410                 415 gac aca ctg ggg atc tcc ctg tcg ggg ctc ctg gct ttg cct ctg cat    2975
Asp Thr Leu Gly Ile Ser Leu Ser Gly Leu Leu Ala Leu Pro Leu His
                420                 425                 430 gac ttc ctc tgc cag ctc tcc tga cctgcaggtc tagaaagctt atcgataccg   3029
Asp Phe Leu Cys Gln Leu Ser
                435 tcgactagag ctcgctgatc agcctcgact gtgccttcta gttgccagcc atctgttgtt   3089 tgcccctccc ccgtgccttc cttgaccctg gaaggtgcca ctcccactgt cctttcctaa   3149 taaaatgagg aaattgcatc gcattgtctg agtaggtgtc attctattct gggggtgtgg   3209 gtggggcagg acagcaaggg ggaggattgg gaagacaata gcaggcatgc tggggagaga   3269 tcgatctgag gaacccctag tgatggagtt ggccactccc tctctgcgcg ctcgctcgct   3329 cactgaggcc gggcgaccaa aggtcgcccg acgcccgggc tttgcccggg cggcctcagt   3389 gagcgagcga gcgcgcagag agggagtggc ccccccccc cccccccgg cgattctctt    3449 gtttgctcca gactctcagg caatgacctg atagcctttg tagagacctc tcaaaaatag   3509 ctaccctctc cggcatgaat ttatcagcta gaacggttga atatcatatt gatggtgatt   3569 tgactgtctc cggcctttct caccgtttg aatctttacc tacacattac tcaggcattg   3629 catttaaaat atatgagggt tctaaaaatt tttatccttg cgttgaaata aaggcttctc   3689 ccgcaaaagt attacagggt cataatgttt ttggtacaac cgatttagct ttatgctctg   3749 aggctttatt gcttaatttt gctaattctt tgccttgcct gtatgattta ttggatgttg   3809 gaatcgcctg atgcggtatt ttctccttac gcatctgtgc ggtatttcac accgcatatg   3869 gtgcactctc agtacaatct gctctgatgc cgcatagtta agccagcccc gacacccgcc   3929
```

```
aacacccgct gacgcgccct gacgggcttg tctgctcccg gcatccgctt acagacaagc    3989
tgtgaccgtc tccgggagct gcatgtgtca gaggttttca ccgtcatcac cgaaacgcgc    4049
gagacgaaag ggcctcgtga tacgcctatt tttataggtt aatgtcatga taataatggt    4109
ttcttagacg tcaggtggca cttttcgggg aaatgtgcgc ggaaccccta tttgtttatt    4169
tttctaaata cattcaaata tgtatccgct catgagacaa taaccctgat aaatgcttca    4229
ataatattga aaaggaaga gtatgagtat tcaacatttc cgtgtcgccc ttattccctt    4289
ttttgcggca ttttgccttc ctgttttgc tcacccagaa acgctggtga agtaaaaga    4349 tgctgaagat cagttgggtg cacgagtggg ttacatcgaa ctggatctca acagcggtaa    4409
gatccttgag agttttcgcc ccgaagaacg ttttccaatg atgagcactt ttaaagttct    4469
gctatgtggc gcggtattat cccgtattga cgccgggcaa gagcaactcg gtcgccgcat    4529
acactattct cagaatgact tggttgagta ctcaccagtc acagaaaagc atcttacgga    4589
tggcatgaca gtaagagaat tatgcagtgc tgccataacc atgagtgata acactgcggc    4649
caacttactt ctgacaacga tcggaggacc gaaggagcta accgcttttt tgcacaacat    4709
gggggatcat gtaactcgcc ttgatcgttg ggaaccggag ctgaatgaag ccataccaaa    4769
cgacgagcgt gacaccacga tgcctgtagc aatggcaaca acgttgcgca aactattaac    4829
tggcgaacta cttactctag cttcccggca acaattaata gactggatgg aggcggataa    4889
agttgcagga ccacttctgc gctcggccct tccggctggc tggtttattg ctgataaatc    4949
tggagccggt gagcgtgggt ctcgcggtat cattgcagca ctggggccag atggtaagcc    5009
ctcccgtatc gtagttatct acacgacggg gagtcaggca actatggatg aacgaaatag    5069
acagatcgct gagataggtg cctcactgat taagcattgg taactgtcag accaagttta    5129
ctcatatata ctttagattg atttaaaact tcatttttaa tttaaaagga tctaggtgaa    5189 gatcctttt gataatctca tgaccaaaat cccttaacgt gagttttcgt tccactgagc    5249
gtcagacccc gtagaaaaga tcaaaggatc ttcttgagat cctttttttc tgcgcgtaat    5309
ctgctgcttg caaacaaaaa aaccaccgct accagcggtg gtttgtttgc cggatcaaga    5369
gctaccaact ctttttccga aggtaactgg cttcagcaga gcgcagatac caaatactgt    5429
ccttctagtg tagccgtagt taggccacca cttcaagaac tctgtagcac cgcctacata    5489
cctcgctctg ctaatcctgt taccagtggc tgctgccagt ggcgataagt cgtgtcttac    5549
cgggttggac tcaagacgat agttaccgga taaggcgcag cggtcgggct gaacggggg    5609 ttcgtgcaca cagcccagct tggagcgaac gacctacacc gaactgagat acctacagcg    5669
tgagctatga gaaagcgcca cgcttcccga agggagaaag gcggacaggt atccggtaag    5729
cggcagggtc ggaacaggag agcgcacgag ggagcttcca gggggaaacg cctggtatct    5789
ttatagtcct gtcgggtttc gccacctctg acttgagcgt cgatttttgt gatgctcgtc    5849
aggggggcgg agcctatgga aaaacgccag caacgcggcc tttttacggt tcctggcctt    5909
ttgctggcct tttgctcaca tgttctttcc tgcgttatcc cctgattctg tggataaccg    5969
tattaccgcc tttgagtgag ctgataccgc tcgccgcagc cgaacgaccg agcgcagcga    6029
gtcagtgagc gaggaagcgg aagagc                                        6055
```

<210> SEQ ID NO 3
<211> LENGTH: 6
<212> TYPE: DNA
<213> ORGANISM: Artificial Sequence
<220> FEATURE:
<223> OTHER INFORMATION: Description of Artificial Sequence: Synthetic polyadenylation signal sequence

<400> SEQUENCE: 3 aataaa                                                                          6

<210> SEQ ID NO 4
<211> LENGTH: 7
<212> TYPE: DNA
<213> ORGANISM: Artificial Sequence
<220> FEATURE:
<223> OTHER INFORMATION: Description of Artificial Sequence: Synthetic
      polyadenylation signal sequence

<400> SEQUENCE: 4 caataaa                                                                         7

<210> SEQ ID NO 5
<211> LENGTH: 6
<212> TYPE: DNA
<213> ORGANISM: Artificial Sequence
<220> FEATURE:
<223> OTHER INFORMATION: Description of Artificial Sequence: Synthetic
      polyadenylation signal sequence

<400> SEQUENCE: 5 attaaa                                                                          6

<210> SEQ ID NO 6
<211> LENGTH: 4
<212> TYPE: DNA
<213> ORGANISM: Artificial Sequence
<220> FEATURE:
<223> OTHER INFORMATION: Description of Artificial Sequence: Synthetic
      polyadenylation signal sequence
<220> FEATURE:
<221> NAME/KEY: modified_base
<222> LOCATION: (3)..(3)
<223> OTHER INFORMATION: a, c, t, g, unknown or other

<400> SEQUENCE: 6 tana                                                                            4

<210> SEQ ID NO 7
<211> LENGTH: 438
<212> TYPE: PRT
<213> ORGANISM: Canis lupus
<220> FEATURE:
<223> OTHER INFORMATION: CLN3

<400> SEQUENCE: 7

Met Gly Gly Cys Ala Gly Ser Arg Arg Leu Leu Asp Ser Glu Glu
1               5                   10                  15

Glu Glu Thr Ala Pro Glu Pro Arg Pro Arg Ser Tyr His Lys Gly
                20                  25                  30

Ala Leu Trp Lys Asn Val Met Gly Phe Trp Leu Leu Gly Leu Cys Asn
            35                  40                  45

Asn Phe Ser Tyr Val Val Met Leu Ser Ala Ala His Asp Ile Leu Ser
        50                  55                  60

His Gln Arg Ala Ser Gly Asn Gln Ser His Val Asp Pro Asp Pro Pro
65                  70                  75                  80

Pro Thr Ala His Asn Ser Ser Ser Arg Phe Asp Cys Asn Ser Val Ser
                85                  90                  95

Thr Ala Ala Val Leu Leu Ala Asp Ile Leu Pro Thr Leu Ile Ile Lys
                100                 105                 110

```
Leu Leu Ala Pro Leu Gly Leu His Leu Leu Pro Tyr Ser Pro Arg Val
            115                 120                 125

Leu Val Ser Gly Ile Cys Ala Gly Ser Phe Ile Leu Val Ala Phe
130                 135                 140

Ser His Ser Val Gly Thr Ser Leu Cys Gly Val Val Leu Ala Ser Ile
145                 150                 155                 160

Ser Ser Gly Val Gly Glu Val Thr Phe Leu Ser Leu Thr Ala Phe Tyr
                165                 170                 175

Pro Arg Ala Val Ile Ser Trp Trp Ser Ser Thr Gly Gly Ala Gly
            180                 185                 190

Leu Met Gly Ala Leu Ser Tyr Leu Gly Leu Thr Gln Ala Gly Leu Ser
            195                 200                 205

Pro Gln His Thr Leu Leu Ser Met Leu Gly Ile Pro Ala Leu Met Leu
            210                 215                 220

Ala Ser Tyr Phe Phe Leu Leu Thr Ser Pro Glu Pro Gln Asp Pro Gly
225                 230                 235                 240

Gly Glu Glu Glu Ala Glu Thr Ser Ala Arg Gln Pro Leu Ile Asp Ser
                245                 250                 255

Glu Thr Pro Glu Ser Lys Pro Asp Ser Ser Asn Leu Ser Leu Gln
            260                 265                 270

Glu Arg Trp Thr Val Phe Lys Gly Leu Leu Trp Tyr Ile Val Pro Leu
            275                 280                 285

Val Leu Val Tyr Phe Ala Glu Tyr Phe Ile Asn Gln Gly Leu Phe Glu
            290                 295                 300

Leu Leu Phe Phe Arg Asn Thr Ser Leu Asn His Ala Gln Gln Tyr Arg
305                 310                 315                 320

Trp Tyr Gln Met Leu Tyr Gln Ala Gly Val Phe Val Ser Arg Ser Ser
                325                 330                 335

Leu His Cys Cys Arg Ile Arg Phe Thr Trp Val Leu Ala Leu Leu Gln
            340                 345                 350

Cys Leu Asn Leu Ala Phe Leu Leu Val Asp Val Trp Phe Ser Phe Leu
            355                 360                 365

Pro Ser Ile Tyr Leu Val Phe Leu Ile Ile Leu Tyr Glu Gly Leu Leu
            370                 375                 380

Gly Gly Ala Ala Tyr Val Asn Thr Phe His Asn Ile Ala Leu Glu Thr
385                 390                 395                 400

Ser Asp Gln His Arg Glu Phe Ala Met Ala Ala Cys Ile Ser Asp
                405                 410                 415

Thr Leu Gly Ile Ser Leu Ser Gly Leu Leu Ala Leu Pro Leu His Asp
            420                 425                 430

Phe Leu Cys His Leu Ser
            435

<210> SEQ ID NO 8
<211> LENGTH: 438
<212> TYPE: PRT
<213> ORGANISM: Mus musculus
<220> FEATURE:
<223> OTHER INFORMATION: CLN3

<400> SEQUENCE: 8

Met Gly Ser Ser Ala Gly Ser Trp Arg Arg Leu Glu Asp Ser Glu Arg
1               5                   10                  15

Glu Glu Thr Asp Ser Glu Pro Gln Ala Pro Arg Leu Asp Ser Arg Ser
            20                  25                  30
```

-continued

Val Leu Trp Lys Asn Ala Val Gly Phe Trp Ile Leu Gly Leu Cys Asn
                35                  40                  45

Asn Phe Ser Tyr Val Val Met Leu Ser Ala Ala His Asp Ile Leu Lys
 50                  55                  60

Gln Glu Gln Ala Ser Gly Asn Gln Ser His Val Glu Pro Gly Pro Thr
 65                  70                  75                  80

Pro Thr Pro His Asn Ser Ser Ser Arg Phe Asp Cys Asn Ser Ile Ser
                85                  90                  95

Thr Ala Ala Val Leu Leu Ala Asp Ile Leu Pro Thr Leu Val Ile Lys
                100                 105                 110

Leu Leu Ala Pro Leu Gly Leu His Leu Leu Pro Tyr Ser Pro Arg Val
                115                 120                 125

Leu Val Ser Gly Val Cys Ser Ala Gly Ser Phe Val Leu Val Ala Phe
                130                 135                 140

Ser Gln Ser Val Gly Leu Ser Leu Cys Gly Val Val Leu Ala Ser Ile
145                 150                 155                 160

Ser Ser Gly Leu Gly Glu Val Thr Phe Leu Ser Leu Thr Ala Phe Tyr
                165                 170                 175

Pro Ser Ala Val Ile Ser Trp Trp Ser Ser Gly Thr Gly Ala Gly
                180                 185                 190

Leu Leu Gly Ser Leu Ser Tyr Leu Gly Leu Thr Gln Ala Gly Leu Ser
                195                 200                 205

Pro Gln His Thr Leu Leu Ser Met Leu Gly Ile Pro Val Leu Leu Leu
                210                 215                 220

Ala Ser Tyr Phe Leu Leu Leu Thr Ser Pro Glu Pro Leu Asp Pro Gly
225                 230                 235                 240

Gly Glu Asn Glu Ala Glu Thr Ala Ala Arg Gln Pro Leu Ile Gly Thr
                245                 250                 255

Glu Thr Pro Glu Ser Lys Pro Gly Ala Ser Trp Asp Leu Ser Leu Gln
                260                 265                 270

Glu Arg Trp Thr Val Phe Lys Gly Leu Leu Trp Tyr Ile Ile Pro Leu
                275                 280                 285

Val Leu Val Tyr Phe Ala Glu Tyr Phe Ile Asn Gln Gly Leu Phe Glu
                290                 295                 300

Leu Leu Phe Phe Arg Asn Thr Ser Leu Ser His Ala Gln Gln Tyr Arg
305                 310                 315                 320

Trp Tyr Gln Met Leu Tyr Gln Ala Gly Val Phe Ala Ser Arg Ser Ser
                325                 330                 335

Leu Gln Cys Cys Arg Ile Arg Phe Thr Trp Val Leu Ala Leu Leu Gln
                340                 345                 350

Cys Leu Asn Leu Ala Leu Leu Ala Asp Val Cys Leu Asn Phe Leu
                355                 360                 365

Pro Ser Ile Tyr Leu Ile Phe Ile Ile Leu Tyr Glu Gly Leu Leu
                370                 375                 380

Gly Gly Ala Ala Tyr Val Asn Thr Phe His Asn Ile Ala Leu Glu Thr
385                 390                 395                 400

Ser Asp Lys His Arg Glu Phe Ala Met Glu Ala Ala Cys Ile Ser Asp
                405                 410                 415

Thr Leu Gly Ile Ser Leu Ser Gly Val Leu Ala Leu Pro Leu His Asp
                420                 425                 430

Phe Leu Cys His Leu Pro
                435

<210> SEQ ID NO 9
<211> LENGTH: 438
<212> TYPE: PRT
<213> ORGANISM: Ovis aries
<220> FEATURE:
<223> OTHER INFORMATION: CLN3

<400> SEQUENCE: 9

```
Met Gly Gly Cys Ala Gly Ser Pro Arg Arg Leu Ser Asp Ser Glu Gly
1               5                   10                  15

Glu Glu Thr Asp Pro Ala Pro Arg Pro Pro Leu Gln Asp Ser Gln Gly
            20                  25                  30

Ala His Trp Lys Asn Ala Val Gly Phe Trp Leu Leu Gly Leu Cys Asn
        35                  40                  45

Asn Phe Ser Tyr Val Val Met Leu Ser Ala Ala His Asp Ile Leu Ser
    50                  55                  60

His Gln Arg Thr Ala Gly Asn Gln Ser His Val Asp Pro Asp Pro Thr
65                  70                  75                  80

Pro Thr Ser His Asn Ser Ser Ser Arg Phe Asp Cys Asn Pro Val Ser
                85                  90                  95

Thr Ala Ala Val Leu Leu Ala Asp Ile Leu Pro Thr Leu Ile Ile Lys
            100                 105                 110

Leu Leu Ala Pro Leu Gly Leu His Leu Leu Pro Tyr Ser Pro Arg Val
        115                 120                 125

Leu Thr Ser Gly Ile Cys Ala Ala Gly Ser Phe Leu Leu Val Ala Phe
    130                 135                 140

Ser His Ser Val Met Ile Ser Leu Cys Gly Val Leu Ala Ser Ile
145                 150                 155                 160

Ser Ser Gly Leu Gly Glu Val Thr Phe Leu Ser Leu Thr Ala Phe Tyr
                165                 170                 175

Pro Arg Ala Val Ile Ser Cys Trp Ser Ser Gly Thr Gly Ala Gly
            180                 185                 190

Leu Leu Gly Ala Leu Ser Tyr Leu Gly Leu Thr Gln Ala Gly Leu Ser
        195                 200                 205

Pro Gln His Thr Leu Leu Ser Met Leu Gly Ile Pro Thr Leu Leu
    210                 215                 220

Ala Ser Tyr Phe Leu Leu Leu Thr Ser Pro Gly Pro Gln Asp Pro Arg
225                 230                 235                 240

Gly Glu Glu Asp Ser Asp Thr Ala Ala Arg Gln Pro Leu Ile Asn Asn
                245                 250                 255

Glu Ala Ser Glu Ser Lys Pro Gly Ser Gly Ser Pro Leu Ser Leu Gln
            260                 265                 270

Glu Arg Trp Thr Val Phe Lys Gly Leu Leu His Tyr Ile Val Pro Leu
        275                 280                 285

Val Leu Val Tyr Phe Ala Glu Tyr Phe Ile Asn Gln Gly Leu Phe Glu
    290                 295                 300

Leu Leu Phe Phe Arg Asn Thr Phe Leu Thr His Ala Glu Gln Tyr Arg
305                 310                 315                 320

Trp Tyr Gln Met Leu Tyr Gln Ala Gly Val Phe Ala Ser Arg Ser Ser
                325                 330                 335

Leu Arg Cys Cys Pro Ile Arg His Thr Trp Val Leu Ala Leu Leu Gln
            340                 345                 350

Cys Leu Asn Leu Ala Phe Leu Leu Val Asp Val Trp Leu Ser Phe Leu
        355                 360                 365
```

```
Pro Ser Ile Tyr Leu Ile Phe Leu Ile Ile Val Phe Glu Gly Leu Leu
            370             375             380

Gly Gly Ala Ala Tyr Val Asn Thr Phe His Asn Ile Ala Leu Glu Thr
385             390             395             400

Ser Asp Glu His Arg Glu Phe Ala Met Ala Thr Ala Cys Ile Ser Asp
            405             410             415

Thr Leu Gly Ile Ser Leu Ser Gly Leu Leu Ala Leu Pro Leu His Asp
            420             425             430

Phe Leu Cys Gln Leu Thr
            435

<210> SEQ ID NO 10
<211> LENGTH: 438
<212> TYPE: PRT
<213> ORGANISM: Felis catus
<220> FEATURE:
<223> OTHER INFORMATION: CLN3
<220> FEATURE:
<221> NAME/KEY: MOD_RES
<222> LOCATION: (411)..(411)
<223> OTHER INFORMATION: Any amino acid

<400> SEQUENCE: 10

Met Gly Gly Cys Ala Gly Ser Arg Arg Arg Leu Leu Asp Ser Glu Gly
1               5                   10                  15

Glu Glu Thr Ala Pro Glu Pro Arg Pro Arg Leu Leu Asp Arg Gln Gly
            20                  25                  30

Ala Leu Trp Lys Asn Ala Met Gly Phe Trp Leu Leu Gly Leu Cys Asn
        35                  40                  45

Asn Phe Ser Tyr Val Val Met Leu Ser Ala Ala His Asp Ile Leu Ser
    50                  55                  60

His Gln Arg Ala Ser Gly Asn Gln Ser His Val Asp Pro Asp Pro Ala
65                  70                  75                  80

Pro Thr Thr His Asn Ser Ser Ser Arg Phe Asp Cys Asn Ser Val Ser
                85                  90                  95

Thr Ala Ala Val Leu Leu Ala Asp Ile Leu Pro Thr Leu Val Ile Lys
            100                 105                 110

Leu Leu Ala Pro Leu Gly Leu His Leu Leu Pro Tyr Ser Pro Arg Val
        115                 120                 125

Leu Val Ser Gly Ile Cys Ser Ala Gly Ser Phe Ile Leu Val Ala Phe
    130                 135                 140

Ser His Ser Val Gly Thr Ser Leu Cys Gly Val Val Leu Ala Ser Ile
145                 150                 155                 160

Ser Ser Gly Leu Gly Glu Val Thr Phe Leu Ser Leu Thr Ala Phe Tyr
                165                 170                 175

Pro Arg Ala Val Ile Ser Trp Trp Ser Ser Gly Thr Gly Gly Ala Gly
            180                 185                 190

Leu Leu Gly Ala Leu Ser Tyr Leu Gly Leu Thr Gln Ala Gly Leu Ser
        195                 200                 205

Pro Gln His Thr Leu Leu Ser Met Leu Gly Ile Pro Ala Leu Leu Leu
    210                 215                 220

Ala Ser Tyr Phe Phe Leu Leu Thr Ser Pro Glu Pro Gln Asp Pro Gly
225                 230                 235                 240

Gly Glu Glu Glu Ala Glu Thr Ser Ala Arg Gln Pro Leu Ile Asn Ser
                245                 250                 255

Glu Ala Pro Glu Ala Lys Pro Asp Ser Ser Ser Asn Leu Ser Leu Gln
            260                 265                 270
```

Glu Arg Trp Thr Val Phe Lys Gly Leu Leu Trp Tyr Ile Val Pro Leu
    275                 280                 285

Val Leu Val Tyr Phe Ala Glu Tyr Phe Ile Asn Gln Gly Leu Phe Glu
    290                 295                 300

Leu Leu Phe Phe Arg Asn Thr Ser Leu Thr His Ala Gln Gln Tyr Arg
305                 310                 315                 320

Trp Tyr Gln Met Leu Tyr Gln Ala Gly Val Phe Val Ser Arg Ser Ser
                325                 330                 335

Leu Arg Cys Cys Arg Ile Arg Phe Thr Trp Val Leu Ala Leu Leu Gln
            340                 345                 350

Cys Phe Asn Leu Ala Phe Leu Leu Val Asp Val Trp Leu Ser Phe Leu
                355                 360                 365

Pro Ser Ile Tyr Leu Val Phe Leu Ile Ile Leu Tyr Glu Gly Leu Leu
    370                 375                 380

Gly Gly Ala Ala Tyr Val Asn Thr Phe His Asn Ile Ala Leu Glu Thr
385                 390                 395                 400

Ser Asp Glu His Arg Glu Phe Ala Met Ala Xaa Ala Cys Ile Ser Asp
                405                 410                 415

Thr Leu Gly Ile Ser Leu Ser Gly Leu Leu Ala Leu Pro Leu His Asp
            420                 425                 430

Phe Leu Cys Arg Leu Ser
        435

<210> SEQ ID NO 11
<211> LENGTH: 1317
<212> TYPE: DNA
<213> ORGANISM: Homo sapiens
<220> FEATURE:
<223> OTHER INFORMATION: CLN3, variant 2 mRNA

<400> SEQUENCE: 11
atgggaggct gtgcaggctc gcggcggcgc ttttcggatt ccgaggggga ggagaccgtc     60
ccggagcccc ggctccctct gttggaccat cagggcgcgc attggaagaa cgcggtgggc    120
ttctggctgc tgggccttgt caacaacttc tcttatgtgg tgatgctgag tgccgcccac    180
gacatcctta gccacaagag gacatcggga accagagcc atgtggaccc aggcccaacg    240
ccgatccccc acaacagctc atcacgattt gactgcaact ctgtctctac ggctgctgtg    300
ctcctggcgg acatcctccc cacactcgtc atcaaattgt ggctcctct tggccttcac    360 ctgctgccct acagccccg ggttctcgtc agtgggattt gtgctgctgg aagcttcgtc    420
ctggttgcct tttctcattc tgtggggacc agcctgtgtg gtgtggtctt cgctagcatc    480
tcatcaggcc ttggggaggt caccttcctc tccctcactg ccttctaccc agggccgtg     540 atctcctggt ggtcctcagg gactggggga gctgggctgc tggggcccct gtcctacctg    600
ggcctcaccc aggccggcct ctcccctcag cagaccctgc tgtccatgct gggtatccct    660
gccctgctgc tggccagcta tttcttgttg ctcacatctc ctgaggccca ggaccctgga    720
ggggaagaag aagcagagag cgcagcccgg cagccctca taagaaccga ggccccggag    780
tcgaagccag gctccagctc agcctctcc cttcgggaaa ggtggacagt gttcaagggt    840
ctgctgtggt acattgttcc cttggtcgta gtttactttg ccgagtattt cattaaccag    900 ggacttttg aactcctctt tttctggaac acttccctga gtcacgctca gcaataccgc    960
tggtaccaga tgctgtacca ggctggcgta tttgcctccc gctcttctct ccgctgctgt   1020
cgcatccgtt tcacctgggc cctggccctg ctgcagtgcc tcaacctggt gttcctgctg   1080

```
gcagacgtgt ggttcggctt tctgccaagc atctacctcg tcttcctgat cattctgtat      1140
gaggggctcc tgggaggcgc agcctacgtg aacaccttcc acaacatcgc cctggagacc      1200
agtgatgagc accgggagtt tgcaatggcg gccacctgca tctctgacac actggggatc      1260
tccctgtcgg ggctcctggc tttgcctctg catgacttcc tctgccagct ctcctga        1317
```

<210> SEQ ID NO 12
<211> LENGTH: 735
<212> TYPE: PRT
<213> ORGANISM: Artificial Sequence
<220> FEATURE:
<223> OTHER INFORMATION: Description of Artificial Sequence: Synthetic
      AAV2 VP1 sequence

<400> SEQUENCE: 12

```
Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Arg Leu Asn Phe Lys Leu Phe Asn Ile Gln Val
305                 310                 315                 320
```

```
Lys Glu Val Thr Gln Asn Asp Gly Thr Thr Thr Ile Ala Asn Asn Leu
                325                 330                 335
Thr Ser Thr Val Gln Val Phe Thr Asp Ser Glu Tyr Gln Leu Pro Tyr
            340                 345                 350
Val Leu Gly Ser Ala His Gln Gly Cys Leu Pro Pro Phe Pro Ala Asp
        355                 360                 365
Val Phe Met Val Pro Gln Tyr Gly Tyr Leu Thr Leu Asn Asn Gly Ser
    370                 375                 380
Gln Ala Val Gly Arg Ser Ser Phe Tyr Cys Leu Glu Tyr Phe Pro Ser
385                 390                 395                 400
Gln Met Leu Arg Thr Gly Asn Asn Phe Thr Phe Ser Tyr Thr Phe Glu
            405                 410                 415
Asp Val Pro Phe His Ser Ser Tyr Ala His Ser Gln Ser Leu Asp Arg
        420                 425                 430
Leu Met Asn Pro Leu Ile Asp Gln Tyr Leu Tyr Tyr Leu Ser Arg Thr
    435                 440                 445
Asn Thr Pro Ser Gly Thr Thr Thr Gln Ser Arg Leu Gln Phe Ser Gln
450                 455                 460
Ala Gly Ala Ser Asp Ile Arg Asp Gln Ser Arg Asn Trp Leu Pro Gly
465                 470                 475                 480
Pro Cys Tyr Arg Gln Gln Arg Val Ser Lys Thr Ser Ala Asp Asn Asn
            485                 490                 495
Asn Ser Glu Tyr Ser Trp Thr Gly Ala Thr Lys Tyr His Leu Asn Gly
        500                 505                 510
Arg Asp Ser Leu Val Asn Pro Gly Pro Ala Met Ala Ser His Lys Asp
    515                 520                 525
Asp Glu Glu Lys Phe Phe Pro Gln Ser Gly Val Leu Ile Phe Gly Lys
530                 535                 540
Gln Gly Ser Glu Lys Thr Asn Val Asp Ile Glu Lys Val Met Ile Thr
545                 550                 555                 560
Asp Glu Glu Glu Ile Arg Thr Thr Asn Pro Val Ala Thr Glu Gln Tyr
            565                 570                 575
Gly Ser Val Ser Thr Asn Leu Gln Arg Gly Asn Arg Gln Ala Ala Thr
        580                 585                 590
Ala Asp Val Asn Thr Gln Gly Val Leu Pro Gly Met Val Trp Gln Asp
    595                 600                 605
Arg Asp Val Tyr Leu Gln Gly Pro Ile Trp Ala Lys Ile Pro His Thr
610                 615                 620
Asp Gly His Phe His Pro Ser Pro Leu Met Gly Gly Phe Gly Leu Lys
625                 630                 635                 640
His Pro Pro Pro Gln Ile Leu Ile Lys Asn Thr Pro Val Pro Ala Asn
            645                 650                 655
Pro Ser Thr Thr Phe Ser Ala Ala Lys Phe Ala Ser Phe Ile Thr Gln
        660                 665                 670
Tyr Ser Thr Gly Gln Val Ser Val Glu Ile Glu Trp Glu Leu Gln Lys
    675                 680                 685
Glu Asn Ser Lys Arg Trp Asn Pro Glu Ile Gln Tyr Thr Ser Asn Tyr
690                 695                 700
Asn Lys Ser Val Asn Val Asp Phe Thr Val Asp Thr Asn Gly Val Tyr
705                 710                 715                 720
Ser Glu Pro Arg Pro Ile Gly Thr Arg Tyr Leu Thr Arg Asn Leu
            725                 730                 735
```

<210> SEQ ID NO 13
<211> LENGTH: 745
<212> TYPE: PRT
<213> ORGANISM: Artificial Sequence
<220> FEATURE:
<223> OTHER INFORMATION: Description of Artificial Sequence: Synthetic AAV9 VP1 sequence

<400> SEQUENCE: 13

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365
```

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
            405                 410                 415

Phe Glu Asn Val Pro Phe His Ser Ser Tyr Ala His Ser Gln Ser Leu
        420                 425                 430

Asp Arg Leu Met Asn Pro Leu Ile Asp Gln Tyr Leu Tyr Tyr Leu Ser
    435                 440                 445

Lys Thr Ile Asn Gly Ser Gly Gln Asn Gln Gln Thr Leu Lys Phe Ser
450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
            485                 490                 495

Asn Asn Ser Glu Phe Ala Trp Pro Gly Ala Ser Ser Trp Ala Leu Asn
        500                 505                 510

Gly Arg Asn Ser Leu Met Asn Pro Gly Pro Ala Met Ala Ser His Lys
    515                 520                 525

Glu Gly Glu Asp Arg Phe Phe Pro Leu Ser Gly Ser Leu Ile Phe Gly
530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
            565                 570                 575

Tyr Gly Gln Val Ala Thr Asn His Gln Gly Gln Arg Gly Asn Tyr Ser
        580                 585                 590

Arg Gly Val Asp Ala Gln Ala Ala Gln Thr Gly Trp Val Gln Asn Gln
    595                 600                 605

Gly Ile Leu Pro Gly Met Val Trp Gln Asp Arg Asp Val Tyr Leu Gln
610                 615                 620

Gly Pro Ile Trp Ala Lys Ile Pro His Thr Asp Gly Asn Phe His Pro
625                 630                 635                 640

Ser Pro Leu Met Gly Gly Phe Gly Met Lys His Pro Pro Gln Ile
            645                 650                 655

Leu Ile Lys Asn Thr Pro Val Pro Ala Asp Pro Pro Thr Ala Phe Asn
        660                 665                 670

Lys Asp Lys Leu Asn Ser Phe Ile Thr Gln Tyr Ser Thr Gly Gln Val
    675                 680                 685

Ser Val Glu Ile Glu Trp Glu Leu Gln Lys Glu Asn Ser Lys Arg Trp
690                 695                 700

Asn Pro Glu Ile Gln Tyr Thr Ser Asn Tyr Tyr Lys Ser Asn Asn Val
705                 710                 715                 720

Glu Phe Ala Val Asn Thr Glu Gly Val Tyr Ser Glu Pro Arg Pro Ile
            725                 730                 735

Gly Thr Arg Tyr Leu Thr Arg Asn Leu
        740                 745

<210> SEQ ID NO 14
<211> LENGTH: 598
<212> TYPE: PRT
<213> ORGANISM: Artificial Sequence
<220> FEATURE:

<223> OTHER INFORMATION: Description of Artificial Sequence: Synthetic AAV2 VP2 sequence

<400> SEQUENCE: 14

```
Met Ala Pro Gly Lys Lys Arg Pro Val Glu His Ser Pro Val Glu Pro
1               5                   10                  15

Asp Ser Ser Gly Thr Gly Lys Ala Gly Gln Gln Pro Ala Arg Lys
            20                  25                  30

Arg Leu Asn Phe Gly Gln Thr Gly Asp Ala Asp Ser Val Pro Asp Pro
            35                  40                  45

Gln Pro Leu Gly Gln Pro Pro Ala Ala Pro Ser Gly Leu Gly Thr Asn
50                  55                  60

Thr Met Ala Thr Gly Ser Gly Ala Pro Met Ala Asp Asn Asn Glu Gly
65                  70                  75                  80

Ala Asp Gly Val Gly Asn Ser Ser Gly Asn Trp His Cys Asp Ser Thr
                85                  90                  95

Trp Met Gly Asp Arg Val Ile Thr Thr Ser Thr Arg Thr Trp Ala Leu
            100                 105                 110

Pro Thr Tyr Asn Asn His Leu Tyr Lys Gln Ile Ser Ser Gln Ser Gly
            115                 120                 125

Ala Ser Asn Asp Asn His Tyr Phe Gly Tyr Ser Thr Pro Trp Gly Tyr
        130                 135                 140

Phe Asp Phe Asn Arg Phe His Cys His Phe Ser Pro Arg Asp Trp Gln
145                 150                 155                 160

Arg Leu Ile Asn Asn Asn Trp Gly Phe Arg Pro Lys Arg Leu Asn Phe
                165                 170                 175

Lys Leu Phe Asn Ile Gln Val Lys Glu Val Thr Gln Asn Asp Gly Thr
            180                 185                 190

Thr Thr Ile Ala Asn Asn Leu Thr Ser Thr Val Gln Val Phe Thr Asp
        195                 200                 205

Ser Glu Tyr Gln Leu Pro Tyr Val Leu Gly Ser Ala His Gln Gly Cys
210                 215                 220

Leu Pro Pro Phe Pro Ala Asp Val Phe Met Val Pro Gln Tyr Gly Tyr
225                 230                 235                 240

Leu Thr Leu Asn Asn Gly Ser Gln Ala Val Gly Arg Ser Ser Phe Tyr
                245                 250                 255

Cys Leu Glu Tyr Phe Pro Ser Gln Met Leu Arg Thr Gly Asn Asn Phe
            260                 265                 270

Thr Phe Ser Tyr Thr Phe Glu Asp Val Pro Phe His Ser Ser Tyr Ala
        275                 280                 285

His Ser Gln Ser Leu Asp Arg Leu Met Asn Pro Leu Ile Asp Gln Tyr
290                 295                 300

Leu Tyr Tyr Leu Ser Arg Thr Asn Thr Pro Ser Gly Thr Thr Thr Gln
305                 310                 315                 320

Ser Arg Leu Gln Phe Ser Gln Ala Gly Ala Ser Asp Ile Arg Asp Gln
                325                 330                 335

Ser Arg Asn Trp Leu Pro Gly Pro Cys Tyr Arg Gln Gln Arg Val Ser
            340                 345                 350

Lys Thr Ser Ala Asp Asn Asn Asn Ser Glu Tyr Ser Trp Thr Gly Ala
        355                 360                 365

Thr Lys Tyr His Leu Asn Gly Arg Asp Ser Leu Val Asn Pro Gly Pro
370                 375                 380

Ala Met Ala Ser His Lys Asp Asp Glu Glu Lys Phe Phe Pro Gln Ser
385                 390                 395                 400
```

Gly Val Leu Ile Phe Gly Lys Gln Gly Ser Glu Lys Thr Asn Val Asp
                405                 410                 415

Ile Glu Lys Val Met Ile Thr Asp Glu Glu Ile Arg Thr Thr Asn
            420                 425                 430

Pro Val Ala Thr Glu Gln Tyr Gly Ser Val Ser Thr Asn Leu Gln Arg
            435                 440                 445

Gly Asn Arg Gln Ala Ala Thr Ala Asp Val Asn Thr Gln Gly Val Leu
        450                 455                 460

Pro Gly Met Val Trp Gln Asp Arg Asp Val Tyr Leu Gln Gly Pro Ile
465                 470                 475                 480

Trp Ala Lys Ile Pro His Thr Asp Gly His Phe His Pro Ser Pro Leu
                485                 490                 495

Met Gly Gly Phe Gly Leu Lys His Pro Pro Pro Gln Ile Leu Ile Lys
            500                 505                 510

Asn Thr Pro Val Pro Ala Asn Pro Ser Thr Thr Phe Ser Ala Ala Lys
        515                 520                 525

Phe Ala Ser Phe Ile Thr Gln Tyr Ser Thr Gly Gln Val Ser Val Glu
        530                 535                 540

Ile Glu Trp Glu Leu Gln Lys Glu Asn Ser Lys Arg Trp Asn Pro Glu
545                 550                 555                 560

Ile Gln Tyr Thr Ser Asn Tyr Asn Lys Ser Val Asn Val Asp Phe Thr
                565                 570                 575

Val Asp Thr Asn Gly Val Tyr Ser Glu Pro Arg Pro Ile Gly Thr Arg
            580                 585                 590

Tyr Leu Thr Arg Asn Leu
        595

<210> SEQ ID NO 15
<211> LENGTH: 518
<212> TYPE: PRT
<213> ORGANISM: Artificial Sequence
<220> FEATURE:
<223> OTHER INFORMATION: Description of Artificial Sequence: Synthetic
      AAV9 VP2 sequence

<400> SEQUENCE: 15

Asp Gly Val Gly Ser Ser Ser Gly Asn Trp His Cys Asp Ser Gln Trp
1               5                   10                  15

Leu Gly Asp Arg Val Ile Thr Thr Ser Thr Arg Thr Trp Ala Leu Pro
            20                  25                  30

Thr Tyr Asn Asn His Leu Tyr Lys Gln Ile Ser Asn Ser Thr Ser Gly
        35                  40                  45

Gly Ser Ser Asn Asp Asn Ala Tyr Phe Gly Tyr Ser Thr Pro Trp Gly
    50                  55                  60

Tyr Phe Asp Phe Asn Arg Phe His Cys His Phe Ser Pro Arg Asp Trp
65                  70                  75                  80

Gln Arg Leu Ile Asn Asn Asn Trp Gly Phe Arg Pro Lys Arg Leu Asn
                85                  90                  95

Phe Lys Leu Phe Asn Ile Gln Val Lys Glu Val Thr Asp Asn Asn Gly
            100                 105                 110

Val Lys Thr Ile Ala Asn Asn Leu Thr Ser Thr Val Gln Val Phe Thr
        115                 120                 125

Asp Ser Asp Tyr Gln Leu Pro Tyr Val Leu Gly Ser Ala His Glu Gly
    130                 135                 140

Cys Leu Pro Pro Phe Pro Ala Asp Val Phe Met Ile Pro Gln Tyr Gly

```
            145                 150                 155                 160
Tyr Leu Thr Leu Asn Asp Gly Ser Gln Ala Val Gly Arg Ser Ser Phe
            165                 170                 175
Tyr Cys Leu Glu Tyr Phe Pro Ser Gln Met Leu Arg Thr Gly Asn Asn
            180                 185                 190
Phe Gln Phe Ser Tyr Glu Phe Glu Asn Val Pro Phe His Ser Ser Tyr
            195                 200                 205
Ala His Ser Gln Ser Leu Asp Arg Leu Met Asn Pro Leu Ile Asp Gln
            210                 215                 220
Tyr Leu Tyr Tyr Leu Ser Lys Thr Ile Asn Gly Ser Gly Gln Asn Gln
225                 230                 235                 240
Gln Thr Leu Lys Phe Ser Val Ala Gly Pro Ser Asn Met Ala Val Gln
            245                 250                 255
Gly Arg Asn Tyr Ile Pro Gly Pro Ser Tyr Arg Gln Gln Arg Val Ser
            260                 265                 270
Thr Thr Val Thr Gln Asn Asn Asn Ser Glu Phe Ala Trp Pro Gly Ala
            275                 280                 285
Ser Ser Trp Ala Leu Asn Gly Arg Asn Ser Leu Met Asn Pro Gly Pro
            290                 295                 300
Ala Met Ala Ser His Lys Glu Gly Glu Asp Arg Phe Phe Pro Leu Ser
305                 310                 315                 320
Gly Ser Leu Ile Phe Gly Lys Gln Gly Thr Gly Arg Asp Asn Val Asp
            325                 330                 335
Ala Asp Lys Val Met Ile Thr Asn Glu Glu Glu Ile Lys Thr Thr Asn
            340                 345                 350
Pro Val Ala Thr Glu Ser Tyr Gly Gln Val Ala Thr Asn His Gln Ser
            355                 360                 365
Ala Gln Ala Gln Ala Gln Thr Gly Trp Val Gln Asn Gln Gly Ile Leu
            370                 375                 380
Pro Gly Met Val Trp Gln Asp Arg Asp Val Tyr Leu Gln Gly Pro Ile
385                 390                 395                 400
Trp Ala Lys Ile Pro His Thr Asp Gly Asn Phe His Pro Ser Pro Leu
            405                 410                 415
Met Gly Gly Phe Gly Met Lys His Pro Pro Gln Ile Leu Ile Lys
            420                 425                 430
Asn Thr Pro Val Pro Ala Asp Pro Pro Thr Ala Phe Asn Lys Asp Lys
            435                 440                 445
Leu Asn Ser Phe Ile Thr Gln Tyr Ser Thr Gly Gln Val Ser Val Glu
            450                 455                 460
Ile Glu Trp Glu Leu Gln Lys Glu Asn Ser Lys Arg Trp Asn Pro Glu
465                 470                 475                 480
Ile Gln Tyr Thr Ser Asn Tyr Tyr Lys Ser Asn Asn Val Glu Phe Ala
            485                 490                 495
Val Asn Thr Glu Gly Val Tyr Ser Glu Pro Arg Pro Ile Gly Thr Arg
            500                 505                 510
Tyr Leu Thr Arg Asn Leu
            515

<210> SEQ ID NO 16
<211> LENGTH: 533
<212> TYPE: PRT
<213> ORGANISM: Artificial Sequence
<220> FEATURE:
<223> OTHER INFORMATION: Description of Artificial Sequence: Synthetic
      AAV2 VP3 sequence
```

<400> SEQUENCE: 16

Met Ala Thr Gly Ser Gly Ala Pro Met Ala Asp Asn Asn Glu Gly Ala
1               5                   10                  15

Asp Gly Val Gly Asn Ser Ser Gly Asn Trp His Cys Asp Ser Thr Trp
            20                  25                  30

Met Gly Asp Arg Val Ile Thr Thr Ser Thr Arg Thr Trp Ala Leu Pro
        35                  40                  45

Thr Tyr Asn Asn His Leu Tyr Lys Gln Ile Ser Ser Gln Ser Gly Ala
    50                  55                  60

Ser Asn Asp Asn His Tyr Phe Gly Tyr Ser Thr Pro Trp Gly Tyr Phe
65                  70                  75                  80

Asp Phe Asn Arg Phe His Cys His Phe Ser Pro Arg Asp Trp Gln Arg
                85                  90                  95

Leu Ile Asn Asn Asn Trp Gly Phe Arg Pro Lys Arg Leu Asn Phe Lys
            100                 105                 110

Leu Phe Asn Ile Gln Val Lys Glu Val Thr Gln Asn Asp Gly Thr Thr
        115                 120                 125

Thr Ile Ala Asn Asn Leu Thr Ser Thr Val Gln Val Phe Thr Asp Ser
    130                 135                 140

Glu Tyr Gln Leu Pro Tyr Val Leu Gly Ser Ala His Gln Gly Cys Leu
145                 150                 155                 160

Pro Pro Phe Pro Ala Asp Val Phe Met Val Pro Gln Tyr Gly Tyr Leu
                165                 170                 175

Thr Leu Asn Asn Gly Ser Gln Ala Val Gly Arg Ser Ser Phe Tyr Cys
            180                 185                 190

Leu Glu Tyr Phe Pro Ser Gln Met Leu Arg Thr Gly Asn Asn Phe Thr
        195                 200                 205

Phe Ser Tyr Thr Phe Glu Asp Val Pro Phe His Ser Ser Tyr Ala His
    210                 215                 220

Ser Gln Ser Leu Asp Arg Leu Met Asn Pro Leu Ile Asp Gln Tyr Leu
225                 230                 235                 240

Tyr Tyr Leu Ser Arg Thr Asn Thr Pro Ser Gly Thr Thr Thr Gln Ser
                245                 250                 255

Arg Leu Gln Phe Ser Gln Ala Gly Ala Ser Asp Ile Arg Asp Gln Ser
            260                 265                 270

Arg Asn Trp Leu Pro Gly Pro Cys Tyr Arg Gln Gln Arg Val Ser Lys
        275                 280                 285

Thr Ser Ala Asp Asn Asn Asn Ser Glu Tyr Ser Trp Thr Gly Ala Thr
    290                 295                 300

Lys Tyr His Leu Asn Gly Arg Asp Ser Leu Val Asn Pro Gly Pro Ala
305                 310                 315                 320

Met Ala Ser His Lys Asp Asp Glu Glu Lys Phe Phe Pro Gln Ser Gly
                325                 330                 335

Val Leu Ile Phe Gly Lys Gln Gly Ser Glu Lys Thr Asn Val Asp Ile
            340                 345                 350

Glu Lys Val Met Ile Thr Asp Glu Glu Glu Ile Arg Thr Thr Asn Pro
        355                 360                 365

Val Ala Thr Glu Gln Tyr Gly Ser Val Ser Thr Asn Leu Gln Arg Gly
    370                 375                 380

Asn Arg Gln Ala Ala Thr Ala Asp Val Asn Thr Gln Gly Val Leu Pro
385                 390                 395                 400

Gly Met Val Trp Gln Asp Arg Asp Val Tyr Leu Gln Gly Pro Ile Trp

```
            405                 410                 415
Ala Lys Ile Pro His Thr Asp Gly His Phe His Pro Ser Pro Leu Met
        420                 425                 430

Gly Gly Phe Gly Leu Lys His Pro Pro Gln Ile Leu Ile Lys Asn
            435                 440                 445

Thr Pro Val Pro Ala Asn Pro Ser Thr Thr Phe Ser Ala Ala Lys Phe
    450                 455                 460

Ala Ser Phe Ile Thr Gln Tyr Ser Thr Gly Gln Val Ser Val Glu Ile
465                 470                 475                 480

Glu Trp Glu Leu Gln Lys Glu Asn Ser Lys Arg Trp Asn Pro Glu Ile
                485                 490                 495

Gln Tyr Thr Ser Asn Tyr Asn Lys Ser Val Asn Val Asp Phe Thr Val
            500                 505                 510

Asp Thr Asn Gly Val Tyr Ser Glu Pro Arg Pro Ile Gly Thr Arg Tyr
            515                 520                 525

Leu Thr Arg Asn Leu
    530
```

<210> SEQ ID NO 17
<211> LENGTH: 533
<212> TYPE: PRT
<213> ORGANISM: Artificial Sequence
<220> FEATURE:
<223> OTHER INFORMATION: Description of Artificial Sequence: Synthetic
      AAV9 VP3 sequence

<400> SEQUENCE: 17

```
Met Ala Thr Gly Ser Gly Ala Pro Met Ala Asp Asn Asn Glu Gly Ala
1               5                   10                  15

Asp Gly Val Gly Asn Ser Ser Gly Asn Trp His Cys Asp Ser Thr Trp
            20                  25                  30

Met Gly Asp Arg Val Ile Thr Thr Ser Thr Arg Thr Trp Ala Leu Pro
        35                  40                  45

Thr Tyr Asn Asn His Leu Tyr Lys Gln Ile Ser Ser Gln Ser Gly Ala
    50                  55                  60

Ser Asn Asp Asn His Tyr Phe Gly Tyr Ser Thr Pro Trp Gly Tyr Phe
65                  70                  75                  80

Asp Phe Asn Arg Phe His Cys His Phe Ser Pro Arg Asp Trp Gln Arg
                85                  90                  95

Leu Ile Asn Asn Asn Trp Gly Phe Arg Pro Lys Arg Leu Asn Phe Lys
            100                 105                 110

Leu Phe Asn Ile Gln Val Lys Glu Val Thr Gln Asn Asp Gly Thr Thr
        115                 120                 125

Thr Ile Ala Asn Asn Leu Thr Ser Thr Val Gln Val Phe Thr Asp Ser
    130                 135                 140

Glu Tyr Gln Leu Pro Tyr Val Leu Gly Ser Ala His Gln Gly Cys Leu
145                 150                 155                 160

Pro Pro Phe Pro Ala Asp Val Phe Met Val Pro Gln Tyr Gly Tyr Leu
                165                 170                 175

Thr Leu Asn Asn Gly Ser Gln Ala Val Gly Arg Ser Ser Phe Tyr Cys
            180                 185                 190

Leu Glu Tyr Phe Pro Ser Gln Met Leu Arg Thr Gly Asn Asn Phe Thr
        195                 200                 205

Phe Ser Tyr Thr Phe Glu Asp Val Pro Phe His Ser Ser Tyr Ala His
    210                 215                 220
```

Ser Gln Ser Leu Asp Arg Leu Met Asn Pro Leu Ile Asp Gln Tyr Leu
225                 230                 235                 240

Tyr Tyr Leu Ser Arg Thr Asn Thr Pro Ser Gly Thr Thr Gln Ser
            245                 250                 255

Arg Leu Gln Phe Ser Gln Ala Gly Ala Ser Asp Ile Arg Asp Gln Ser
            260                 265                 270

Arg Asn Trp Leu Pro Gly Pro Cys Tyr Arg Gln Gln Arg Val Ser Lys
        275                 280                 285

Thr Ser Ala Asp Asn Asn Asn Ser Glu Tyr Ser Trp Thr Gly Ala Thr
290                 295                 300

Lys Tyr His Leu Asn Gly Arg Asp Ser Leu Val Asn Pro Gly Pro Ala
305                 310                 315                 320

Met Ala Ser His Lys Asp Asp Glu Glu Lys Phe Phe Pro Gln Ser Gly
            325                 330                 335

Val Leu Ile Phe Gly Lys Gln Gly Ser Glu Lys Thr Asn Val Asp Ile
            340                 345                 350

Glu Lys Val Met Ile Thr Asp Glu Glu Ile Arg Thr Thr Asn Pro
        355                 360                 365

Val Ala Thr Glu Gln Tyr Gly Ser Val Ser Thr Asn Leu Gln Arg Gly
370                 375                 380

Asn Arg Gln Ala Ala Thr Ala Asp Val Asn Thr Gln Gly Val Leu Pro
385                 390                 395                 400

Gly Met Val Trp Gln Asp Arg Asp Val Tyr Leu Gln Gly Pro Ile Trp
            405                 410                 415

Ala Lys Ile Pro His Thr Asp Gly His Phe His Pro Ser Pro Leu Met
            420                 425                 430

Gly Gly Phe Gly Leu Lys His Pro Pro Gln Ile Leu Ile Lys Asn
        435                 440                 445

Thr Pro Val Pro Ala Asn Pro Ser Thr Thr Phe Ser Ala Ala Lys Phe
        450                 455                 460

Ala Ser Phe Ile Thr Gln Tyr Ser Thr Gly Gln Val Ser Val Glu Ile
465                 470                 475                 480

Glu Trp Glu Leu Gln Lys Glu Asn Ser Lys Arg Trp Asn Pro Glu Ile
            485                 490                 495

Gln Tyr Thr Ser Asn Tyr Asn Lys Ser Val Asn Val Asp Phe Thr Val
            500                 505                 510

Asp Thr Asn Gly Val Tyr Ser Glu Pro Arg Pro Ile Gly Thr Arg Tyr
            515                 520                 525

Leu Thr Arg Asn Leu
        530

<210> SEQ ID NO 18
<211> LENGTH: 621
<212> TYPE: PRT
<213> ORGANISM: Artificial Sequence
<220> FEATURE:
<223> OTHER INFORMATION: Description of Artificial Sequence: Synthetic
      AAV2 Rep78 sequence

<400> SEQUENCE: 18

Met Pro Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
        35                  40                  45

```
Glu Gln Ala Pro Leu Thr Val Ala Glu Lys Leu Gln Arg Asp Phe Leu
 50                  55                  60

Thr Glu Trp Arg Arg Val Ser Lys Ala Pro Glu Ala Leu Phe Phe Val
 65                  70                  75                  80

Gln Phe Glu Lys Gly Glu Ser Tyr Phe His Met His Val Leu Val Glu
                 85                  90                  95

Thr Thr Gly Val Lys Ser Met Val Leu Gly Arg Phe Leu Ser Gln Ile
                100                 105                 110

Arg Glu Lys Leu Ile Gln Arg Ile Tyr Arg Gly Ile Glu Pro Thr Leu
            115                 120                 125

Pro Asn Trp Phe Ala Val Thr Lys Thr Arg Asn Gly Ala Gly Gly Gly
130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Gln Tyr Leu
                165                 170                 175

Ser Ala Cys Leu Asn Leu Thr Glu Arg Lys Arg Leu Val Ala Gln His
            180                 185                 190

Leu Thr His Val Ser Gln Thr Gln Glu Gln Asn Lys Glu Asn Gln Asn
            195                 200                 205

Pro Asn Ser Asp Ala Pro Val Ile Arg Ser Lys Thr Ser Ala Arg Tyr
210                 215                 220

Met Glu Leu Val Gly Trp Leu Val Asp Lys Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Gly Lys
            260                 265                 270

Ile Met Ser Leu Thr Lys Thr Ala Pro Asp Tyr Leu Val Gly Gln Gln
            275                 280                 285

Pro Val Glu Asp Ile Ser Ser Asn Arg Ile Tyr Lys Ile Leu Glu Leu
290                 295                 300

Asn Gly Tyr Asp Pro Gln Tyr Ala Ala Ser Val Phe Leu Gly Trp Ala
305                 310                 315                 320

Thr Lys Lys Phe Gly Lys Arg Asn Thr Ile Trp Leu Phe Gly Pro Ala
                325                 330                 335

Thr Thr Gly Lys Thr Asn Ile Ala Glu Ala Ile Ala His Thr Val Pro
            340                 345                 350

Phe Tyr Gly Cys Val Asn Trp Thr Asn Glu Asn Phe Pro Phe Asn Asp
            355                 360                 365

Cys Val Asp Lys Met Val Ile Trp Trp Glu Glu Gly Lys Met Thr Ala
370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
                405                 410                 415

Ile Val Thr Ser Asn Thr Asn Met Cys Ala Val Ile Asp Gly Asn Ser
            420                 425                 430

Thr Thr Phe Glu His Gln Gln Pro Leu Gln Asp Arg Met Phe Lys Phe
            435                 440                 445

Glu Leu Thr Arg Arg Leu Asp His Asp Phe Gly Lys Val Thr Lys Gln
450                 455                 460
```

```
Glu Val Lys Asp Phe Phe Arg Trp Ala Lys Asp His Val Val Glu Val
465                 470                 475                 480

Glu His Glu Phe Tyr Val Lys Lys Gly Gly Ala Lys Lys Arg Pro Ala
                485                 490                 495

Pro Ser Asp Ala Asp Ile Ser Glu Pro Lys Arg Val Arg Glu Ser Val
            500                 505                 510

Ala Gln Pro Ser Thr Ser Asp Ala Glu Ala Ser Ile Asn Tyr Ala Asp
        515                 520                 525

Arg Tyr Gln Asn Lys Cys Ser Arg His Val Gly Met Asn Leu Met Leu
    530                 535                 540

Phe Pro Cys Arg Gln Cys Glu Arg Met Asn Gln Asn Ser Asn Ile Cys
545                 550                 555                 560

Phe Thr His Gly Gln Lys Asp Cys Leu Glu Cys Phe Pro Val Ser Glu
                565                 570                 575

Ser Gln Pro Val Ser Val Val Lys Lys Ala Tyr Gln Lys Leu Cys Tyr
            580                 585                 590

Ile His His Ile Met Gly Lys Val Pro Asp Ala Cys Thr Ala Cys Asp
        595                 600                 605

Leu Val Asn Val Asp Leu Asp Asp Cys Ile Phe Glu Gln
    610                 615                 620
```

<210> SEQ ID NO 19
<211> LENGTH: 536
<212> TYPE: PRT
<213> ORGANISM: Artificial Sequence
<220> FEATURE:
<223> OTHER INFORMATION: Description of Artificial Sequence: Synthetic
      AAV2 Rep68 sequence

<400> SEQUENCE: 19

```
Met Pro Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Asp Phe Leu
    50                  55                  60

Thr Glu Trp Arg Arg Val Ser Lys Ala Pro Glu Ala Leu Phe Phe Val
65                  70                  75                  80

Gln Phe Glu Lys Gly Glu Ser Tyr Phe His Met His Val Leu Val Glu
                85                  90                  95

Thr Thr Gly Val Lys Ser Met Val Leu Gly Arg Phe Leu Ser Gln Ile
            100                 105                 110

Arg Glu Lys Leu Ile Gln Arg Ile Tyr Arg Gly Ile Glu Pro Thr Leu
        115                 120                 125

Pro Asn Trp Phe Ala Val Thr Lys Thr Arg Asn Gly Ala Gly Gly Gly
    130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Gln Tyr Leu
                165                 170                 175

Ser Ala Cys Leu Asn Leu Thr Glu Arg Lys Arg Leu Val Ala Gln His
            180                 185                 190

Leu Thr His Val Ser Gln Thr Gln Glu Gln Asn Lys Glu Asn Gln Asn
        195                 200                 205
```

```
Pro Asn Ser Asp Ala Pro Val Ile Arg Ser Lys Thr Ser Ala Arg Tyr
    210                 215                 220

Met Glu Leu Val Gly Trp Leu Val Asp Lys Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Gly Lys
            260                 265                 270

Ile Met Ser Leu Thr Lys Thr Ala Pro Asp Tyr Leu Val Gly Gln Gln
        275                 280                 285

Pro Val Glu Asp Ile Ser Ser Asn Arg Ile Tyr Lys Ile Leu Glu Leu
    290                 295                 300

Asn Gly Tyr Asp Pro Gln Tyr Ala Ala Ser Val Phe Leu Gly Trp Ala
305                 310                 315                 320

Thr Lys Lys Phe Gly Lys Arg Asn Thr Ile Trp Leu Phe Gly Pro Ala
                325                 330                 335

Thr Thr Gly Lys Thr Asn Ile Ala Glu Ala Ile Ala His Thr Val Pro
            340                 345                 350

Phe Tyr Gly Cys Val Asn Trp Thr Asn Glu Asn Phe Pro Phe Asn Asp
        355                 360                 365

Cys Val Asp Lys Met Val Ile Trp Trp Glu Glu Gly Lys Met Thr Ala
    370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
                405                 410                 415

Ile Val Thr Ser Asn Thr Asn Met Cys Ala Val Ile Asp Gly Asn Ser
            420                 425                 430

Thr Thr Phe Glu His Gln Gln Pro Leu Gln Asp Arg Met Phe Lys Phe
        435                 440                 445

Glu Leu Thr Arg Arg Leu Asp His Asp Phe Gly Lys Val Thr Lys Gln
    450                 455                 460

Glu Val Lys Asp Phe Phe Arg Trp Ala Lys Asp His Val Val Glu Val
465                 470                 475                 480

Glu His Glu Phe Tyr Val Lys Lys Gly Gly Ala Lys Lys Arg Pro Ala
                485                 490                 495

Pro Ser Asp Ala Asp Ile Ser Glu Pro Lys Arg Val Arg Glu Ser Val
            500                 505                 510

Ala Gln Pro Ser Thr Ser Asp Ala Glu Ala Ser Ile Asn Tyr Ala Asp
        515                 520                 525

Arg Leu Ala Arg Gly His Ser Leu
    530                 535

<210> SEQ ID NO 20
<211> LENGTH: 397
<212> TYPE: PRT
<213> ORGANISM: Artificial Sequence
<220> FEATURE:
<223> OTHER INFORMATION: Description of Artificial Sequence: Synthetic
      AAV2 Rep52 sequence

<400> SEQUENCE: 20

Met Glu Leu Val Gly Trp Leu Val Asp Lys Gly Ile Thr Ser Glu Lys
1               5                   10                  15

Gln Trp Ile Gln Glu Asp Gln Ala Ser Tyr Ile Ser Phe Asn Ala Ala
```

```
                    20                  25                  30
Ser Asn Ser Arg Ser Gln Ile Lys Ala Ala Leu Asp Asn Ala Gly Lys
            35                  40                  45

Ile Met Ser Leu Thr Lys Thr Ala Pro Asp Tyr Leu Val Gly Gln Gln
50                  55                  60

Pro Val Glu Asp Ile Ser Ser Asn Arg Ile Tyr Lys Ile Leu Glu Leu
65                  70                  75                  80

Asn Gly Tyr Asp Pro Gln Tyr Ala Ala Ser Val Phe Leu Gly Trp Ala
                85                  90                  95

Thr Lys Lys Phe Gly Lys Arg Asn Thr Ile Trp Leu Phe Gly Pro Ala
            100                 105                 110

Thr Thr Gly Lys Thr Asn Ile Ala Glu Ala Ile Ala His Thr Val Pro
        115                 120                 125

Phe Tyr Gly Cys Val Asn Trp Thr Asn Glu Asn Phe Pro Phe Asn Asp
            130                 135                 140

Cys Val Asp Lys Met Val Ile Trp Trp Glu Glu Gly Lys Met Thr Ala
145                 150                 155                 160

Lys Val Val Glu Ser Ala Lys Ala Ile Leu Gly Gly Ser Lys Val Arg
                165                 170                 175

Val Asp Gln Lys Cys Lys Ser Ser Ala Gln Ile Asp Pro Thr Pro Val
            180                 185                 190

Ile Val Thr Ser Asn Thr Asn Met Cys Ala Val Ile Asp Gly Asn Ser
        195                 200                 205

Thr Thr Phe Glu His Gln Gln Pro Leu Gln Asp Arg Met Phe Lys Phe
    210                 215                 220

Glu Leu Thr Arg Arg Leu Asp His Asp Phe Gly Lys Val Thr Lys Gln
225                 230                 235                 240

Glu Val Lys Asp Phe Phe Arg Trp Ala Lys Asp His Val Val Glu Val
                245                 250                 255

Glu His Glu Phe Tyr Val Lys Lys Gly Gly Ala Lys Lys Arg Pro Ala
            260                 265                 270

Pro Ser Asp Ala Asp Ile Ser Glu Pro Lys Arg Val Arg Glu Ser Val
        275                 280                 285

Ala Gln Pro Ser Thr Ser Asp Ala Glu Ala Ser Ile Asn Tyr Ala Asp
    290                 295                 300

Arg Tyr Gln Asn Lys Cys Ser Arg His Val Gly Met Asn Leu Met Leu
305                 310                 315                 320

Phe Pro Cys Arg Gln Cys Glu Arg Met Asn Gln Asn Ser Asn Ile Cys
                325                 330                 335

Phe Thr His Gly Gln Lys Asp Cys Leu Glu Cys Phe Pro Val Ser Glu
            340                 345                 350

Ser Gln Pro Val Ser Val Val Lys Ala Tyr Gln Lys Leu Cys Tyr
        355                 360                 365

Ile His His Ile Met Gly Lys Val Pro Asp Ala Cys Thr Ala Cys Asp
    370                 375                 380

Leu Val Asn Val Asp Leu Asp Asp Cys Ile Phe Glu Gln
385                 390                 395

<210> SEQ ID NO 21
<211> LENGTH: 312
<212> TYPE: PRT
<213> ORGANISM: Artificial Sequence
<220> FEATURE:
<223> OTHER INFORMATION: Description of Artificial Sequence: Synthetic
      AAV2 Rep40 sequence
```

<400> SEQUENCE: 21

| | | | | | | | | | | | | | | |
|---|---|---|---|---|---|---|---|---|---|---|---|---|---|---|
|Met|Glu|Leu|Val|Gly|Trp|Leu|Val|Asp|Lys|Gly|Ile|Thr|Ser|Glu|Lys
1| | | |5| | | | |10| | | | |15|

Met Glu Leu Val Gly Trp Leu Val Asp Lys Gly Ile Thr Ser Glu Lys
1               5                   10                  15

Gln Trp Ile Gln Glu Asp Gln Ala Ser Tyr Ile Ser Phe Asn Ala Ala
            20                  25                  30

Ser Asn Ser Arg Ser Gln Ile Lys Ala Ala Leu Asp Asn Ala Gly Lys
        35                  40                  45

Ile Met Ser Leu Thr Lys Thr Ala Pro Asp Tyr Leu Val Gly Gln Gln
    50                  55                  60

Pro Val Glu Asp Ile Ser Ser Asn Arg Ile Tyr Lys Ile Leu Glu Leu
65                  70                  75                  80

Asn Gly Tyr Asp Pro Gln Tyr Ala Ala Ser Val Phe Leu Gly Trp Ala
                85                  90                  95

Thr Lys Lys Phe Gly Lys Arg Asn Thr Ile Trp Leu Phe Gly Pro Ala
            100                 105                 110

Thr Thr Gly Lys Thr Asn Ile Ala Glu Ala Ile Ala His Thr Val Pro
        115                 120                 125

Phe Tyr Gly Cys Val Asn Trp Thr Asn Glu Asn Phe Pro Phe Asn Asp
    130                 135                 140

Cys Val Asp Lys Met Val Ile Trp Trp Glu Glu Gly Lys Met Thr Ala
145                 150                 155                 160

Lys Val Val Glu Ser Ala Lys Ala Ile Leu Gly Gly Ser Lys Val Arg
                165                 170                 175

Val Asp Gln Lys Cys Lys Ser Ser Ala Gln Ile Asp Pro Thr Pro Val
            180                 185                 190

Ile Val Thr Ser Asn Thr Asn Met Cys Ala Val Ile Asp Gly Asn Ser
        195                 200                 205

Thr Thr Phe Glu His Gln Gln Pro Leu Gln Asp Arg Met Phe Lys Phe
    210                 215                 220

Glu Leu Thr Arg Arg Leu Asp His Asp Phe Gly Lys Val Thr Lys Gln
225                 230                 235                 240

Glu Val Lys Asp Phe Phe Arg Trp Ala Lys Asp His Val Val Glu Val
                245                 250                 255

Glu His Glu Phe Tyr Val Lys Lys Gly Gly Ala Lys Lys Arg Pro Ala
            260                 265                 270

Pro Ser Asp Ala Asp Ile Ser Glu Pro Lys Arg Val Arg Glu Ser Val
        275                 280                 285

Ala Gln Pro Ser Thr Ser Asp Ala Glu Ala Ser Ile Asn Tyr Ala Asp
    290                 295                 300

Arg Leu Ala Arg Gly His Ser Leu
305                 310

<210> SEQ ID NO 22
<211> LENGTH: 546
<212> TYPE: DNA
<213> ORGANISM: Mus musculus
<220> FEATURE:
<223> OTHER INFORMATION: MeCP2 Variable Promoter Sequence

<400> SEQUENCE: 22
gaacaacgcc aggctcctca acaggcaact ttgctacttc tacagaaaat gataataaag    60
aaatgctggt gaagtcaaat gcttatcaca atggtgaact actcagcagg gaggctctaa   120
taggcgccaa gagcctagac ttccttaagc gccagagtcc acaagggccc agttaatcct   180

```
caacattcaa atgctgccca caaaaccagc ccctctgtgc cctagccgcc tctttttttcc    240 aagtgacagt agaactccac caatccgcag ctgaatgggg tccgcctctt ttccctgcct    300
aaacagacag gaactcctgc caattgaggg cgtcaccgct aaggctccgc cccagcctgg    360
gctccacaac caatgaaggg taatctcgac aaagagcaag gggtggggcg cgggcgcgca    420
ggtgcagcag cacacaggct ggtcgggagg gcggggcgcg acgtctgccg tgcggggtcc    480
cggcatcggt tgcgcgcgcg ctccctcctc tcggagagag ggctgtggta aaacccgtcc    540
ggaaaa                                                              546

<210> SEQ ID NO 23
<211> LENGTH: 737
<212> TYPE: DNA
<213> ORGANISM: Mus musculus
<220> FEATURE:
<223> OTHER INFORMATION: MeCP2 Variable Promoter Sequence

<400> SEQUENCE: 23
tcaaaccatc tgattcaaca atgcacgacc gatctcttat gggcttggca cacaccatct     60
gcccattata aacgtctgca aagaccaagg tttgatatgt tgattttact gtcagcctta    120
agagtgcgac atctgctaat ttagtgtaat aatacaatca gtagacccctt aaaacaagt    180 cccttggctt ggaacaacgc caggctcctc aacaggcaac tttgctactt ctacagaaaa    240
tgataataaa gaaatgctgg tgaagtcaaa tgcttatcac aatggtgaac tactcagcag    300
ggaggctcta ataggcgcca agagcctaga cttccttaag cgccagagtc cacaagggcc    360
cagttaatcc tcaacattca aatgctgccc acaaaaccag cccctctgtg ccctagccgc    420
ctcttttttc caagtgacag tagaactcca ccaatccgca gctgaatggg gtccgcctct    480
tttccctgcc taaacagaca ggaactcctg ccaattgagg gcgtcaccgc taaggctccg    540
ccccagcctg gctccacaa ccaatgaagg gtaatctcga caaagagcaa ggggtggggc    600
gcgggcgcgc aggtgcagca gcacacaggc tggtcgggag gcggggcgc gacgtctgcc    660 gtgcggggtc ccggcatcgg ttgcgcgcgc gctccctcct ctcggagaga ggctgtggt    720 aaaacccgtc cggaaaa                                                 737

<210> SEQ ID NO 24
<211> LENGTH: 556
<212> TYPE: DNA
<213> ORGANISM: Artificial Sequence
<220> FEATURE:
<223> OTHER INFORMATION: Description of Artificial Sequence: Synthetic
      CBA promoter with CMV enhancer sequence

<400> SEQUENCE: 24
cgttacataa cttacggtaa atggcccgcc tggctgaccg cccaacgacc cccgcccatt     60
gacgtcaata atgacgtatg ttcccatagt aacgccaata gggactttcc attgacgtca    120
atgggtggag tatttacggt aaactgccca cttggcagta catcaagtgt atcatatgcc    180
aagtacgccc cctattgacg tcaatgacgg taaatggccc gcctggcatt atgcccagta    240
catgacctta tgggactttc ctacttggca gtacatctac tcgaggccac gttctgcttc    300
actctcccca tctccccccc ctccccaccc ccaattttgt atttatttat tttttaatta    360
ttttgtgcag cgatggggc gggggggggg ggggggcgcg cgccaggcgg ggcggggcgg    420
ggcgaggggc gggcgggc gaggcggaga ggtgcggcgg cagccaatca gagcggcgcg    480
ctccgaaagt ttccttttat ggcgaggcgg cggcggcgg ggccctataa aaagcgaagc    540
```
gcgcggcggg cgggag                                                 556

<210> SEQ ID NO 25
<211> LENGTH: 2280
<212> TYPE: DNA
<213> ORGANISM: Artificial Sequence
<220> FEATURE:
<223> OTHER INFORMATION: Description of Artificial Sequence: Synthetic
      Neurofilament light-chain gene promoter sequence

<400> SEQUENCE: 25

| | | | | | |
|---|---|---|---|---|---|
| gtaaatacta | agagtgtttt | atgcagactc | acacacacta | agtgtggaac | aatgaggttt | 60 |
| gcagggagca | ggttaacaaa | ataatccatt | ctgccatgct | tcatctacat | atgggtaatt | 120 |
| gggaggagac | aactctatgg | cttatctggg | tccttgttcc | accctccgcc | tccagagaag | 180 |
| cctattccac | ccttgaattt | catgagtgaa | aagaccaagg | atagctaggc | tatgaaaagt | 240 |
| caacagagta | agtaccctac | caaacctgcc | agggacaaac | aatattcagg | acagcctcat | 300 |
| gaccttaggc | ttaaaatcta | caatatttgg | gcatggatgg | tcctctgaga | tcacttagtc | 360 |
| ttgatagatt | taaactacta | attttcaata | tttgtgaatt | tgcattattt | gcgacaacag | 420 |
| acattgttta | gaaacctgag | gaaagttatc | tgctgcagtc | tatcatgagg | acggtgggct | 480 |
| atcacaatca | caggtatttt | ttttgggggg | ggggatgaga | aagggcctct | gaagataagc | 540 |
| ctcaccccat | cctttcctcg | ggagagagtg | aaatgtctcc | agaagcaact | gcaccactgc | 600 |
| aaatacttca | ccctccaagt | atcacagggg | aagccattcc | gggcttctct | atttgaaaac | 660 |
| aattaccata | ttccccctca | gtttgcctct | taaaaaaaac | ataagttgca | caatcaaatg | 720 |
| ctgcgatata | caaataaaac | aaaaactaaa | tgcttgctca | gataaatctt | aggtgtttcg | 780 |
| tgtaaatctc | tgcaatccct | ccatgaaacc | tggggactc | ctaacatcat | gcgtgtgaaa | 840 |
| atgccctgca | aaccgtaggg | ttgtatccac | gtgcgctacc | gcgtgcgcca | gtttcaagca | 900 |
| tctgggtgct | tcctgaagga | aatccatgca | ttcctgactg | catctgtttt | cgggttatta | 960 |
| cattgtatcg | gggaagagtc | acgcggctat | ggctattttc | tatccgttcc | tgaagaagcc | 1020 |
| tgggtgccga | gttctcctcc | ccagagacca | cacccagcgc | ttagggctgg | ccgcagcggc | 1080 |
| ttccctgaaa | atcagccaac | tgcaaggctt | atcgaaatca | tcaggtcgtg | tgctacacat | 1140 |
| gtgtaaaaag | aggaaagcgg | acttaaatg | tgctgcggtt | ggtggtagca | agcaggaatt | 1200 |
| tagcttggtg | aggatccagg | cagcttgaag | ctcccggctg | cggacgcgcg | gctccctcag | 1260 |
| caagtcagtc | tctgtgtttc | caactctttc | tctgccctca | ccaccacac | actgcaacac | 1320 |
| gttaaagcca | tctgcggctt | cattctcagt | taagaaatgt | gaaaatctag | aaacactaac | 1380 |
| aggcggatta | actgctgtaa | gggtttaaaa | atgctaaacc | aatacctgca | gtagtgccgc | 1440 |
| agtttcacga | gtgtgtgtgt | gtgtgtgtgt | gtgcgcgcgc | gcgcatcgcg | cgacactccc | 1500 |
| tatgtgttaa | gcagctcatt | aaagaaaaag | aaaaataatc | aggagaaagg | aagatgaatt | 1560 |
| acagaaagtg | ccagaaagct | agaaagaaat | taaaactctt | ctccatacat | actgcataca | 1620 |
| cataacctag | cctatttatt | tgtatctaaa | attccctagc | cgcaccatca | ccgtaaacac | 1680 |
| caagggaaaa | aattaaggag | gttcctggtg | ggaaagggc | gagttggggg | gacagggtgt | 1740 |
| ctgcgaggtg | acgggataca | caaaactagg | gtgtcaaaag | ggagcaagaa | cctgttttga | 1800 |
| gggcaactta | aggatccaag | tgtcacgggg | tctgggcaat | gaaggacggg | aggggctgcg | 1860 |
| tgagtgagta | cagaagggaa | atgagtgagg | gggcatggga | tctcagagaa | aatcagggcc | 1920 |
| ctctgagcaa | agtggaaagg | acgaccgccg | cagctcctcg | ggccgtagcc | cgaccccgcc | 1980 |

| | |
|---|---|
| ttcccttttg cgcagaatcc tcgccttggc tgcagcagcg cgctgccccc actggccggc | 2040 |
| gtgccgtgat cgatcgcagg ctgcgtcagg acctcccggc gtataaatag gggtggcaga | 2100 |
| acggcgccga gccgcacaca accatccatc ctccccttc cctctctccc ctgtcctctc | 2160 |
| tctccgggct cccaccgccg ccgcgggccg gggagcaccg gccgccacca tgagttcctt | 2220 |
| cagctacgag ccgtactact cgacctccta caagcggcgc tacgtggaga cgccccgggt | 2280 |

<210> SEQ ID NO 26
<211> LENGTH: 2356
<212> TYPE: DNA
<213> ORGANISM: Artificial Sequence
<220> FEATURE:
<223> OTHER INFORMATION: Description of Artificial Sequence: Synthetic
  Neuron-specific vgf gene promoter sequence

<400> SEQUENCE: 26

| | |
|---|---|
| ctcgaggatc tgattaaata cacaattgct tccccccatt ccctttcttt ttctccccgc | 60 |
| cccggccatg tatctcattc atctccatac acacataaac acacatgcac aagccatgta | 120 |
| catgtacacg caggtgtgtg tgcatacaca agccaacagg caaatacagt ttctccaggt | 180 |
| gcctgtcttc tctcatcttg caacttggtc tctgatcccc atcagccact cagtcagccc | 240 |
| ccttggctcc ctccctcccc tctcccttct ctcttggatg ggttcccctc cccctctcca | 300 |
| gatgtctgag ccatcttctc tctgattcat cctcctcagg aaggaacgtg accccctccc | 360 |
| catcccactg cctctgtatc aggctgggaa gatgaagggg acatgggggc ggggagagga | 420 |
| aggagggggag gccgtggtta gttgtgcgtg gggatgggag gcattgcctg gggtctccta | 480 |
| cccccctcttt tcccctccct ttctttggaa tctccactgt caccttggtt ctcagttttt | 540 |
| ttttctcctt tagcctgctc cttctacctg ttccagatcc cttcattcct tcctcctccc | 600 |
| ctgcccccat ctcttctctc ttttctccct ctccactcct cccatttct ttcccgccaa | 660 |
| gagctgatgg gctttcttct gggaaagtcg agccactgat ggaagcgaga agccactgct | 720 |
| ggttatagag agaaagcacg tgagtgtgtg tgtagggagg gggaggttag aaggagggtc | 780 |
| agtgccagga agaggtgagg aggggggga ggaccgtttc tgaaagagtc tctaagaccc | 840 |
| tgacagacag ccctgacctt ggtttccaga gtctcagggt gcggtgccct gcgtgtgccc | 900 |
| acagagcacc cctatgtccg cagttcgtgt gtgtctggcg tgtgtcattg tattcccccc | 960 |
| cccttgggtg cccaggcccg ccaccgctct ctgccagcac cgcagccccc tccaggcttc | 1020 |
| ctccctccct ccccttcatt cctgcagtgg ctgcccccct tgccaccctc tcctctcccc | 1080 |
| tgcccctcc ccatttcctg cctccccccc accgccca cggctggtct cccttgaccg | 1140 |
| gacccagctc tctgatggat tctctttgcg caaatctgtg cgtcatcgcc cccaccccg | 1200 |
| gaacctctag ctgtccaagc ccccagcccc aacctctctg gcaggagata cggtcgaagg | 1260 |
| ggctggtggc agagaggggc tatctctgac gttgcaggtc cccctcccat cgcgttcaaa | 1320 |
| ccttcccttt aagcggtgga gagagctgga gttgagtcac cccccccccc acctgcgcaa | 1380 |
| cccccctcccc acctgctctg gtctcgccct ccaaacgtcc ttggggagg ggagcgggcc | 1440 |
| aggagggaaa gcgactgggg agtgtgggaa gagatggggc cgaaggggc acagcggggg | 1500 |
| gccttgacac aagcggcagt caggggacag aaggacagac acaccttttt ctccagacac | 1560 |
| agcacggatc gtgaaacaga cacgacccag aggcacacac atcctcattc tttcccttttt | 1620 |
| ctcttccgac tcggaccctt ccgatgggat taccaaaacc gcaagatcca cccatctccg | 1680 |
| ctgtcagggg ctgcaccccg actgcccatt ccgggacagc cgcaggcgtg cagatctgtc | 1740 |

```
cctctgcact caggttcacg ccgtccttgg ggccgtggtc tcggggtggg gaaccggccc    1800
ctggtcggct cttgaatctt tatccttccc ctccccagta ttgagctccc actggtgccc    1860
agtcagacgc tgggactacc cttttctat tccactcagc aacgcgggct ccatccagca     1920
gctccaagtt gctctgcaac ccacccctcc gccttccagc gcctctgcat ccacccttcc    1980
attcattctc ccattcattc attcatcctt ttctcctcgt ccctccttca ttcattcata    2040 gcccccccgcc ctgcccgctt cagcatttca ttcattcatt cattcattca tttcccggag   2100
ctccgctagc gcacacccct tcagccgaag ccccagcgcg caggcgcagg ccgggagagg    2160
caggcaccct ccaatcgtcg ggcgtccttc ctcctccggg cggccgcccg cttccccatg    2220
aatgaacatt gacgtcaatg gggcggggcg cgcccacgtg accccgcgcg ctcccctta    2280 taaggcggtg gaggcgcggg gctgtccagc gtgctgaagc ggagcgagct agccgcccgg    2340
agccgcgccg acccag                                                    2356
```

<210> SEQ ID NO 27
<211> LENGTH: 576
<212> TYPE: DNA
<213> ORGANISM: Artificial Sequence
<220> FEATURE:
<223> OTHER INFORMATION: Description of Artificial Sequence: Synthetic
      CMV promoter sequence

<400> SEQUENCE: 27

```
tagtaatcaa ttacggggtc attagttcat agcccatata tggagttccg cgttacataa      60
cttacggtaa atggcccgcc tggctgaccg cccaacgacc cccgcccatt gacgtcaata     120
atgacgtatg ttcccatagt aacgccaata gggactttcc attgacgtca atgggtggag    180
tatttacggt aaactgccca cttggcagta catcaagtgt atcatatgcc aagtacgccc    240
cctattgacg tcaatgacgg taaatggccc gcctggcatt atgcccagta catgacctta    300
tgggactttc ctacttggca gtacatctac gtattagtca tcgctattac catggtgatg    360
cggttttggc agtacatcaa tgggcgtgga tagcggtttg actcacgggg atttccaagt    420
ctccacccca ttgacgtcaa tgggagtttg ttttggcacc aaaatcaacg ggactttcca    480
aaatgtcgta caactccgcc ccattgacgc aaatgggcg gtaggcgtgt acggtgggag     540
gtctatataa gcagagctgg tttagtgaac cgtcag                              576
```

<210> SEQ ID NO 28
<211> LENGTH: 454
<212> TYPE: DNA
<213> ORGANISM: Artificial Sequence
<220> FEATURE:
<223> OTHER INFORMATION: Description of Artificial Sequence: Synthetic
      RSV promoter sequence

<400> SEQUENCE: 28

```
cgacaattgc atgaagaatc tgcttagggt taggcgtttt gcgctgcttc gcgatgtacg      60
ggccagatat acgcgtatct gaggggacta gggtgtgttt aggcgaaaag cggggcttcg    120
gttgtacgcg gttaggagtc ccctcaggat atagtagttt cgcttttgca tagggagggg    180
gaaatgtagt cttatgcaat acacttgtag tcttgcaaca tggtaacgat gagttagcaa    240
catgccttac aaggagagaa aaagcaccgt gcatgccgat tggtggaagt aaggtggtac    300
gatcgtgcct tattaggaag gcaacagaca ggtctgacat ggattggacg aaccactgaa    360
ttgcgcattg cagagataat tgtatttaag tgcctagctc gatacaataa acgccatttg    420
accattcacc acattggtgt gcacctccaa ggcc                                454
```

<210> SEQ ID NO 29
<211> LENGTH: 350
<212> TYPE: DNA
<213> ORGANISM: Artificial Sequence
<220> FEATURE:
<223> OTHER INFORMATION: Description of Artificial Sequence: Synthetic
      SV40 promoter sequence

<400> SEQUENCE: 29

```
cagctgtgga atgtgtgtca gttagggtgt ggaaagtccc caggctcccc agcaggcaga      60
agtatgcaaa gcatgcatct caattagtca gcaaccaggc tcccagcag gcagaagtat     120
gcaaagcatg catctcaatt agtcagcaac catagtcccg cccctaactc cgcccatccc    180
gcccctaact ccgcccagtt ccgcccattc tccgccccat ggctgactaa ttttttttat    240
ttatgcagag gccgaggccg cctcggcctc tgagctattc cagaagtagt gaggaggctt    300
ttttggaggc ctaggctttt gcaaaaagct ttgcaaagat ggataaagtt               350
```

<210> SEQ ID NO 30
<211> LENGTH: 511
<212> TYPE: DNA
<213> ORGANISM: Artificial Sequence
<220> FEATURE:
<223> OTHER INFORMATION: Description of Artificial Sequence: Synthetic
      PGK promoter sequence

<400> SEQUENCE: 30

```
gatctctacc gggtagggga ggcgcttttc ccaaggcagt ctggagcatg cgctttagca     60
gccccgctgg gcacttggcg ctacacaagt ggcctctggc ctcgcacaca ttccacatcc    120
accggtaggc gccaaccggc tccgttcttt ggtggcccct tcgcgccacc ttctacccct    180
cccctagtca ggaagttccc ccccgccccg cagctcgcgt catgcaggac gtgacaaatg    240
gaagtagcac gtctcactag tctcgtgcaa atggacagca ccgctgagca atggaagcgg    300
gtaggccctt ggggcagcgg ccaatagcag ctttgctcct tcgctttctg ggctcagagg    360
ctgggaaggg gtgggtccgg gggcgggctc aggggcgggc tcaggggcgg ggcgggcgcc    420
cgaaggtcct ccggaggccc ggcattccgc acgcttcaaa agcgcacgtc tgccgcgctg    480
ttctcttctt cctcatctcc gggcctttcg a                                   511
```

<210> SEQ ID NO 31
<211> LENGTH: 1211
<212> TYPE: DNA
<213> ORGANISM: Artificial Sequence
<220> FEATURE:
<223> OTHER INFORMATION: Description of Artificial Sequence: Synthetic
      EFalpha promoter sequence

<400> SEQUENCE: 31

```
gatctcgtga ggctccggtg cccgtcagtg ggcagagcgc acatcgccca cagtccccga     60
gaagttgggg ggaggggtcg gcaattgaac cggtgcctag agaaggtggc gcggggtaaa    120
ctgggaaagt gatgtcgtgt actggctccg ccttttttccc gagggtgggg gagaaccgta   180
tataagtgca ctagtcgccg tgaacgttct ttttcgcaac gggtttgccg ccagaacaca    240
ggtaagtgcc gtgtgtggtt cccgcgggcc tggcctcttt acgggttatg gcccttgcgt    300
gccttgaatt acttccacct ggctgcagta cgtgattctt gatcccgagc ttcgggttgg    360
aagtgggtgg gagagttcgt ggccttgcgc ttaaggagcc ccttcgcctc gtgcttgagt    420
tgtggcctgg cctgggcgct ggggccgccg cgtgcgaatc tggtggcacc ttcgcgcctg    480
```

-continued

```
tctcgctgct tcgataagt ctctagccat ttaaaatttt tgatgacctg ctgcgacgct      540
ttttttctgg caagatagtc ttgtaaatgc gggccaagat cagcacactg gtatttcggt     600
ttttggggcc gcggcggcg acggggcccg tgcgtcccag cgcacatgtt cggcgaggcg      660
gggcctgcga gcgcggccac cgagaatcgg acggggtag tctcaagctg cccggcctgc      720
tctggtgcct ggcctcgcgc cgccgtgtat cgccccgccc tgggcggcaa ggctggcccg     780
gtcggcacca gttgcgtgag cggaaagatg gccgcttccc ggccctgctg cagggagcac     840
aaaatggagg acgcggcgct cgggagagcg ggcgggtgag tcacccacac aaaggaaaag     900
ggcctttccg tcctcagccg tcgcttcatg tgactccacg gagtaccggg cgccgtccag     960
gcacctcgat tagttctcca gcttttggag tacgtcgtct ttaggttggg gggaggggtt     1020
ttatgcgatg gagtttcccc acactgagtg ggtggagact gaagttaggc cagcttggca     1080
cttgatgtaa ttctccttgg aatttgccct ttttgagttt ggatcttggt tcattctcaa     1140
gcctcagaca gtggttcaaa gttttttct tccatttcag gtgtcgtgaa aactacccct     1200
aaaagccaaa a                                                          1211
```

<210> SEQ ID NO 32
<211> LENGTH: 408
<212> TYPE: DNA
<213> ORGANISM: Artificial Sequence
<220> FEATURE:
<223> OTHER INFORMATION: Description of Artificial Sequence: Synthetic
      Synapsin promoter sequence

<400> SEQUENCE: 32

```
agatctctgc agaaggccct gcgtatgagt gcaagtgggt tttaggacca ggatgaggcg     60
gggtgggggt gcctacctga cgaccgaccc cgacccactg gacaagcacc caaccccat     120 tccccaaatt gcgcatcccc tatcagagag ggggagggga acaggatgc ggcgaggcgc      180 gtgcgcactg ccagcttcag caccgcgac agtgccttcg cccccgcctg gcggcgcgcg     240
ccaccgccgc ctcagcactg aaggcgcgct gacgtcactc gccggtcccc cgcaaactcc     300
ccttcccggc caccttggtc gcgtccgcgc cgccgccggc ccagccggac cgcaccacgc     360
gaggcgcgag ataggggggc acgggcgcga ccatctgcgc tgcggcga                  408
```

<210> SEQ ID NO 33
<211> LENGTH: 336
<212> TYPE: DNA
<213> ORGANISM: Artificial Sequence
<220> FEATURE:
<223> OTHER INFORMATION: Description of Artificial Sequence: Synthetic
      NSE promoter sequence

<400> SEQUENCE: 33

```
atggcgccgg gcctttcttt atgttttgg cgtcttccat ggtggcttta ccaacagtac      60
cggaatgcca agcttactta gatcgcagat ctcggtggta gtggcggtgg cggtggcggt     120
ggcgacggcg gcgctgagag agcgggagtg gcagtggcgg cggcggctgc ggctcccggg     180
cggcgggcgg aggaggcgcc tatagggccg cgcgggcgca tgtgacccgg agcccccgat     240
gagtcaggag ctgccggcgg aggcgcacgt acgagcgcgg gtggggacc gacgagggtg     300 gagtggggaa gggaggagga tgggggaagg gtgggg                               336
```

<210> SEQ ID NO 34
<211> LENGTH: 1219
<212> TYPE: DNA

<213> ORGANISM: Artificial Sequence
<220> FEATURE:
<223> OTHER INFORMATION: Description of Artificial Sequence: Synthetic
      UBC promoter sequence

<400> SEQUENCE: 34

```
gatctggcct ccgcgccggg ttttggcgcc tcccgcgggc gccccctcg tcacggcgag      60
cgctgccacg tcagacgaag ggcgcaggag cgtcctgatc cttccgcccg gacgctcagg    120
acagcggccc gctgctcata agactcggcc ttagaacccc agtatcagca aaggacatt    180
ttaggacggg acttgggtga ctctagggca ctggttttct ttccagagag cggaacaggc    240
gaggaaaagt agtcccttct cggcgattct gcggagggat ctccgtgggg cggtgaacgc    300
cgatgattat ataaggacgc gccgggtgtg gcacagctag ttccgtcgca gccgggattt    360
gggtcgcggt tcttgtttgt ggatcgctgt gatcgtcact tggtgagtag cgggctgctg    420
ggctggccgg ggctttcgtg gccgccgggc cgctcggtgg gacggaagcg tgtggagaga    480
ccgccaaggg ctgtagtctg ggtccgcgag caaggttgcc ctgaactggg ggttgggggg    540
agcgcagcaa aatggcggct gttcccgagt cttgaatgga agacgcttgt gaggcgggct    600
gtgaggtcgt tgaaacaagg tgggggggcat ggtgggcggc aagaacccaa ggtcttgagc    660
ccttcgctaa tgcgggaaag ctcttattcg ggtgagatgg gctgggcacc atctggggac    720
cctgacgtga agtttgtcac tgactggaga actcggtttg tcgtctgttg cgggggcggc    780
agttatggcg gtgccgttgg gcagtgcacc cgtaccttg ggagcgcgcg ccctcgtcgt    840
gtcgtgacgt cacccgttct gttggcttat aatgcagggt ggggccacct gccggtaggt    900
gtgcggtagg cttttctccg tcgcaggacg cagggttcgg gcctaggggta ggctctcctg    960
aatcgacagg cgccggacct ctggtgaggg gagggataag tgaggcgtca gtttctttgg   1020
tcggttttat gtacctatct tcttaagtag ctgaagctcc ggttttgaac tatgcgctcg   1080
gggttggcga gtgtgttttg tgaagttttt taggcaccctt ttgaaatgta atcatttggg   1140
tcaatatgta attttcagtg ttagacttgt aaattgtccg ctaaattctg gccgtttttg   1200
gcttttttgt tagacaaca                                                1219
```

<210> SEQ ID NO 35
<211> LENGTH: 738
<212> TYPE: PRT
<213> ORGANISM: Adeno-associated virus
<220> FEATURE:
<223> OTHER INFORMATION: AAV 8

<400> SEQUENCE: 35

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110
```

```
Asn Leu Gly Arg Ala Val Phe Gln Ala Lys Lys Arg Val Leu Glu Pro
            115                 120                 125

Leu Gly Leu Val Glu Glu Gly Ala Lys Thr Ala Pro Gly Lys Lys Arg
        130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ala Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
        290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Thr Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Thr Thr Gly Gly Thr Ala Asn Thr Gln Thr Leu Gly
450                 455                 460

Phe Ser Gln Gly Gly Pro Asn Thr Met Ala Asn Gln Ala Lys Asn Trp
465                 470                 475                 480

Leu Pro Gly Pro Cys Tyr Arg Gln Gln Arg Val Ser Thr Thr Thr Gly
                485                 490                 495

Gln Asn Asn Asn Ser Asn Phe Ala Trp Thr Ala Gly Thr Lys Tyr His
            500                 505                 510

Leu Asn Gly Arg Asn Ser Leu Ala Asn Pro Gly Ile Ala Met Ala Thr
        515                 520                 525
```

```
His Lys Asp Asp Glu Glu Arg Phe Phe Pro Ser Asn Gly Ile Leu Ile
    530                 535                 540

Phe Gly Lys Gln Asn Ala Ala Arg Asp Asn Ala Asp Tyr Ser Asp Val
545                 550                 555                 560

Met Leu Thr Ser Glu Glu Glu Ile Lys Thr Thr Asn Pro Val Ala Thr
                565                 570                 575

Glu Glu Tyr Gly Ile Val Ala Asp Asn Leu Gln Gln Gln Asn Thr Ala
            580                 585                 590

Pro Gln Ile Gly Thr Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Asn Gln Ser Lys Leu Asn Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Ser Val Asp Phe Ala Val Asn Thr Glu
705                 710                 715                 720

Gly Val Tyr Ser Gly Pro Arg Pro Ile Gly Thr Arg Tyr Leu Thr Arg
                725                 730                 735

Asn Leu

<210> SEQ ID NO 36
<211> LENGTH: 1877
<212> TYPE: DNA
<213> ORGANISM: Adeno-associated virus
<220> FEATURE:
<223> OTHER INFORMATION: AAV 9

<400> SEQUENCE: 36
ctggttgagg aaggcgctaa gacggctcct ggaaagaaga gaccggtaga gcagtcaccc    60
caagaaccag actcatcctc gggcatcggc aaatcaggcc agcagcccgc taaaagaga   120 ctcaattttg gtcagactgg cgactcagag tcagtccccg acccacaacc tctcggagaa   180
cctccagaag cccccctcagg tctgggacct aatacaatgg cttcaggcgg tggcgctcca   240
atggcagaca taacgaaggc gccgacgga gtgggtaatt cctcgggaaa ttggcattgc   300
gattccacat ggctggggga cagagtcatc accaccagca cccgaacctg gcattgccc   360 acctacaaca accacctcta caagcaaatc tccaatggaa catcgggagg aagcaccaac   420
gacaacacct actttggcta cagcaccccc tgggggtatt ttgacttcaa cagattccac   480
tgccacttct caccacgtga ctggcagcga ctcatcaaca caactgggg attccggcca   540 aagagactca acttcaagct gttcaacatc caggtcaagg aggttacgac gaacgaaggc   600
accaagacca tcgccaataa ccttaccagc accgtccagg tctttacgga ctcggagtac   660
cagctaccgt acgtcctagg ctctgcccac caaggatgcc tgccaccgtt tcctgcagac   720
gtcttcatgg ttcctcagta cggctacctg acgctcaaca atggaagtca agcgttagga   780
cgttcttctt tctactgtct ggaatacttc ccttctcaga tgctgagaac cggcaacaac   840
```

```
tttcagttca gctacacttt cgaggacgtg cctttccaca gcagctacgc acacagccag    900
agtctagatc gactgatgaa cccctcatc gaccagtacc tatactacct ggtcagaaca     960
cagacaactg gaactggggg aactcaaact ttggcattca gccaagcagg ccctagctca   1020
atggccaatc aggctagaaa ctgggtaccc gggccttgct accgtcagca gcgcgtctcc   1080
acaaccacca accaaaataa caacagcaac tttgcgtgga cgggagctgc taaattcaag   1140
ctgaacggga gagactcgct aatgaatcct ggcgtggcta tggcatcgca caaagacgac   1200
gaggaccgct tctttccatc aagtggcgtt ctcatatttg gcaagcaagg agccgggaac   1260
gatggagtcg actacagcca ggtgctgatt acagatgagg aagaaattaa agccaccaac   1320
cctgtagcca cagaggaata cggagcagtg gccatcaaca accaggccgc taacacgcag   1380
gcgcaaactg gacttgtgca taaccaggga gttattcctg gtatggtctg cagaaccgg    1440 gacgtgtacc tgcagggccc tatttgggct aaaataccct cacacagatg gcaactttcac  1500 ccgtctcctc tgatgggtgg atttggactg aaacacccac ctccacagat tctaattaaa   1560
aatacaccag tgccggcaga tcctcctctt accttcaatc aagccaagct gaactctttc   1620
atcacgcagt acagcacggg acaagtcagc gtggaaatcg agtgggagct gcagaaagaa   1680
aacagcaagc gctggaatcc agagatccag tatacttcaa actactacaa atctacaaat   1740
gtggactttg ctgtcaatac cgaaggtgtt tactctgagc ctcgccccat tggtactcgt   1800
tacctcaccc gtaatttgta attgcctgtt aatcaataaa ccggttaatt cgtttcagtt   1860
gaactttggt ctctgcg                                                  1877

<210> SEQ ID NO 37
<211> LENGTH: 597
<212> TYPE: DNA
<213> ORGANISM: Artificial Sequence
<220> FEATURE:
<223> OTHER INFORMATION: Description of Artificial Sequence: Synthetic
      WPRE enhancer sequence

<400> SEQUENCE: 37
cgataatcaa cctctggatt acaaaatttg tgaaagattg actggtattc ttaactatgt     60
tgctcctttt acgctatgtg gatacgctgc tttaatgcct ttgtatcatg ctattgcttc    120
ccgtatggct ttcattttct cctccttgta taaatcctgg ttgctgtctc tttatgagga    180
gttgtggccc gttgtcaggc aacgtggcgt ggtgtgcact gtgtttgctg acgcaacccc    240
cactggttgg ggcattgcca ccacctgtca gctcctttcc gggactttcg ctttccccct    300
ccctattgcc acggcggaac tcatcgccgc ctgccttgcc cgctgctgga caggggctcg    360
gctgttgggc actgacaatt ccgtggtgtt gtcggggaaa tcatcgtcct tccttggct    420 gctcgcctgt gttgccacct ggattctgcg cgggacgtcc ttctgctacg tcccttcggc    480
cctcaatcca gcggaccttc cttcccgcgg cctgctgccg gctctgcggc ctcttccgcg    540
tcttcgcctt cgccctcaga cgagtcggat ctccctttgg gccgcctccc cgcatcg       597

<210> SEQ ID NO 38
<211> LENGTH: 606
<212> TYPE: DNA
<213> ORGANISM: Artificial Sequence
<220> FEATURE:
<223> OTHER INFORMATION: Description of Artificial Sequence: Synthetic
      WPRE enhancer sequence

<400> SEQUENCE: 38
cgactgatcc gataatcaac ctctggatta caaaatttgt gaaagattga ctggtattct     60
```

```
taactatgtt gctccttta cgctatgtgg atacgctgct ttaatgcctt tgtatcatgc      120
tattgcttcc cgtatggctt tcattttctc ctccttgtat aaatcctggt tgctgtctct      180
ttatgaggag ttgtggcccg ttgtcaggca acgtggcgtg gtgtgcactg tgtttgctga      240
cgcaaccccc actggttggg gcattgccac cacctgtcag ctcctttccg ggactttcgc      300
tttccccctc cctattgcca cggcggaact catcgccgcc tgccttgccc gctgctggac      360
aggggctcgg ctgttgggca ctgacaattc cgtggtgttg tcggggaaat catcgtcctt      420
tccttggctg ctcgcctgtg ttgccacctg gattctgcgc gggacgtcct tctgctacgt      480
cccttcggcc ctcaatccag cggaccttcc ttcccgcggc ctgctgccgg ctctgcggcc      540
tcttccgcgt cttcgccttc gccctcagac gagtcggatc tccctttggg ccgcctcccc      600
gcatcg                                                                606
```

GENE THERAPY FOR JUVENILE BATTEN DISEASE

CROSS-REFERENCE TO RELATED APPLICATIONS

This application is a National Stage Entry of International Application No. PCT/US2015/066206, filed Dec. 16, 2015, which claims the benefit of the filing date of U.S. Provisional Patent Application No. 62/092,501, filed Dec. 16, 2014, and U.S. Provisional Patent Application No. 62/146,793, filed Apr. 13, 2015. The foregoing are incorporated by reference herein in their entireties.

SEQUENCE LISTING

The instant application contains a Sequence Listing which has been submitted electronically in ASCII format and is hereby incorporated by reference in its entirety. Said ASCII copy, created on Oct. 30, 2017, is named 060919-2011 SL.txt and is 112,930 bytes in size.

BACKGROUND

Lysosomal storage diseases are a class of metabolic disorders caused by mutations in proteins important for lysosomal function. There are many types of lysosomal storage diseases, and although each is relatively rare, their combined prevalence is estimated to be 1 in 8,000 live births (Schultz et al. (2011) *Trends Neurosci.*, 34: 401-410). Juvenile neuronal ceroid lipofuscinosis (JNCL or Juvenile Batten disease) is a fatal, neurodegenerative lysosomal storage disease appearing in about 1 in 100,000 live births that typically presents in children between the ages of 5-10 years. JNCL initiates as blindness and progresses to seizures, motor loss, and subsequent cognitive decline (Getty and Pearce (2011) *Cell. Mol. Life Sci.* 68:453-474).

Juvenile Batten Disease is caused by an autosomal recessive mutation in the CLN3 gene, most commonly due to a 1.02 kb deletion in exons 7 and 8 (Int. Batten Dis. Consortium (1995) *Cell,* 82: 949-957), and although the CLN3 protein has been shown to reside in lysosomal membranes and other membrane compartments, its function remains elusive. CLN3 has been implicated in several cellular processes including, inter alia, endocytosis and intracellular protein trafficking, lysosomal homeostasis, autophagy, mitochondrial function, amino acid transport, oxidative stress, neuronal excitotoxicity, and cell cycle regulation.

Juvenile Batten Disease is characterized by the abnormal intracellular accumulation of lipid and protein (ceroid lipofuscin) in lysosomes, resulting in the development of insoluble inclusions. Although lysosomal inclusions form in all cell types in the body, neurons are the most sensitive and undergo progressive cell death (Getty and Pearce (2011) *Cell. Mol. Life Sci.* 68:453-474). The seriousness of this neuronal cell death is magnified by the fact that the central nervous system (CNS) is not capable of regeneration. Currently, there is no treatment for Juvenile Batten Disease, which is uniformly fatal and associated with a decreased life expectancy into the late teens or early twenties.

SUMMARY

Compositions and methods for the treatment of Juvenile Neuronal Ceroid Lipofuscinosis (JNCL), also known as Juvenile Batten Disease and associated disorders and symptoms are provided herein. In certain embodiments the compositions comprise, or alternatively consist essentially of, or yet further consist of, adeno-associated viral (AAV) constructs, that in turn comprise, or alternatively consist essentially of, or yet further consist of, adeno-associated viral constructs, e.g., self-complementary or non-self-complementary adeno-associated viral (sc-AAV) constructs, that express a nucleic acid encoding human CLN3 (the human gene CLN3 (or a CLN3 cDNA)). In one illustrative, but non-limiting embodiment, an AAV-9 construct or a scAAV-9 construct is used. The AAV constructs comprise, in various embodiments, a variety of promoters and/or promoter/enhancers combinations can be used within the AAV construct to drive expression of the human-CLN3 gene or CLN3 cDNA or an equivalent of each thereof. Examples of promoters that can be used within the AAV construct include, but are not limited to, the β-actin promoter (e.g., the chicken β-actin promoter), the MeCP2 promoter, and the like. The AAV-hCLN3 constructs can be used to restore expression of wild-type CLN3 in the brain and other key tissues or organs which in turn can help treat JNCL and/or improve symptoms associated with JNCL. This gene therapy can be administered through a variety of routes including, inter alia, intravenous injection, intracranial injection, intrathecal injection, and the like.

Various embodiments contemplated herein may include, but need not be limited to, one or more of the following:

In one aspect, the disclosure provides a vector comprising an *adeno-associated virus* (AAV) genome or a derivative thereof and a promoter operably linked to a polynucleotide sequence encoding CLN3, e.g. a human CLN3, or an equivalent of each thereof.

In another aspect, the disclosure provides a vector comprising a self-complementary AAV9 genome or a derivative thereof and a promoter operably linked to a polynucleotide sequence encoding CLN3, wherein the promoter drives low CLN3 expression.

In another aspect, the disclosure provides a method for the treatment and/or prophylaxis of Juvenile neuronal ceroid lipofuscinosis (JNCL) in a mammal, the method comprising, or alternatively consisting essentially of, or alternatively consisting of, transforming cells of the mammal with a construct that expresses CLN3 where the CLN3 is expressed at an effective amount to treat and/or prevent JNCL In some embodiments, the CLN3 is a human CLN3. In other embodiments, the CLN3 is a non-human CLN3.

In some embodiments, the AAV genome is from a naturally derived serotype or an isolate or a clade of AAV. In some embodiments, the AAV serotype is selected from the group of AAV1, AAV2, AAV4, AAV5, AAV6, AAV8, or AAV9. In preferred embodiments, the AAV serotype is AAV9. In other embodiments, the AAV serotype is AAV2.

In some embodiments, the vector is a derivative of AAV, e.g., a single-stranded AAV (ss-AAV) vector. In other embodiments, the derivative vector is a self-complementary AAV (sc-AAV) vector.

In some embodiments, the promoter is selected from a *cytomegalovirus* (CMV), a chicken β-actin (CBA), an Ubiquitin C (UBC), a B-glucuronidase (GUSB), a neuron-specific enolase (NSE), a Synapsin, a MeCP2 (methyl-CPG binding protein 2), a glial fibrillary acidic protein (GFAP), a β-actin 9 (e.g. chicken beta actin), or a CBh (hybrid CBA or a MVM intron with CBA promoter).

In some embodiments, the promoter is a neuron-, astrocyte-, or oligodendrocyte-specific or neuron-, astrocyte-, or oligodendrocyte-preferential promoter, for example, an NSE, a Synapsin, a MeCP2, an oligodendrocyte transcription factor 1 (Olig1), a chondroitin sulfate proteoglycan (Cspg4), a CNP (2',3'-Cyclic-nucleotide 3'-phosphodiesterase), or a GFAP promoter.

In some embodiments, the vector further comprises, or alternatively consists essentially of, or yet further consists of a 5'UTR/intron selected from SV40 or CBA-MVM. In some embodiments, the vector further comprises, or alternatively consists essentially of or yet further consists of, a minimal SV40 intron. In other embodiments, the vector further comprises or alternatively consists essentially of, or yet further consists of a polyadenylation signal selected from a bovine growth hormone polyadenylation sequence, a SV40 late polyadenylation sequence, a SV40 early polyadenylation sequence, an AATAAA (SEQ ID NO: 3) polyadenylation signal, a CAATAAA (SEQ ID NO: 4) polyadenylation signal, an ATTAAA (SEQ ID NO: 5) polyadenylation signal, or a TANA (SEQ ID NO: 6) polyadenylation signal. In yet other embodiments, the vector further comprises or alternatively consists essentially of, or yet further consists of a posttranslational regulatory element, non-limiting examples of such include for example, a Woodchuck Post-transcriptional Regulatory Element (WPRE), a WPRE2 containing a minimal gamma element and a partial alpha-beta element, a WPRE3 and containing minimal gamma and alpha elements, or a *hepatitis B virus* posttranscriptional regulatory element (HPRE).

In some embodiments, the vector comprises one or more of the above elements and the vector is an AAV9 comprising a self-complementary genome.

In some embodiments, the polynucleotide encoding CLN3, e.g., human CLN3, or an equivalent thereof is operably linked to a MeCP2 promoter.

In some embodiments, the vector drives low CLN3 expression or an equivalent thereof.

In a further aspect, the vectors as described herein further comprise a gene or polypeptide that is a detectable label. Examples of such are exemplified in FIG. 1.

In some embodiments, the disclosure provides methods and uses of the vectors as describe herein, which methods comprise transforming cells of the central nervous system of the mammal with a vector as described herein. In other embodiments, the method comprises transforming cells contained within non-CNS tissue(s) with a vector as described herein.

In some embodiments, the method is performed on a mammal that in one aspect is a human and the CLN3 is a human CLN3 or an equivalent thereof.

In some embodiments, the human to be treated is homozygous for a CLN3 mutation. In a further aspect, the CLN3 mutation is related to the development of Batten disease in the human bearing the homozygous mutation.

In some embodiments, the mammal to be treated is a human neonate, a human infant, or a human adolescent. In other embodiments, the mammal to be treated is a human adult.

In some embodiments, the mammal, such as a human patient to be treated, is asymptomatic for JNCL. In other embodiments, the mammal to be treated is symptomatic for JNCL, for example, the mammal presents, with blindness, seizures, motor loss, cognitive decline, or any combination thereof.

The methods as disclosed herein comprise, or alternatively et:insist essentially of, or yet further consists of, administering to the mammal in need of such treatment and/or prophylaxis an effective amount of a vector, and/or an rAAV, and/or a pharmaceutical formulation containing the vector according to any one of the embodiments as described herein.

In some embodiments, the administration is via a route selected from one or more of intracerebral administration, intrathecal administration), intravenous, oral, aerosol administration, administration via inhalation (including intranasal and intratracheal delivery), intravenous, intramuscular, subcutaneous, intradermal, and rectal administration.

In some embodiments, the treatment regimen comprises a single administration, for example, a single systemic administration. In other embodiments, the treatment regimen comprises at least 2, at least 3, at least 4, at least 5, at least 6, at least 7, at least 8, at least 9, or at least 10 administrations. The dosing of the vector for each administration may be the same or different, as determined by the treating physician or professional.

In some embodiments, each administration comprises about $10^{10}$ up to about $10^{16}$ genome copies of CLN3 or an equivalent thereof per kg of body weight of the mammal to be treated. In other embodiments, each administration comprises about $10^{10}$ up to about $10^{16}$ genome copies of CLN3 or an equivalent thereof per subject.

In one aspect, the disclosure provides a host cell transduced with a vector according to any one of the embodiments as described herein.

In one aspect, the disclosure provides a method of transducing cells, the method comprising, or alternatively consisting essentially of, or yet further consisting of introducing into a host cell, a composition comprising an AAV vector according to any one of the embodiments as described herein.

In another aspect, the disclosure provides a recombinant *adeno-associated virus* that comprises a nucleic acid construct that encodes human CLN3 or an equivalent thereof. In one embodiment, the *adeno-associated virus* comprises a vector according to any one of the embodiments as described herein.

In another aspect, the disclosure provides a recombinant *adeno-associated virus* according to any one of the above embodiments and a carrier, such as a pharmaceutically acceptable carrier or diluent. In some embodiments, the formulation is formulated for administration via a route selected from the group consisting of intracerebral administration, intrathecal administration, intravenous, oral, aerosol administration, administration via inhalation (including intranasal and intratracheal delivery), intravenous, intramuscular, subcutaneous, intradermal, and rectal administration. In other embodiments, the formulation is a sterile injectable.

In another aspect, the disclosure provides for the use of the vector of any one of the embodiments as described herein for the treatment and/or prophylaxis Juvenile Neuronal Ceroid Lipofuscinosis (JNCL).

BRIEF DESCRIPTION OF THE FIGURES

FIG. 2F summarizes the data depicted in FIGS. 2A-2E showing improved motor behavior in CLN3$^{\Delta ex7/8}$ mice receiving scAAV9/MeCP2-hCLN3.

FIGS. 6A-6B show comparative biodistribution of scAAV9/ β-actin-GFP or scAAV9/MeCP2-GFP in the brains of CLN3$^{\Delta ex7/8}$ mice 5 months after administration as depicted by number of GFP$^+$ cells.

FIG. 8A shows that systemic administration of scAAV9 transduces neurons in the CLN3$^{\Delta ex7/8}$ brain. One month-old CLN3$^{\Delta ex7/8}$ mice (4/group) received one injection of 2×10$^{12}$ vg scAAV9/MeCP2-GFP i.v., whereupon brain tissues were collected 5 months later and stained for NeuN, GFP, and nuclei (DAPI) in the indicated brain regions for confocal microscopy. Insets depict regions indicated at higher magnification. FIG. 8B shows that systemic administration of scAAV9 transduces astrocytes in the CLN3$^{\Delta ex7/8}$ brain. FIG. 8C shows that systemic administration of scAAV9 does not transduce microglia in the CLN3$^{\Delta ex7/8}$ brain.

DETAILED DESCRIPTION

Figure 1:
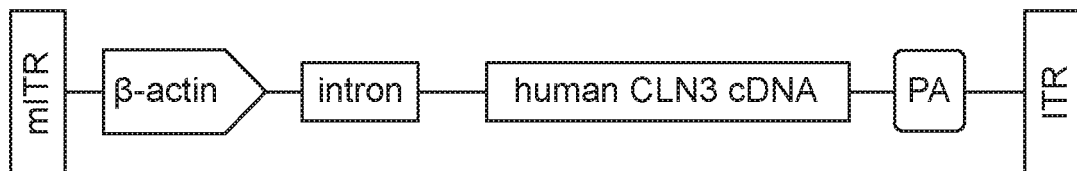
FIG. 1 depicts exemplary AAV9 hCLN3 constructs. Each construct contains identical minimal SV40 intron (labeled "intron"), human CLN3 cDNA, bovine growth hormone polyadenylation signals ("PA"), and viral inverted terminal repeats to package self-complementary (sc) virus. The first construct contains the high expressing chicken β-actin promoter, while the second contains the minimal essential promoter from the mouse MeCP2 gene. Control constructs replace human CLN3 cDNA with a polynucleotide encoding green fluorescent protein (GFP).
Figure 1:
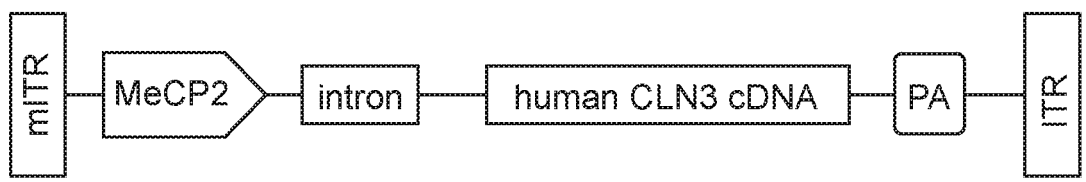
Figure 1:
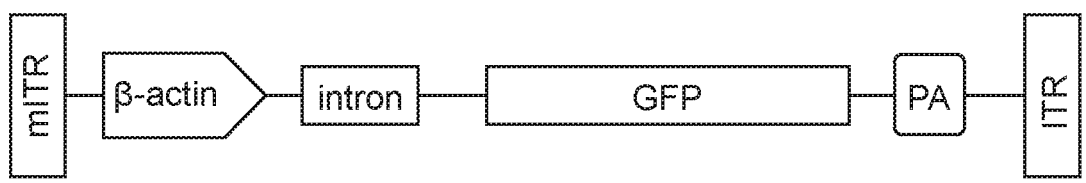
Figure 1:
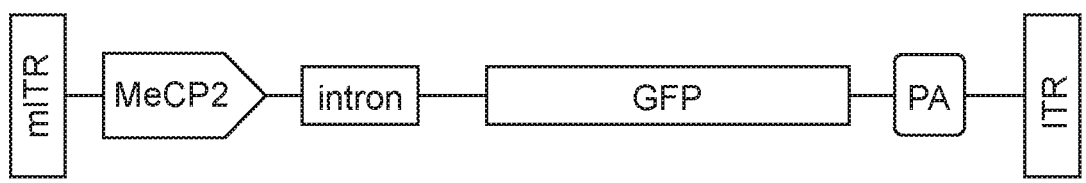

It is to be understood that this invention is not limited to particular embodiments described, as such may, of course, vary. It is also to be understood that the terminology used herein is for the purpose of describing particular embodiments only, and is not intended to be limiting, since the scope of this invention will be limited only by the appended claims.

The detailed description of the invention is divided into various sections only for the reader's convenience and disclosure found in any section may be combined with that in another section. Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated by reference to disclose and describe the methods and/or materials in connection with which the publications are cited.

All numerical designations, e.g., pH, temperature, time, concentration, and molecular weight, including ranges, are approximations which are varied (+) or (−) by increments of 0.1 or 1.0, where appropriate. It is to be understood, although not always explicitly stated that all numerical designations are preceded by the term "about." It also is to be understood, although not always explicitly stated, that the reagents described herein are merely exemplary and that equivalents of such are known in the art.

It must be noted that as used herein and in the appended claims, the singular forms "a", "an", and "the" include plural referents unless the context clearly dictates otherwise. Thus, for example, reference to "a cell" includes a plurality of cells.

I. Definitions

As used herein the following terms have the following meanings.

The term "about" when used before a numerical designation, e.g., temperature, time, amount, concentration, and such other, including a range, indicates approximations which may vary by (+) or (−)10%, 5% or 1%.

"Comprising" or "comprises" is intended to mean that the compositions, for example media, and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention.

As used herein, the term "vector" refers to a polynucleotide construct, typically a plasmid or a virus, used to transmit genetic material to a host cell. Vectors can be, for example, viruses, plasmids, cosmids, or phage. A vector as used herein can be composed of either DNA or RNA. In some embodiments, a vector is composed of DNA. An "expression vector" is a vector that is capable of directing the expression of a protein encoded by one or more genes carried by the vector when it is present in the appropriate environment. Vectors are preferably capable of autonomous replication. Typically, an expression vector comprises a transcription promoter, a gene, and a transcription terminator. Gene expression is usually placed under the control of a promoter, and a gene is said to be "operably linked to" the promoter.

As used herein, the term "operably linked" is used to describe the connection between regulatory elements and a gene or its coding region. Typically, gene expression is placed under the control of one or more regulatory elements, for example, without limitation, constitutive or inducible promoters, tissue-specific regulatory elements, and enhancers. A gene or coding region is said to be "operably linked to" or "operatively linked to" or "operably associated with" the regulatory elements, meaning that the gene or coding region is controlled or influenced by the regulatory element. For instance, a promoter is operably linked to a coding sequence if the promoter effects transcription or expression of the coding sequence.

The terms "nucleic acid" or "polynucleotide" are used interchangeably herein. In some embodiments, the nucleic acid comprises at least two nucleotides covalently linked together. In some embodiments, the nucleic acid of the present invention is single-stranded. In some embodiments, the nucleic acid is double stranded. In some embodiments, the nucleic acid is triple-stranded. In some embodiments, the nucleic acid comprises phosphodiester bonds. In some embodiments, the nucleic acid comprises a single-stranded or double-stranded deoxyribonucleic acid (DNA) or a single-stranded or double-stranded ribonucleic acid (RNA). In some embodiments, the nucleic acid comprises a nucleic acid analog. In some embodiments, the nucleic acid analog has a backbone, comprising a bond other than and/or in addition to a phosphodiester bond, such as, by non-limiting example, phosphoramide, phosphorothioate, phosphorodithioate or O-methylphophoroamidite linkage. In some embodiments, the nucleic acid analog is selected from a nucleic acid analog with a backbone selected from a positive backbone; a non-ionic backbone and a non-ribose backbone. In some embodiments, the nucleic acid contains one or more carbocyclic sugars. In some embodiments, the nucleic acid comprises modifications of its ribose-phosphate backbone. In some embodiments, these modifications are performed to facilitate the addition of additional moieties such as labels. In some embodiments, these modifications are performed to increase the stability and half-life of such molecules in physiological environments.

The term "regulatory element" and "expression control element" are used interchangeably and refer to nucleic acid molecules that can influence the expression of an operably linked coding sequence in a particular host organism. These terms are used broadly to and cover all elements that promote or regulate transcription, including promoters, core elements required for basic interaction of RNA polymerase and transcription factors, upstream elements, enhancers, and response elements (see, e.g., Lewin, "Genes V" (Oxford University Press, Oxford) pages 847-873). Illustrative, but non-limiting regulatory elements in prokaryotes include promoters, operator sequences ribosome binding sites, transcriptional and translational control sequences, such as promoters, enhancers, splicing signals, polyadenylation signals, terminators, protein degradation signals, internal ribosome-entry element (IRES), 2A sequences, and the like, that provide for and/or regulate expression of a coding sequence and/or production of an encoded polypeptide in a host cell.

As used herein, the term "promoter" is a nucleotide sequence that permits binding of RNA polymerase and directs the transcription of a gene. Typically, a promoter is located in the 5' non-coding region of a gene, proximal to the transcriptional start site of the gene. Sequence elements within promoters that function in the initiation of transcription are often characterized by consensus nucleotide sequences. Examples of promoters include, but are not limited to, promoters from bacteria, yeast, plants, viruses, and mammals (including humans). A promoter can be inducible, repressible, and/or constitutive. Inducible promoters initiate increased levels of transcription from DNA under their control in response to some change in culture conditions, such as a change in temperature.

As used herein, the term "enhancer" refers to a type of regulatory element that can increase the efficiency of transcription. In certain embodiments, the enhancer acts to increase transcription regardless of the distance or orientation of the enhancer relative to the start site of transcription.

As used herein, the term "transfection" is synonymous with "transducing" and refers to the introduction of a nucleic acid, such as an exogenous nucleic acid, into a host cell. In certain embodiments the introduction is by contacting the cell with a recombinant AAV virus or vector comprising the nucleic acid (e.g., an expression cassette) that is to be introduced. An AAV genome is a genome that is in whole or in part derived from an *adeno-associated virus* that infects humans and other primates. The AAV genome is comprised of single-stranded DNA (ssDNA), either positive- or negative-sensed. The genome comprises inverted terminal repeats (ITRs) at both ends of the DNA and two open reading frames. A self-complementary AAV (scAAV) is a viral vector created from wild-type AAV. The self-complementary AAV is an example of a AAV derivative and is an engineered viral vector derived from AAV that has been designed to form an intra-molecular double-stranded DNA template.

As used herein, the term "transgene" refers to any nucleotide or DNA sequence that is transfected into a target cell. The construct comprising the transgene may exist as a stable episome, or may be integrated into one or more chromosomes of a target cell. In some embodiments, the transgene comprises a polynucleotide that encodes a protein of interest (e.g. CLN3). The polynucleotide encoding the desired protein is generally operatively linked to other sequences that are useful for obtaining the desired expression of the gene of interest, such as promoters, enhancers, transcriptional regulatory sequences, and the like.

As used herein, the ceroid-lipofuscinosis, neuronal 3 gene or ("CLN3 gene") intends a nucleic acid that encodes a protein that is involved in lysosomal function. Mutations in this gene cause neurodegenerative diseases. The nucleic acid encoding the human protein and the human protein are known in the art and provided at GenBank Accession No. NM_001042432 (last accessed on Dec. 15, 2015), and examples of non-human CLN3 genes are the rat and mouse homologs, that are available at the website genenames.org/cgi-bin/gene_symbol_report?hgnc_id=HGNC:2074, last accessed on Dec. 15, 2015.

The terms "treatment, treat, treating, etc." as used herein, include but are not limited to, alleviating a symptom of a disease or condition (e.g., Juvenile neuronal ceroid lipofuscinosis (JNCL or Juvenile Batten disease)) and/or reducing, suppressing, inhibiting, lessening, ameliorating or affecting the progression, severity, and/or scope of the disease or condition. "Treatments" refer to one or both of therapeutic treatment and prophylactic or preventative measures. Subjects in need of treatment include those already affected by a disease or disorder or undesired physiological condition as well as those in which the disease or disorder or undesired physiological condition is to be prevented.

The term "effective amount," as used herein, refers to an amount that is capable of treating or ameliorating the disease or condition or otherwise capable of producing an intended therapeutic effect. In certain embodiments, an effective amount is an amount sufficient to reduce, prevent, or delay the onset of one or more symptoms of JNCL. Such symptoms may include, but are not limited to vision problems or blindness, seizures, personality and/or behavior changes, slow learning, clumsiness, stumbling, mental impairment, and loss of motor skills.

The terms "patient," "subject," or "mammalian subject" are used interchangeably herein and include any mammal in need of the treatment or prophylactic methods described herein (e.g., methods for the treatment or prophylaxis of JNCL). Such mammals include, particularly humans (e.g., fetal humans, human infants, human teens, human adults, etc.). Other mammals in need of such treatment or prophylaxis can include non-human mammals such as dogs, cats, or other domesticated animals, horses, livestock, laboratory animals (e.g., lagomorphs, non-human primates, etc.), and the like. The subject may be male or female. In certain embodiments the subject is at risk, but asymptomatic for JNCL (e.g., a child that has a genetic diagnosis of JNCL before clinical signs are apparent (this rarely occurs), or a child that has a genetic diagnosis of JNCL at an age before clinical symptoms develop (i.e. birth to around.4-5 years), e.g., where genetic testing is triggered by an older sibling with a confirmed diagnosis of JNCL). In certain embodiments, the subject expresses symptoms of JNCL.

The term "administering" or "administration" of vector to a subject includes any route of introducing or delivering to a subject the vector to perform its intended function. Administration can be carried out by any suitable route, including orally, intranasally, parenterally (intravenously, intramuscularly, intraperitoneally, or subcutaneously), intracranially, or topically. Administration includes self-administration and the administration by another.

The terms "polynucleotide," "nucleic acid" and "oligonucleotide" are used interchangeably and refer to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of this invention that is a polynucleotide encompasses both the double-stranded form and each of two complementary single-stranded forms known or predicted to make up the double-stranded form.

A polynucleotide is composed of a specific sequence of four nucleotide bases: adenine (A); cytosine (C); guanine (G); thymine (T); and uracil (U) for thymine when the polynucleotide is RNA. Thus, the term "polynucleotide sequence" is the alphabetical representation of a polynucleotide molecule. This alphabetical representation can be input into databases in a computer having a central processing unit and used for bioinformatics applications such as functional genomics and homology searching.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, or alternatively less than 25% identity, with one of the sequences of the present invention.

A polynucleotide or polynucleotide region (or a polypeptide or polypeptide region) has a certain percentage (for example, 70%, 75%, 80%, 85%, 90%, 95%, 98% or 99%) of "sequence identity" to another sequence means that, when aligned, that percentage of bases (or amino acids) are the same in comparing the two sequences. This alignment and the percent homology or sequence identity can be determined using software programs known in the art, for example those described in Ausubel et al. eds. (2007) Current Protocols in Molecular Biology. Preferably, default parameters are used for alignment. One alignment program is BLAST, using defaultparameters. In particular, programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE;

Databases=non-redundant, GenBank+EMBL+DDBJ+PDB+GenBank CDS translations+SwissProtein+SPupdate+PIR. Details of these programs can be found at the following Internet address: http://www.ncbi.nlm.nih.gov/cgi-bin/BLAST.

An equivalent or biological equivalent nucleic acid, polynucleotide or oligonucleotide or peptide is one having at least 70% sequence identity, or alternatively at least 80% sequence identity, or alternatively at least 85% sequence identity, or alternatively at least 90% sequence identity, or alternatively at least 92% sequence identity, or alternatively at least 95% sequence identity, or alternatively at least 97% sequence identity, or alternatively at least 98% sequence identity to the reference nucleic acid, polynucleotide, oligonucleotide or peptide. An alternative equivalent polypepeptide is a polypeptide encoded by a nucleic acid that hybridizes under conditions of high stringency to a reference polynucleotide or its complement. An alternative equivalent polynucleotide is one that hybridizes under conditions of high stringency to a reference polynucleotide or its complement.

"Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR reaction, or the enzymatic cleavage of a polynucleotide by a ribozyme.

Hybridization reactions can be performed under conditions of different "stringency". In general, a low stringency hybridization reaction is carried out at about 40° C. in 10×SSC or a solution of equivalent ionic strength/temperature. A moderate stringency hybridization is typically performed at about 50° C. in 6×SSC, and a high stringency hybridization reaction is generally performed at about 60° C. in 1×SSC. Additional examples of stringent hybridization conditions include: low stringency of incubation temperatures of about 25° C. to about 37° C.; hybridization buffer concentrations of about 6×SSC to about 10×SSC; formamide concentrations of about 0% to about 25%; and wash solutions from about 4×SSC to about 8×SSC. Examples of moderate hybridization conditions include: incubation temperatures of about 40° C. to about 50° C.; buffer concentrations of about 9×SSC to about 2×SSC; formamide concentrations of about 30% to about 50%; and wash solutions of about 5×SSC to about 2×SSC. Examples of high stringency conditions include: incubation temperatures of about 55° C. to about 68° C.; buffer concentrations of about 1×SSC to about 0.1×SSC; formamide concentrations of about 55% to about 75%; and wash solutions of about 1×SSC, 0.1×SSC, or deionized water. In general, hybridization incubation times are from 5 minutes to 24 hours, with 1, 2, or more washing steps, and wash incubation times are about 1, 2, or 15 minutes. SSC is 0.15 M NaCl and 15 mM citrate buffer. It is understood that equivalents of SSC using other buffer systems can be employed. Hybridization reactions can also be performed under "physiological conditions" which is well known to one of skill in the art. A non-limiting example of a physiological condition is the temperature, ionic strength, pH and concentration of $Mg^{2+}$ normally found in a cell.

As used herein, the term "low expression" intends less than that expressed using a "high expression" promoter such as the β-actin or CMV promoter that are known in the art to drive gene expression at higher than the native promoter. A non-limiting of a low expression promoter is the MeCP2 promoter.

MODES FOR CARRYING OUT THE DISCLOSURE

Juvenile Neuronal Ceroid Lipofuscinosis (JNCL) or Juvenile Batten Disease is a lysosomal storage disorder caused by an autosomal recessive mutation in CLN3. JNCL presents between 5-10 years of age, with progressive vision loss, seizures, cognitive and motor decline, and death occurring by the late teens to early 20s. There is no cure for JNCL, which underscores the significance of identifying novel therapeutics to improve lifespan and quality-of-life for children suffering from this deadly disease.

Current therapeutic approaches for JNCL target pathological sequelae. However, to provide long-lasting protection, alternative strategies are required. One such approach is gene therapy. Gene therapy has shown promise in correcting some forms of Batten Disease that involve mutations in soluble enzymes, in part, due to cross-correction of neighboring non-transduced cells. However, since CLN3 is a transmembrane protein, gene therapy approaches have been considered less practical for JNCL. Despite this, recent evidence has suggested that gene therapy for JNCL may be feasible, where the intracranial delivery of an *adenoassociated virus* (AAV) vector harboring human CLN3 was capable of reducing lysosomal inclusions, although no changes in behavioral deficits were reported.

As illustrated herein in the Examples, AAV9/hCLN3 constructs have been engineered using the β-actin or MeCP2 promoters to drive high versus low expression of hCLN3, respectively. One (1) month-old $CLN3^{\Delta ex7/8}$ mice were injected with $2 \times 10^{12}$ viral genomes (vg) of AAV9/ β-actin-hCLN3 or AAV9/MeCP2-hCLN3 intravenously, with viruses driving green fluorescence protein (GFP) expression (AAV9/ β-actin-GFP and AAV9/MeCP2-GFP) as controls.

Importantly, a promoter-dosage effect for hCLN3 was confirmed in several brain regions where neurons are destined to die in JNCL, including the hippocampus (HPC), striatum (STR), thalamus (TH), visual cortex (VC), and cerebellum (CB), where hCLN3 expression was elevated 3- to 8-fold in $CLN3^{\Delta ex7/8}$ mice receiving high expressing AAV9/ β-actin-hCLN3 vs. AAV9/MeCP2-hCLN3. Animals receiving AAV9/GFP constructs revealed that the virus mainly transduced $NeuN^+$ neurons, with a few $GFAP^+$ astrocytes also observed, whereas GFP expression was not detected in microglia. The extent of viral transduction in the brain was widespread, as evident by GFP expression in the somatosensory barrel field cortex (S1BF), VC, STR, HPC, SCN, and CB.

Importantly, only the AAV9 construct driving low hCLN3 expression (AAV9/MeCP2-hCLN3) was capable of restoring motor deficits of $CLN3^{\Delta ex7/8}$ mice (accelerating rotarod and pole climbing) to performance levels typical of WT animals, demonstrating that high CLN3 expression in the brain was not advantageous for improved motor coordination. Similar benefits were observed with lysosomal storage material, which was significantly reduced in the S1BF, VC, and TH of animals receiving AAV9/MeCP2-hCLN3. The beneficial effects of AAV9/MeCP2-hCLN3 on motor behavior in $CLN3^{\Delta ex7/8}$ mice were not observed with GFP control constructs, confirming specificity of action for hCLN3.

Based on these observations and without being bound by theory, it is believed that AAV/hCLN3 (e.g., AAV9/hCLN3)-mediated gene therapy will target sufficient numbers of CNS cells to significantly improvement JNCL outcome. In this regard, it is noted that heterozygous carriers of the CLN3 mutation (i.e. ½ gene dosage) do not have any evidence of disease or pathology indicating that these "reduced levels of CLN3 expression" are sufficient to produce healthy cells. The scAAV9/MeCP2-GFP virus described herein has been used to identify the frequency of transduced cells in the CNS. Albeit at a modest frequency, the method used to identify cells transduced with viral constructs (i.e. immunofluorescence staining with GFP antibody) has limited sensitivity suggesting that it is possible that the number of cells in the brain that were transduced may be underestimated. Nevertheless, the dramatic improvements in disease readouts described herein indicate that the AAV gene therapy approach(es) described herein are effective.

Accordingly in various embodiments, AAV/hCLN3 constructs, rAAV that express hCLN3, and methods of treatment and/or prophylaxis utilizing AAV/hCLN3 constructs are provided.

AAV Vectors and Compositions

In certain embodiments the polynucleotide encoding a CLN3 protein is delivered to cells within or comprising one or more tissues of the central nervous system (CNS) by means of a viral vector, of which many are known and available in the art. Additionally, in various embodiments CLN3 will also be delivered to systemic tissues, which is important because children with Juvenile Batten Disease also have systemic disease symptoms (i.e. cardiac defects). In this regard it is noted that CLN3 is ubiquitously expressed in all cell types in the body. The viral vector(s) are desirably non-toxic, non-immunogenic, easy to produce, and efficient in protecting and delivering DNA into the target cells. In one illustrative, but non-limiting embodiment, the viral vector is an *adeno-associated virus* vector or a derivative thereof and therapeutic compositions comprising adeno-associated viral vector or a derivative thereof comprising the nucleic acid sequence encoding CLN3 polypeptide is under the control of a suitable promoter.

More than 30 naturally occurring serotypes of AAV are available and are useful in the constructs and methods as described herein. Many natural variants in the AAV capsid exist, allowing identification and use of an AAV with properties specifically suited for neural cells as well as other cell types. AAV viruses can be engineered by conventional molecular biology techniques, making it possible to optimize these particles for cell specific delivery of the desired nucleic acid sequences, for minimizing immunogenicity, for tuning stability and particle lifetime, for efficient degradation, for accurate delivery to the nucleus, etc.

The use of AAVs is a common mode of exogenous delivery of DNA as it is relatively non-toxic, provides efficient gene transfer, and can be easily optimized for specific purposes. Among the serotypes of AAVs isolated from human or non-human primates (NHP) and well characterized, human serotype 2 is the first AAV that was developed as a gene transfer vector. This serotype has been widely used for efficient gene transfer experiments in different target tissues and animal models. Other AAV serotypes include useful in the vectors and methods of this disclosure include, but are not limited to, AAV1, AAV3, AAV4, AAV5, AAV6, AAV6.2, AAV7, AAV8, AAV9, rh.10, rh.39, rh,43, CSP3, and the like (see, e.g., WO 2005/033321 and U.S. Pat. No. 7,198,951) for a discussion of various AAV serotypes). In certain embodiments the serotype is selected to optimize the desired mode of delivery. For example, AAV1, AAV5, and AAV9 provide the good vector spread and high efficiency of transduction. AAV1 and AAV9 provide almost exclusively neuronal tropism, while AAV5 provides a mix of neurons and glia, and AAV4 targets mostly astrocytes (see, e.g., Davidson et al. (2000) *Proc. Natl. Acad. Sci. USA,* 97: 3428-3432); Burger et al. (2004) *Mol. Ther.* 10: 302-317; Cearley and Wolfe (2006) *Mol. Ther.* 13: 528-537). AAV1 and AAV6 have superior retrograde axonal transport capabilities following peripheral injection (Hollis et al. (2008)*Mol. Ther.* 16: 296-301), while AAV9 undergoes efficient axonal transport within the brain (Cearley and Wolfe, (2006) supra.). AAV6, AAV8, and AAV9 have demonstrated efficient delivery to the spinal cord and dorsal root ganglia following intrathecal administration, targeting different subsets of cells depending on the specific serotype (Storek et al. (2008) *Proc. Natl. Acad. Sci. USA,* 105: 1055-1060; Towne et al. (2009) *Mol. Pain,* 5:52; Snyder et al. (2011) *Hum. Gene Ther.,* 22: 1129-1135). Intracerebral ventricular injection of AAV4 efficiently transduces ependymal cells (Liu et al. (2005) *Gene Ther.* 12:1503-1508). As demonstrated herein AAV9 can cross the blood-brain barrier (BBB) following intravenous administration to transduce neurons and glia within the brain. In certain embodiments the rh.10 serotype is expressly excluded. Thus, it is within the scope of this disclosure that dosages of different AAV serotypes can be administered to the patient concurrently and/or sequentially, to provide targeted delivery to personalize the therapy based on the symptoms and progression of the disease.

Desirable AAV fragments for assembly into vectors include the cap proteins known in the art, including the vp1 (e.g., SEQ ID NOs: 12 and 13), vp2 (e.g., SEQ ID NOs: 14 and 15), vp3 (e.g., SEQ ID NOs: 16 and 17) and hypervariable regions, the rep proteins, including rep 78 (e.g., SEQ ID NO: 18), rep 68 (e.g., SEQ ID NO: 19), rep 52 (e.g., SEQ ID NO: 20), and rep 40 (e.g., SEQ ID NO: 21), and the sequences encoding these proteins and equivalents thereof. These fragments may be readily utilized in a variety of vector systems and host cells. Such fragments maybe used alone, in combination with other AAV serotype sequences or fragments, or in combination with elements from other AAV or non-AAV viral sequences. As used herein, artificial AAV serotypes include, without limitation, AAV with a non-naturally occurring capsid protein. Such an artificial capsid may be generated by any suitable technique. Using a selected AAV sequence (e.g., a fragment of a vp1 capsid protein) in combination with heterologous sequences which may be obtained from a different selected AAV serotype, non-contiguous portions of the same AAV serotype, from a non-AAV viral source, or from a non-viral source. An artificial AAV serotype may be, without limitation, a pseudotyped AAV, a chimeric AAA' capsid, a recombinant AAV capsid, or a "humanized" AAV capsid. Pseudotyped vectors, in which the capsid of one AAV is replaced with a heterologous capsid protein, also useful. (see, e.g. Asokan A. (2010) *Discov. Med.* 9(48):399-403).

In one illustrative, but non-limiting embodiment, the vectors useful in compositions and methods described herein contain, at a minimum, sequences encoding a selected AAV serotype capsid, e.g., an AAV9 capsid (e.g., SEQ ID NO: 13), or a fragment or equivalent thereof. In another embodiment, useful vectors contain, at a minimum, sequences encoding a selected AAV serotype rep protein, e.g., AAV9 rep protein, or a fragment thereof. Optionally, such vectors may contain both AAV cap and rep proteins. In vectors in which both AAV rep and cap are provided, the AAV rep and AAV cap sequences can both be of one serotype origin, e.g., all AAV9 origin. (see, e.g. Balakrishnan et al. (2014) *Curr. Gene. Therap.* 14:1-15; U.S. Pat. No. 8,962,330and 7,198, 951).

Alternatively, vectors may be used in which the rep sequences are from an AAV serotype that differs from that which is providing the cap sequences. In one embodiment, the rep and cap sequences are expressed from separate sources (e.g., separate vectors, or a host cell and a vector). In another embodiment, these rep sequences are fused in frame to cap sequences of a different AAV serotype to form a chimeric AAV vector, such as AAV2/8 described in U.S. Pat. No. 7,282,199. In some embodiments, an AAV1 rep protein is fused in frame to cap sequences of the AAV serotype selected from the group consisting of AAV2, AAV3, AAV4, AAV5, AAV6, AAV6.2, AAV7, AAV8, AAV9, rh.10, rh.39, rh.43, and CSP3. In some embodiments, an AAV2 rep protein is fused in frame to cap sequences of the AAV serotype selected from the group consisting of AAV1, AAV3, AAV4, AAV5, AAV6, AAV6.2, AAV7, AAV8, AAV9, rh.10, rh.39, rh.43, and CSP3. In some embodiments, an AAV3 rep protein is fused in frame to cap sequences of the AAV serotype selected from the group consisting of AAV1, AAV2, AAV4, AAV5, AAV6, AAV6.2, AAV7, AAV8, AAV9, rh.10, rh.39, rh.43, and CSP3. In some embodiments, an AAV4 rep protein is fused in frame to cap sequences of the AAV serotype selected from the group consisting of AAV1, AAV2, AAV3, AAV5, AAV6, AAV6.2, AAV7, AAV8, AAV9, rh.10, rh.39, rh.43, and CSP3. In some embodiments, an AAV5 rep protein is fused in frame to cap sequences of the AAV serotype selected from the group consisting of AAV1, AAV2, AAV3, AAV4, AAV6, AAV6.2, AAV7, AAV8, AAV9, rh.10, rh.39, rh.43, and CSP3. In some embodiments, an AAV6 rep protein is fused in frame to cap sequences of the AAV serotype selected from the group consisting of AAV1, AAV2, AAV3, AAV4, AAV5, AAV6.2, AAV7, AAV8, AAV9, rh.10, rh.39, rh.43, and CSP3. In some embodiments, an AAV6.2 rep protein is fused in frame to cap sequences of the AAV serotype selected from the group consisting of AAV1, AAV2, AAV3, AAV4, AAV5, AAV6, AAV7, AAV8, AAV9, rh.10, rh.39, rh.43, and CSP3. In some embodiments, an AAV7 rep protein is fused in frame to cap sequences of the AAV serotype selected from the group consisting of AAV1, AAV2, AAV3, AAV4, AAV5, AAV6.2, AAV6.2, AAV8, AAV9, rh.10, rh.39, rh.43, and CSP3. In some embodiments, an AAV8 rep protein is fused in frame to cap sequences of the AAV serotype selected from the group consisting of AAV1, AAV2, AAV3, AAV4, AAV5, AAV6.2, AAV6.2, AAV7, AAV9, rh.10, rh.39, rh.43, and CSP3. In some embodiments, an AAV9 rep protein is fused in frame to cap sequences of the AAV serotype selected from the group consisting of AAV1, AAV2, AAV3, AAV4, AAV5, AAV6.2, AAV6.2, AAV7, AAV8, rh.10, rh.39, rh.43, and CSP3. In some embodiments, an AAVrh.10 rep protein is fused in frame to cap sequences of the AAV serotype selected from the group consisting of AAV1, AAV2, AAV3, AAV4, AAV5, AAV6.2, AAV6.2, AAV7, AAV8, AAV9, rh.39, rh.43, and CSP3. In some embodiments, an AAVrh.39 rep protein is fused in frame to cap sequences of the AAV serotype selected from the group consisting of AAV1, AAV2, AAV3, AAV4, AAV5, AAV6.2, AAV6.2, AAV7, AAV8, AAV9, rh.10, rh.43, and CSP3. In some embodiments, an AAVrh.43 rep protein is fused in frame to cap sequences of the AAV serotype selected from the group consisting of AAV1, AAV2, AAV3, AAV4, AAV5, AAV6.2, AAV6.2, AAV7, AAV8, AAV9, rh.10, rh.39, and CSP3. In some embodiments, an AAVCSP3 rep protein is fused in frame to cap sequences of the AAV serotype selected from the group consisting of AAV1, AAV2, AAV3, AAV4, AAV5, AAV6.2, AAV6.2, AAV7, AAV8, AAV9, rh.10, rh.39, and rh.43.

Typically the vectors are composed of, at a minimum, a transgene and its necessary regulatory sequences, and 5' and 3' AAV inverted terminal repeats (ITRs). Non-limiting examples of ITRs include nucleotides 662 to 767 and nucleotides 3278 to 3418 of SEQ ID NO: 2 and equivalents of each thereof. The recombinant AAV vector is packaged into a capsid protein and delivered to a selected target cell. Thus, in one aspect, the vector contained within the capsid and/or target cell is an aspect of this disclosure. As contemplated herein, the transgene is one that encodes a CLN3 gene product (e.g., a CLN3 polypeptide (see, e.g., International Batten Disease Consortium (1995) *Cell,* 82:949-957, and GenBank Accession No: AAC05337 (SEQ ID NO:1), SEQ ID NO:7, SEQ ID NO:8, SEQ ID NO: 9, SEQ ID NO: 10, nucleotides 1683 to 2999 of SEQ ID NO:2, and equivalents of each thereof. The nucleic acid coding sequence of the CLN3 gene product (e.g., SEQ ID NO: 11) and equivalents thereof are operatively linked to regulatory components in a manner that permits transgene transcription, translation, and expression in a cell of a target tissue.

The AAV sequences of the vector typically comprise the cis-acting 5' and 3' inverted terminal repeat sequences (see, e.g., Carter (1990) In *Handbook of Parvoviruses,* ed., P. Tijsser, CRC Press, pp. 155-1.68). The ITR sequences are typically about 145 bp in length. In certain embodiments substantially the entire sequences encoding the ITRs are used in the vector although some degree of modification of these sequences is permissible. The ability to modify these ITR sequences is within the skill of the art (see, e.g., Sambrook et al. (1989) *Molecular Cloning. A Laboratory Manual,* 2d ed., Cold Spring Harbor Laboratory, New York; and Fisher et al. (1996) *J. Virol.,* 70: 520-532, and the like). An example of such a molecule is a "cis-acting" plasmid containing the transgene, in which the selected transgene sequence and associated regulatory elements are flanked by the 5' and 3' AAV ITR sequences. The AAV ITR sequences may be obtained from any known AAV, including presently identified mammalian AAV types.

In addition to the major elements identified above for the recombinant AAV vector, in certain embodiments, the vector can also typically include conventional control elements that are operably linked to the transgene in a manner that permits its transcription, translation and expression in a cell transfected with the plasmid vector or infected with the AAV virus. Expression control sequences include, for example, appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters which are native, constitutive, inducible and/or tissue-specific, are known in the art and may be utilized.

For nucleic acid encoding proteins, a polyadenylation sequence generally is inserted following the transgene sequences and before the 3' AAV ITR sequence. Suitable polyadenylation sequences include, but are not limited to bovine growth hormone polyadenylation sequence (e.g., nucleotides 3052 to 3198 of SEQ ID NO: 2, SV40 late polyadenylation sequence, SV40 early polyadenylation sequence, AATAAA (SEQ ID NO: 3) polyadenylation signal, CAATAAA (SEQ ID NO: 4) polyadenylation signal, ATTAAA (SEQ ID NO: 5) polyadenylation signal, TANA (SEQ ID NO: 6) polyadenylation signal.

In certain embodiments an AAV vector also contains an intron, desirably located between the promoter/enhancer sequence and the transgene. One illustrative, but non-limiting possible intron sequence is derived from SV-40, and is referred to as the SV-40 T intron sequence. Other intron sequences are known to those of skill in the art and include, inter alia, CBA, and CBA-MVM. (see, e.g., Gray et al. (2011) *Hum. Gene Ther.* 22(9):1143-1153 and references cited within).

Another element that can optionally be present is a post-translational regulatory element. Illustrative, post-translational regulatory elements include, but are not limited to Woodchuck Post-transcriptional Regulatory Element (WPRE), WPRE2 containing a minimal gamma element and a partial alpha-beta element, WPRE3 and containing minimal gamma and alpha elements (see, e.g., Choi et al. (2014) *Molecular Brain* 7: 17-26). Non-limiting examples are provided in the attached sequence listing, and incorporated herein by reference.

The precise nature of the regulatory sequences needed for gene expression in host cells may vary between species, tissues or cell types, but shall in general include, as necessary, 5' non-transcribed and 5' non-translated sequences involved with the initiation of transcription and translation respectively, such as a TATA box, capping sequence, CAAT sequence, enhancer elements, and the like. Especially, such 5' non-transcribed regulatory sequences will include a promoter region that includes a promoter sequence for transcriptional control of the operably joined gene. Regulatory sequences may also include enhancer sequences or upstream activator sequences as desired. The vectors may optionally include 5' leader or signal sequences. Examples of such signal peptides include the albumin, the β-glucuronidase, the alkaline protease or the fibronectin secretory signal peptides. In one aspect, the enhancer is a Woodchuck post-regulatory element ("WPRE") (see, e.g., Zufferey, R. et al. (1999) J. Virol. 73(4):2886-2992). Non-limiting examples of WPREs include SEQ ID NO: 37 or SEQ ID NO: 38. The enhancer element can be downstream of the promoter and CLN3 gene. However, the enhancer can be in any location. Non-limiting examples are provided in the attached sequence listing, and incorporated herein by reference.

Examples of suitable promoters include, but are not limited to the retroviral *Rous sarcoma virus* (RSV) LTR promoter (optionally with the RSV enhancer) (e.g., SEQ ID No: 28 and equivalents thereof), the *cytomegalovirus* (CMV) promoter (optionally with the CMV enhancer) (see, e.g., Boshart et al (1985) *Cell,* 41:521-530 and e.g., SEQ ID No: 27 and equivalents thereof), the SV40 promoter (e.g., SEQ ID No: 29), the dihydrofolate reductase promoter, the β-actin promoter (e.g., chicken β-actin promoter) (e.g., SEQ ID No: 22, SEQ ID No: 23, and equivalents thereof), the phosphoglycerol kinase (PGK) promoter (e.g., SEQ ID No: 30 and equivalents thereof), the EF1α promoter (e.g., SEQ ID No: 31 and equivalents thereof), the CBA promoter (e.g., SEQ ID No: 24 and equivalents thereof), UBC promoter (e.g., SEQ ID No: 34 and equivalents thereof), GUSB promoter, NSE promoter (e.g., SEQ ID No: 33 and equivalents thereof), Synapsin promoter (e.g., SEQ ID No: 32 and equivalents thereof), MeCP2 (methyl-CPG binding protein 2) promoter (e.g., SEQ ID No: 22, SEQ ID No: 23, and equivalents thereof), GFAP; CBh promoter and the like. It is contemplated that different promoters may be used to augment the expression level of the transgene (e.g., CLN3). For example, a chicken β-actin promoter (CBA) may result in strong, ubiquitous expression of the transgene, while a MeCP2 promoter may result in lower expression of the transgene as compared to another promoter. In some embodiments, the promoter may control transgene expression in a tissue-dependent manner. For example, promoter activity may be higher in neurons as compared to glia. In some embodiments, the promoter may control transgene expression in a developmental stage-dependent manner. For example, promoter-driven expression may rise postnatally and be essential throughout adult life.

In certain embodiments the native promoter, or fragment thereof, for the transgene can be used. The native promoter may be preferred when it is desired that expression of the transgene should mimic the native expression. In certain embodiments, other native expression control elements, such as enhancer elements, polyadenylation sites or Kozak consensus sequences may also be used to mimic the native expression.

In some embodiments, the regulatory sequences impart tissue-specific gene expression capabilities. In some cases, the tissue-specific regulatory sequences bind tissue-specific transcription factors that induce transcription in a tissue specific manner. Such tissue-specific regulatory sequences (e.g., promoters, enhancers, etc.) are well known in the art. Exemplary tissue-specific regulatory sequences include, but are not limited to the following tissue specific promoters: neuronal such as neuron-specific enolase (NSE) promoter (Anderson et al. (1993) *Cell. Mol. Neurobiol.,* 13: 503-515) neurofilament light-chain gene promoter (Piccioli et al. (1991) *Proc. Natl. Acad. Sci. USA,* 88: 5611-5615 and e.g., GenBank Accession No: L04147.1 (SEQ ID No:25)), and the neuron-specific vgf gene promoter (Piccioli et al. (1995) *Neuron,* 15: 373-384 and GenBank Accession No: Y09938.1 (SEQ ID No:26)). In some embodiments, the tissue-specific promoter is a promoter of a gene selected from: neuronal nuclei (NeuN), glial fibrillary acidic protein (GFAP) (Brenner et al. (1994) *J. Neurosci.* 14(3):1030-1037), adenomatous polyposis coli (APC), and ionized calcium-binding adapter molecule 1 (Iba-1). In some embodiments, the promoter is a chicken Beta-actin promoter (e.g., SEQ ID No: 24 or equivalents thereof) or an MeCP2 promoter (e.g., nucleotides 775 to 1511 of SEQ ID No: 2, SEQ ID No: 22, SEQ ID No: 23, or equivalents thereof).

In some embodiments, one or more binding sites for one or more of miRNAs are incorporated in a transgene of an AAV vector, to inhibit the expression of the transgene in one or more tissues of a subject harboring the transgenes, e.g., non-CNS tissues. The skilled artisan will appreciate that binding sites may be selected to control the expression of a transgene in a tissue specific manner. For example, expression of a transgene in the liver may be inhibited by incorporating a binding site for miR-122 such that mRNA expressed from the transgene binds to and is inhibited by miR-122 in the liver. Expression of a transgene in the heart may be inhibited by incorporating a binding site for miR-133a or miR-1, such that mRNA expressed from the transgene binds to and is inhibited by miR-133a or miR-1 in the heart. The miRNA target sites in the mRNA may be in the 5' UTR, the 3' UTR or in the coding region. Typically, the target site is in the 3' UTR of the mRNA. Furthermore, the transgene may be designed such that multiple miRNAs regulate the mRNA by recognizing the same or multiple sites. The presence of multiple miRNA binding sites may result in the cooperative action of multiple RISCs and provide highly efficient inhibition of expression. In certain embodiments the target site sequence may comprise a total of 5-100, 10-60, or more nucleotides. In certain embodiments the target site sequence may comprise at least 5 nucleotides of the sequence of a target gene binding site.

The CLN3 Transgene

Ceroid-lipofuscinosis neuronal 3 (CLN3) is a hydrophobic, transmembrane protein found in the cellular membranes of multiple cellular structures, including lysosomal membranes, but molecular function of CLN3 is unknown. CLN3 has been implicated in several cellular processes, including endocytosis and intracellular protein trafficking, lysosomal homeostasis, autophagy, mitochondrial function, amino acid transport, oxidative stress, neuronal excitotoxicity, and cell cycle regulation. CLN3 is known to be important for the normal function of lysosomes—compartments within the cell that normally break down toxic substances and recycle any reusable components.

More than 60 mutations in the CLN3 gene have been identified in people with Batten disease. The most common mutation for Juvenile Batten Disease is an approximately 1 kb nucleotide deletion in the CLN3 gene. It is estimated that more than 90% of individuals with Juvenile Batten disease have such mutation. To study the disease, several animal models have been derived, including a CLN3 knockout (KO) Mice and a CLN3$^{\Delta ex7/8}$ mouse (recapitulates the primary mutation observed in children).

As noted above, the constructs contemplated herein include a polynucleotide sequence that encodes human CLN3 (see, e.g., International Batten Disease Consortium (1995) *Cell*, 82:949-957, and GenBank Accession No: AAC05337 (SEQ ID NO:1)) and equivalents thereof. In some embodiments, the polynucleotide sequence is a CLN3 cDNA. It will be recognized, however, that the nucleic acid sequence encoding CLN3 may be altered, for example to facilitate construction of an expression cassette, to enhance expression (e.g., via coding optimization), and the like. In certain embodiments the encoded CLN3 peptide may be modified, e.g., to improve membrane insertion, to improve activity and/or stability, to reduce immunogenicity, and the like. In certain embodiments a non-human CLN3 may be utilized, particular for application of the AAV to a non-human subject for treatment or research purposes. It is noted that CLN3 sequences are known for a number of mammals including, but not limited to *Canus lupus* (e.g., GenBank Accession No: AAB05546.1 (SEQ ID NO: 7)), *Mus musculus* (e.g., GenBank Accession No: AAB69983 (SEQ ID NO: 8)), *Ovis aries* (e.g., GenBank Accession No: XP_011959725 (SEQ ID NO: 9)), *Felis catus* (e.g., GenBank Accession No: BAM42890 (SEQ ID NO: 10)), and the like.

In some embodiments, a suitable CLN3 nucleic acid sequence comprises, or alternatively consist essentially of, or yet further consist of, a nucleotide sequence encoding a CLN3 polypeptide, wherein the CLN3 polypeptide comprises SEQ ID NO.: 1, or an equivalent polypeptide, wherein an equivalent comprises an amino acid sequence having at least about 80%, at least about 85%, at least about 90%, at least about 95%, at least about 99%, or 100% amino acid sequence identity of SEQ ID NO 1. Additional non-limiting examples are provided in the attached sequence listing, incorporated herein by reference.

The nucleic acid encoding CLN3 or an equivalent thereof can comprise, or alternatively consist essentially of, or yet further consist of, the polynucleotide of SEQ ID NO: 11, or a biological equivalent thereof. An example of a biological equivalent of CLN3 nucleic acid comprises a nucleic acid that hybridizes under conditions of high stringency to the complement of SEQ ID NO: 11 and encodes a protein having CLN3 biological activity. Another example includes a nucleic acid having at least 80% sequence identity to SEQ ID NO: 11 or its complement and encodes a protein having CLN3 biological activity. It is noted that human CLN3 variants are known in the art. Non-limiting examples include, GenBank Accession No: NM_001042432.1 (CLN3, transcript variant 1); GenBank Accession No: NM_001286104.1 (CLN3, transcript variant 3); GenBank Accession No: NM_001286105.1 (CLN3, transcript variant 4); GenBank Accession No: NM_001286109.1 (CLN3, transcript variant 5); GenBank Accession No: NM_001286110.1 (CLN3, transcript variant 6) or a nucleic acid having at least 80% sequence identity to any one of the examples listed above, or its complement, and encodes a protein having CLN3 biological activity.

In some embodiments, expression of the CLN3 transgene is driven by the retroviral *Rous sarcoma virus* (RSV) LTR promoter (optionally with the RSV enhancer). In some embodiments, expression of the CLN3 transgene is driven by the *cytomegalovirus* (CMV) promoter (optionally with the CMV enhancer). In some embodiments, expression of the CLN3 transgene is driven by the SV40 promoter. In some embodiments, expression of the CLN3 transgene is driven by the dihydrofolate reductase promoter. In some embodiments, expression of the CLN3 transgene is driven by the β-actin promoter. In some embodiments, expression of the CLN3 transgene is driven by the PGK promoter. In some embodiments, expression of the CLN3 transgene is driven by the EF1α promoter. In some embodiments, expression of the CLN3 transgene is driven by the UBC promoter. In some embodiments, expression of the CLN3 transgene is driven by the GUSB promoter. In some embodiments, expression of the CLN3 transgene is driven by the NSE promoter. In some embodiments, expression of the CLN3 transgene is driven by the Synapsin promoter. In some embodiments, expression of the CLN3 transgene is driven by MeCP2 promoter. In some embodiments, expression of the CLN3 transgene is driven by the GFAP promoter. In some embodiments, expression of the CLN3 transgene is driven by the CBh promoter. In preferred embodiments, expression of the CLN3 transgene is driven by the CBA promoter (e.g., SEQ ID NO: 24) or an equivalent thereof. In more preferred embodiments, expression of the CLN3 transgene is driven by the MeCP2promoter (e.g., nucleotides 775 to 1511 of SEQ ID No: 2, SEQ ID NO: 22 or SEQ ID NO: 23) or an equivalent of each thereof. In some embodiments, any one of the above mentioned promoters may be expressly excluded from driving expression of the CLN3 transgene.

Production of Recombinant AAV (rAAV)

In some embodiments, the AAV genome is from a naturally derived serotype or an isolate or a clade of AAV. In some embodiments, the AAV serotype is selected from the group of AAV1, AAV2, AAV4, AAV5, AAV6, AAV8, or AAV9. In some embodiments, the AAV serotype is AAV9. In other embodiments, the AAV serotype is AAV2.

Non-limiting examples include, the recombinant AAV can comprise, or alternatively consist essentially of, or yet further consist of, the polynucleotide of GenBank Accession No: AF063497.1 (AAV1, complete genome); the polynucleotide of GenBank Accession No: NC_001401.2 (AAV2, complete genome); the polynucleotide of GenBank Accession No: NC_001829 (AAV4, complete genome); the polynucleotide of GenBank Accession No: AX256321.1 (AAV5, synthetic construct); the polynucleotide of GenBank Accession No: AF028704.1 (AAV6, complete genome); the polypeptide of SEQ ID No: 35, the polynucleotide of SEQ ID No: 36, or a biological equivalent thereof. Another example includes a nucleic acid having at least 80% sequence identity to the above referenced polynucleotides.

A suitable recombinant *adeno-associated virus* (AAV) can be generated by culturing a host cell that contains a nucleic acid sequence encoding an *adeno-associated virus* (AAV) serotype capsid protein, or fragment thereof, a functional rep gene; a minigene composed of at a minimum, AAV inverted terminal repeats (ITRs) and the nucleic acid sequence encoding the CLN3 polypeptide (or variants or equivalents thereof as described herein), and sufficient helper functions to permit packaging of the minigene into the AAV capsid protein.

The components to be cultured in the host cell to package an AAV vector in an AAV capsid may be provided to the host cell in trans. Alternatively, any one or more of the required components (e.g., recombinant AAV vector, rep sequences, cap sequences, and/or helper functions) may be provided by a stable host cell which has been engineered to contain one or more of the required components using methods known to those of skill in the art. Most suitably, such a stable host cell will contain the required component(s) under the control of an inducible promoter. However, in certain embodiments, the required component(s) may be under the control of a constitutive promoter.

In still another alternative, a selected stable host cell may contain selected component(s) under the control of a constitutive promoter and other selected component(s) under the control of one or more inducible promoters. For example, a stable host cell may be generated which is derived from 293 cells (which contain E1 helper functions under the control of a constitutive promoter), but which contain the rep and/or cap proteins under the control of inducible promoters. Still other stable host cells may be generated by one of skill in the art.

The recombinant AAV vector, rep sequences, cap sequences, and helper functions required for producing the rAAV may be delivered to the packaging host cell using any appropriate genetic element (vector). The selected genetic element may be delivered by any suitable method, including those described herein. Such methods are known to those with skill in the art (see, e.g., Sambrook et al, Molecular Cloning: A Laboratory Manual, Cold Spring Harbor Press, Cold Spring Harbor, N.Y.). Similarly, methods of generating rAAV virions are well known (see, e.g., Fisher et al. (1993) *J. Virol.,* 70: 520-532; U.S. Pat. No. 5,478,745; and the like).

In one illustrative, but non-limiting embodiment, rAAVs may be produced using the triple transfection method (e.g., as described in detail in U.S. Pat. No. 6,001,650). Typically, the recombinant AAVs are produced by transfecting a host cell with a recombinant AAV vector (comprising a transgene) to be packaged into AAV particles, an AAV helper function vector, and an accessory function vector. An AAV helper function vector encodes the "AAV helper function" sequences (i.e., rep and cap), which function in trans for productive AAV replication and encapsidation. Typically, the AAV helper function vector supports efficient AAV vector production without generating any detectable wild-type AAV virions (i.e., AAV virions containing functional rep and cap genes). Illustrative, but non-limiting examples of vectors include pHLP19 (see U.S. Pat. No. 6,001,650), pRep6cap6 vector (see, e.g. U.S. Pat. No. 6,156,303), and the like. The accessory function vector can encode nucleotide sequences for non-AAV derived viral and/or cellular functions upon which AAV is dependent for replication (i.e., "accessory functions"). The accessory functions can include those functions required for AAV replication, including, without limitation, those moieties involved in activation of AAV gene transcription, stage specific AAV mRNA splicing, AAV DNA replication, synthesis of cap expression products, and AAV capsid assembly. Viral-based accessory functions can be derived from any of the known helper viruses such as *adenovirus, herpesvirus* (other than *herpes simplex virus type*-1), and *vaccinia virus*.

Recombinant AAV Administration

The rAAVs are typically administered in sufficient amounts to transfect the cells of a desired tissue and to provide sufficient levels of gene transfer and expression without undue adverse effects. Conventional and pharmaceutically acceptable routes of administration include, but are not limited to, direct delivery to the selected tissue (e.g., intracerebral administration, intrathecal administration), intravenous, oral, aerosol administration, administration via inhalation (including intranasal and intratracheal delivery), intravenous, intramuscular, subcutaneous, intradermal, rectal, and other parental routes of administration. Routes of administration may be combined, if desired.

In certain embodiments delivery of certain rAAVs to a subject may be, for example, by administration into the bloodstream of the subject. Administration into the bloodstream may be by injection into a vein, an artery, or any other vascular conduit. Moreover, in certain instances, it may be desirable to deliver the rAAVs to brain tissue, meninges, neuronal cells, glial cells, astrocytes, oligodendrocytes, cerebrospinal fluid (CSF), interstitial spaces and the like. In some embodiments, recombinant AAVs may be delivered directly to the spinal cord or brain by injection into the ventricular region, as well as to the striatum (e.g., the caudate nucleus or putamen of the striatum), and neuromuscular junction, or cerebellar lobule, with a needle, catheter or related device, using neurosurgical techniques known in the art, such as by stereotactic injection (see, e.g., Stein et al. (1999) *J Virol.* 73: 3424-3429; Davidson et al. (2000) *Proc. Natl. Acad. Sci. USA*; Davidson et al. (1993) *Nat. Genet.* 3:219-223; Alisky and Davidson (2000) *Hum. Gene Ther.* 11: 2315-2329; and the like).

Methods for delivering a transgene to central nervous system (CNS) tissue in a subject are provided herein. The methods typically involve administering to a subject an effective amount of a rAAV comprising a nucleic acid vector for expressing a transgene (e.g., CLN3) in the subject. An effective amount refers to an amount that is capable of treating or ameliorating juvenile neuronal ceroid lipofuscinosis (JNCL or Juvenile Batten disease) and/or reducing, suppressing, inhibiting, lessening, ameliorating or affecting the progression, severity, and/or scope of the disease or condition.

The effective amount will depend on a variety of factors such as, for example, the species, age, weight, health of the subject, and the CNS tissue to be targeted, and may thus vary among subject and tissue. An effective amount may also depend on the mode of administration. For example, targeting a CNS tissue by intravascular injection may require different (e.g., higher) doses, in some cases, than targeting CNS tissue by intrathecal or intracerebral injection. In some cases, multiple doses of a rAAV are administered while in other cases, as illustrated in the examples herein, a single dose can be sufficient. An effective amount may also depend on the rAAV used. For example, dosages for targeting a CNS tissue may depend on the serotype (e.g., the capsid protein) of the rAAV. For example, the rAAV may have a capsid protein of an AAV serotype selected from the group consisting of: AAV1, AAV2, AAV5, AAV6, AAV6.2, AAV7, AAV8, AAV9, rh.10, rh.39, rh.43 and CSp3. In certain embodiments, the effective amount of rAAV is $10^{10}$, $10^{11}$, $10^{12}$, $10^{13}$, or $10^{14}$, or $10^{15}$, or $10^{16}$ genome copies per kg. In certain embodiments, the effective amount of rAAV is $10^{10}$, $10^{11}$, $10^{12}$, $10^{13}$, or $10^{14}$, or $10^{15}$, or $10^{16}$ genome copies per subject. When multiple doses are administered, the same or different serotype can be combined for the therapy.

A method for delivering a transgene to CNS tissue in a subject may comprise administering a rAAV by a single route or by multiple routes. For example, delivering a transgene to CNS tissue in a subject may comprise administering to the subject, by intravenous administration, an effective amount of a rAAV that crosses the blood-brain-barrier. Delivering a transgene to CNS tissue in a subject may comprise administering to the subject an effective amount of a rAAV by intrathecal administration or intracerebral administration, e.g., by intraventricular injection. A method for delivering a transgene to CNS tissue in a subject may comprise co-administering of an effective amount of a rAAV by two different administration routes, e.g., by intrathecal administration and by intracerebral to administration. Co-administration may be performed at approximately the same time, or different times.

In certain embodiments the CNS tissue to be targeted may be selected from cortex, hippocampus, thalamus, hypothalamus, cerebellum, brain stem, cervical spinal cord, thoracic spinal cord, and lumbar spinal cord, for example. The administration route for targeting CNS tissue typically depends on the AAV serotype as discussed above.

In certain embodiments, it may be desirable to first perform diagnostic confirmation of a presumed subject (or for carrier or prenatal testing) to identify mutations in the CLN3 gene prior to administering to the subject an effective amount of a AAV comprising a nucleic acid vector for expressing a transgene (e.g., CLN3) in the subject. Such testing can, for example, be done by PCR amplification and sizing analysis for the common 1 kb deletion or by full sequencing analysis to cover the 15 exons of the CLN3 gene, as well as adjacent intronic regions. Sequencing can uncover any nonsense, missense, splicing mutations, small insertion and deletion mutations which have all been reported in the CLN3 gene.

In certain circumstances it will be desirable to deliver the rAAV-based therapeutic constructs in suitably formulated pharmaceutical compositions disclosed herein either subcutaneously, intrapancreatically, intranasally, parenterally, intravenously, intramuscularly, intracerebrally, intrathecally, intracerebrally, orally, intraperitoneally, or by inhalation. In some embodiments, the administration modalities as described in U.S. Pat. Nos. 5,543,158; 5,641,515 and 5,399,363 may be used to deliver rAAVs.

In some embodiments, the vectors, recombinant *adeno-associated virus*, pharmaceutical formulations, and the like described herein can be administered with an additional therapeutic. Non-limiting examples of additional therapeutics include, mycophenolate mofetil, carbenoxolene, glycyrrhetinic acid, glycyrrhizic acid, chaperone therapy, enzyme replacement therapy, stem cell therapy, anticonvulsant medications, antioxidant supplementation (e.g., vitamin C, vitamin E, methionine, B6), omega-3 fatty acids. (see, e.g., Hobert et al., (2006) *Biochimica et Biophysica Acta* 1762 (10):945-953). Dosage, treatment protocol, and routes of administration for additional therapeutics are known in the art and/or within the ability of a skilled clinician to determine, based on the type of treatment, etc.

In one embodiment, the vectors, recombinant *adeno-associated virus*, pharmaceutical formulations, and the like described herein and the additional therapeutic are administered sequentially. In another embodiment, the vectors, recombinant *adeno-associated virus*, pharmaceutical formulations, and the like described herein and the additional therapeutic are administered simultaneously. In one embodiment, the vectors, recombinant *adeno-associated virus*, pharmaceutical formulations, and the like described herein are administered after the period of time of administration of an additional therapeutic. In a further aspect, the rAAV therapy is co-administered with other complimentary therapy to alleviate or treat the symptoms of disease.

Recombinant AAV Compositions

In certain embodiments the rAAVs maybe delivered to a subject in compositions according to any appropriate methods known in the art. For example, the rAAV, suspended in a physiologically compatible carrier (e.g., in a composition), may be administered to a subject, e.g., a human, mouse, rat, cat, dog, sheep, rabbit, horse, cow, goat, pig, guinea pig, hamster, chicken, turkey, or a non-human primate (e.g., Macaque). The compositions may comprise a rAAV alone, or in combination with one or more other viruses (e.g., a second rAAV encoding having one or more different transgenes). In some embodiments, a compositions comprise 1, 2, 3, 4, 5, 6, 7, 8, 9, 10, or more different rAAVs each having one or more different transgenes.

Suitable carriers may be readily selected by one of skill in the art in view of the indication for which the rAAV is directed. For example, one suitable carrier includes saline, which may be formulated with a variety of buffering solutions (e.g., phosphate buffered saline). Other illustrative carriers include, but are not limited to, sterile saline, lactose, sucrose, calcium phosphate, gelatin, dextran, agar, pectin, peanut oil, sesame oil, and water.

Optionally, the compositions of the invention may contain, in addition to the rAAV and carrier(s), other conventional pharmaceutical ingredients, such as preservatives, or chemical stabilizers. Suitable illustrative preservatives include, but are not limited to chlorobutanol, potassium sorbate, sorbic acid, sulfur dioxide, propyl gallate, the parabens, ethyl vanillin, glycerin, phenol; and parachlorophenol. Suitable chemical stabilizers include gelatin and albumin.

In some embodiments, rAAV compositions are formulated to reduce aggregation of AAV particles in the composition, particularly where high rAAV concentrations are present (e.g., about $10^{13}$ vg/ml or more). Methods for reducing aggregation of rAAVs are well known in the art and, include, for example, addition of surfactants, pH adjustment, salt concentration adjustment, etc. (see, e.g., Wright et al. (2005) *Mol. Ther.* 12: 171-178; and the like).

Formulation of pharmaceutically-acceptable excipients and carrier solutions is well-known to those of skill in the art, as is the development of suitable dosing and treatment regimens for using the particular compositions described herein in a variety of treatment regimens. Typically, these formulations may contain at least about 0.1% of the active ingredient or more, although the percentage of the active ingredient(s) may, of course, be varied and may conveniently be, for example, between about 1 or 2% and about 70% or 80% or more of the weight or volume of the total formulation. Naturally, the amount of active ingredient in each therapeutically-useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

The pharmaceutical forms suitable for injectable use typically include sterile aqueous solutions or dispersions and sterile powders for the extemporaneous preparation of sterile injectable solutions or dispersions. Dispersions may also be prepared in glycerol, liquid polyethylene glycols, and mixtures thereof and in oils. Under ordinary conditions of storage and use, these preparations contain a preservative to prevent the growth of microorganisms. In many cases the form is sterile and fluid to the extent that easy syringability exists. The formulation is typically stable under the conditions of manufacture and storage and preserved against the contaminating action of microorganisms, such as bacteria and fungi. In certain embodiments the carrier can be a solvent or dispersion medium containing, for example, water, ethanol, polyol (e.g., glycerol, propylene glycol, and liquid polyethylene glycol, and the like), suitable mixtures thereof, and/or vegetable oils. In certain embodiments proper fluidity may be maintained, for example, by the use of a coating, such as lecithin, by the maintenance of the required particle size in the case of dispersion and by the use of surfactants. In various embodiments the prevention of the action of microorganisms can be brought about by various antibacterial and antifungal agents, for example, parabens, chlorobutanol, phenol, sorbic acid, thimerosal, and the like. In many cases, it will be desirable to include isotonic agents, for example, sugars or sodium chloride. Prolonged absorption of the injectable compositions can be brought about by the use in the compositions of agents delaying absorption, for example, aluminum monostearate and gelatin.

In certain embodiments for administration of an injectable aqueous solution, for example, the solution may be suitably buffered, if necessary, and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art. For example, one dosage may be dissolved in 1 ml of isotonic NaCl solution and either added to 1000 ml of hypodermoclysis fluid or injected at the proposed site of infusion, (see, e.g., "Remington's Pharmaceutical Sciences" 15th Edition, pages 1035-1038 and 1570-1580). Some variation in dosage may occur depending on the condition of the host. In some embodiments, the person responsible for administration will, in any event, determine the appropriate dose for the individual host.

In certain embodiments sterile injectable solutions can be prepared by incorporating the active rAAV in the required amount in the appropriate solvent with various of the other ingredients enumerated herein, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions; illustrative methods of preparation include, but are not limited to vacuum-drying and freeze-drying techniques which yield a powder of the active ingredient plus any additional desired ingredient from a previously sterile-filtered solution thereof.

In certain embodiments the rAAV compositions disclosed herein may also be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Supplementary active ingredients can also be incorporated into the compositions. The phrase "pharmaceutically-acceptable" refers to molecular entities and compositions that do not produce an allergic or similar untoward reaction when administered to a host.

Delivery vehicles such as liposomes, nanocapsules, microparticles, microspheres, lipid particles, vesicles, and the like, may be used for the introduction of the compositions of the present invention into suitable host cells. In particular, the rAAV vector delivered trans genes may be formulated for delivery either encapsulated in a lipid particle, a liposome, a vesicle, a nanosphere, or a nanoparticle or the like.

In certain embodiments such formulations may be used pharmaceutically acceptable formulations of the nucleic acids or the rAAV constructs disclosed herein. The formation and use of liposomes is generally known to those of skill in the art (see, e.g., U.S. Pat. Nos. 5,741,516; 5,567,434; 5,552,157; 5,565,213; 5,738,868; 5,795,587; and the like).

Liposomes have been used successfully with a number of cell types that are normally resistant to transfection by other procedures. In addition, liposomes are free of the DNA length constraints that are typical of viral-based delivery systems. Liposomes have been used effectively to introduce genes, drugs, radiotherapeutic agents, viruses, transcription factors and allosteric effectors into a variety of cultured cell lines and animals. In addition, several successful clinical trials examining the effectiveness of liposome-mediated drug delivery have been completed.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 µm. Sonication of MLVs results in the formation of small unilamellar vesicles (SUVs) with diameters in the range of 200 to 500 angstrom, containing an aqueous solution in the core.

Alternatively, nanocapsule formulations of the rAAV may be used. Nanocapsules can generally entrap substances in a stable and reproducible way. To avoid side effects due to intracellular polymeric overloading, such ultrafine particles (sized around 0.1 µm) can be designed using polymers able to be degraded in vivo. In certain embodiments biodegradable polyalkyl-cyanoacrylate nanoparticles that meet these requirements are contemplated for use.

In addition to the methods of delivery described above, the following techniques are also contemplated as alternative methods of delivering the rAAV compositions to a host. Sonophoresis (i.e., ultrasound) has been used and described in U.S. Pat. No. 5,656,016 as a device for enhancing the rate and efficacy of drug permeation into and through the circulatory system. Other drug delivery alternatives contemplated are intraosseous injection (U.S. Pat. No. 5,779,708), microchip devices (U.S. Pat. No. 5,797,898), ophthalmic formulations, transdermal matrices (U.S. Pat. Nos. 5,770,219 and 5,783,208) and feedback-controlled delivery (U.S. Pat. No. 5,697,899).

Kits and Related Compositions

The agents described herein may, in some embodiments, be assembled into pharmaceutical or diagnostic or research kits to facilitate their use in therapeutic, diagnostic or research applications. A kit may include one or more containers housing the components of the invention and instructions for use. Specifically, such kits may include one or more agents described herein, along with instructions describing the intended application and the proper use of these agents. In certain embodiments agents in a kit may be in a pharmaceutical formulation and dosage suitable for a particular application and for a method of administration of the agents. Kits for research purposes may contain the components in appropriate concentrations or quantities for running various experiments.

The kit may be designed to facilitate use of the methods described herein and can take many forms. Each of the compositions of the kit, where applicable, may be provided in liquid form (e.g., in solution), or in solid form, (e.g., a dry powder). In certain cases, some of the compositions may be constitutable or otherwise processable (e.g., to an active form), for example, by the addition of a suitable solvent or other species (for example, water or a cell culture medium), which may or may not be provided with the kit.

As used herein, "instructions" can define a component of instruction and/or promotion, and typically involve written instructions on or associated with packaging of the invention. Instructions also can include any oral or electronic instructions provided in any manner such that a user will clearly recognize that the instructions are to be associated with the kit, for example, audiovisual (e.g., videotape, DVD, etc.), internet, and/or web-based communications, etc. The written instructions may be in a form prescribed by a governmental agency regulating the manufacture, use or sale of pharmaceuticals or biological products, which instructions can also reflects approval by the agency of manufacture, use or sale for animal administration.

The kit may contain any one or more of the components described herein in one or more containers. As an example, in one embodiment, the kit may include instructions for mixing one or more components of the kit and/or isolating and mixing a sample and applying to a subject. The kit may include a container housing agents described herein. The agents may be in the form of a liquid, gel or solid (powder). The agents may be prepared sterilely, packaged in syringe and shipped refrigerated. Alternatively it may be housed in a vial or other container for storage. A second container may have other agents prepared sterilely. Alternatively the kit may include the active agents premixed and shipped in a syringe, vial, tube, or other container. The kit may have one or more or all of the components required to administer the agents to a subject, such as a syringe, topical application devices, or IV needle tubing and bag.

The therapies as describe herein can be combined with appropriate diagnostic techniques to identify and select patients for the therapy. For example, a sample is isolated from a patient and the sample is tested for a mutation that has been correlated to development of Juvenile Batten Disease (homozygous or heterozygous). Thus, patients harboring the mutation can be identified prior to symptoms appearing or before advancement of the disease.

EXAMPLES

The following examples are offered to illustrate, but not to limit the claimed invention.

Example 1

Gene Therapy for the Treatment of Juvenile Batten Disease

This example describes initial studies of gene therapy for the treatment of Juvenile Batten Disease. While gene therapy has shown promise in correcting forms of Batten Disease that involve mutations in soluble enzymes, in part, due to cross-correction of neighboring non-transduced cells (Passini et al. (2006) *J. Neurosci.* 26(5): 1334-1342; Sondhi et al. (2012) *Hum. Gene Ther. Meth.* 23(5): 324-335; Macauley et al. (2014) *J. Neurosci.* 34(39): 13077-13082), such approaches have been viewed as problematic for the treatment of JNCL because CLN3 is a transmembrane protein (Cotman et al. (2012) *Clin. Lipidol.* 7(1): 79-91), meaning more cells must be transduced to produce a phenotypic effect. However, the data provided herein demonstrate that it is possible to deliver CLN3 to enough cells to improve motor behavior in a mouse model of JNCL.

Low CLN3 expression levels were driven with the promoter for methyl-CpG binding protein 2 (MeCP2) that was previously effective in a dosage-dependent model of Rett syndrome (Garg et al. (2013) *J. Neurosci.* 33(34): 13612-13620), an autism spectrum disorder, with a separate construct driving high levels of CLN3 via the β-actin promoter. The rationale for this approach was based on the prediction that low CLN3 levels are required for normal cellular function, since postnatal CLN3 expression is limited (Eliason et al. (2007) *J. Neurosci.* 27(37): 9826-9834). This study represents the first demonstration of a CLN3 dosage effect in vivo, where it was surprisingly observed that high levels of CLN3 overexpression masked a therapeutic benefit.

As described below, for proof-of-principle studies, 1 month-old $CLN3^{\Delta ex7/8}$ mice received one dose of $2\times10^{12}$ viral genomes (vg) of self-complementary (sc) AAV9/ β-actin-hCLN3 (high expressing) or scAAV9/MeCP2-hCLN3 (low expressing) intravenously, with viruses driving green fluorescence protein (GFP) expression (scAAV9/β-actin-GFP and scAAV9/MeCP2-GFP) as controls (see, FIG. 1). Importantly, a promoter-dosage effect for hCLN3 expression was confirmed in several brain regions where neurons are destined to die in JNCL, including the hippocampus (HPC), striatum (STR), thalamus (TH), visual cortex (VC), and cerebellum (CB), where hCLN3 levels were elevated from 3- to 8-fold in $CLN3^{\Delta ex7/8}$ mice receiving scAAV9/ β-actin-hCLN3 vs. scAAV9/MeCP2-hCLN3.

Figure 7A:
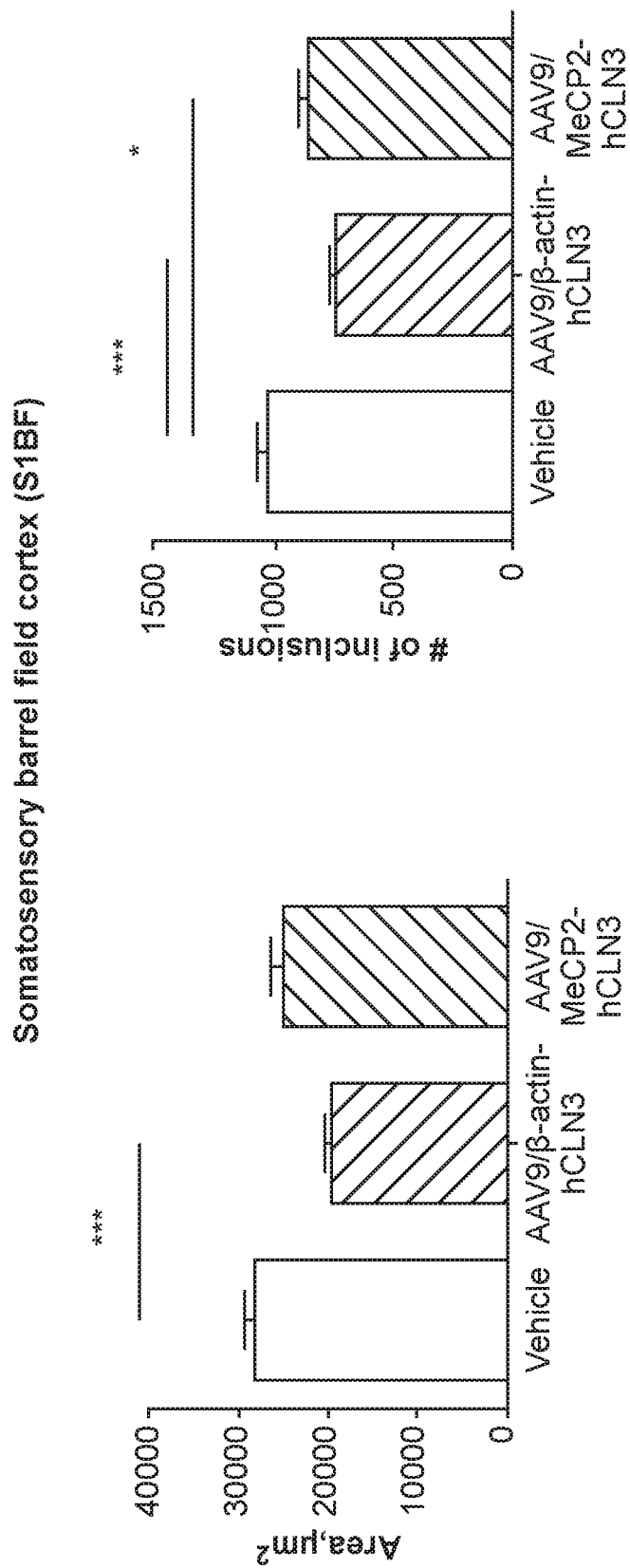
FIGS. 7A-7G show that CLN3 replacement reduces lysosomal inclusions. One month-old CLN3$^{\Delta ex7/8}$ mice (4/group) received one i.v. injection of 2×10$^{12}$ vg scAAV9/β-actin-hCLN3 or scAAV9/MeCP2-hCLN3, whereupon lysosomal inclusions were quantitated 5 months later in somatosensory barrel field cortex (S1BF) (FIG. 7A), striatum (STR) (FIG. 7B), visual cortex (VC) (FIG. 7C), thalamus (TH) (FIG. 7D), hippocampus (HP) (FIG. 7E), cerebellum (CB) (FIG. 7F) by quantitative confocal microscopy. *, p<0.05. A summary of the comparison of vehicle and MeCP2-hCLN3 in S1BF, VC, and TH is shown in FIG. 7G).
Figure 7B:
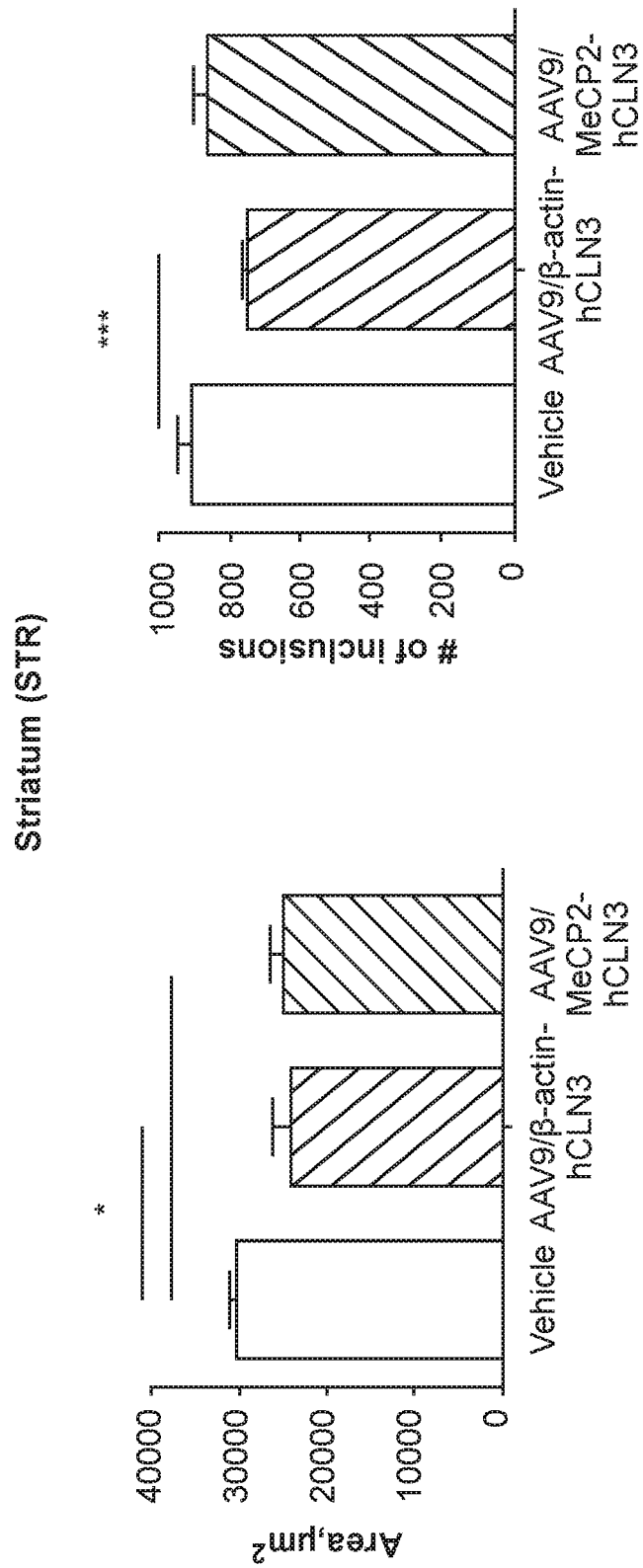
Figure 7C:
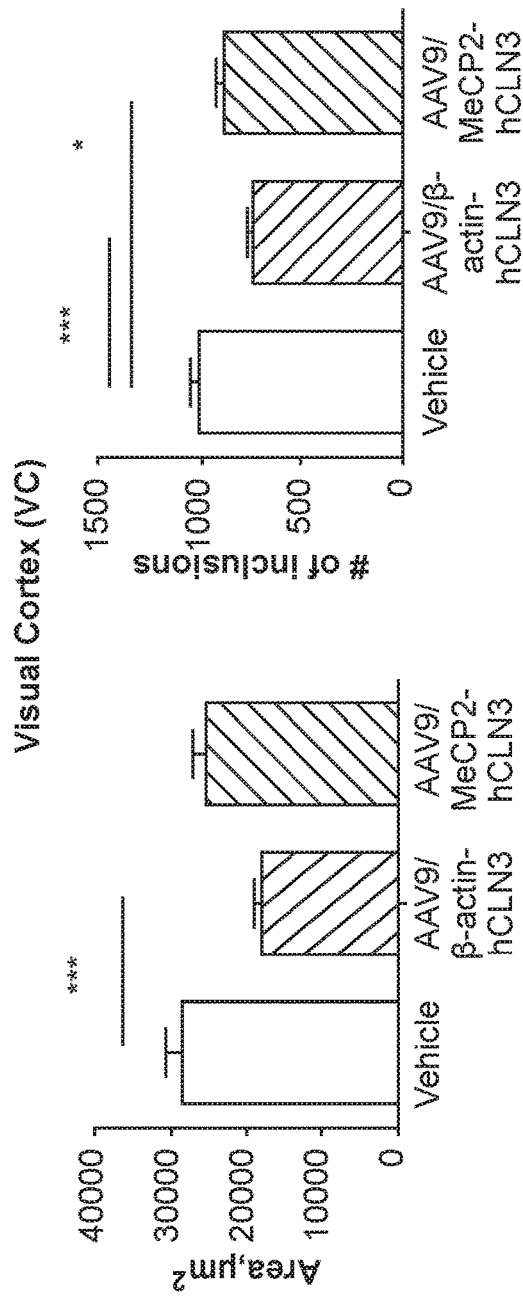
Figure 7D:
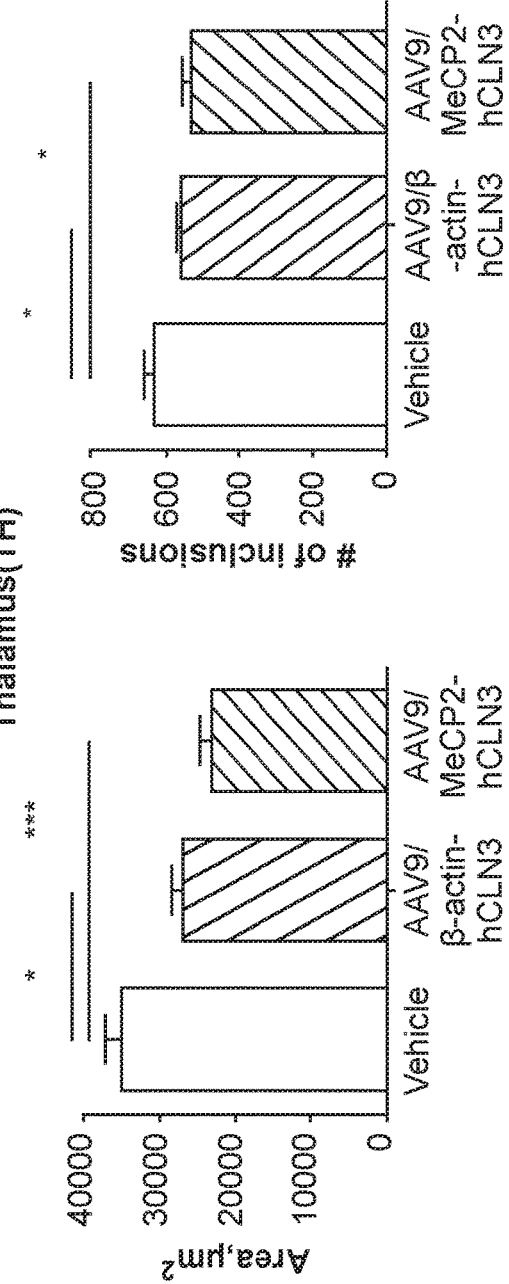
Figure 7E:
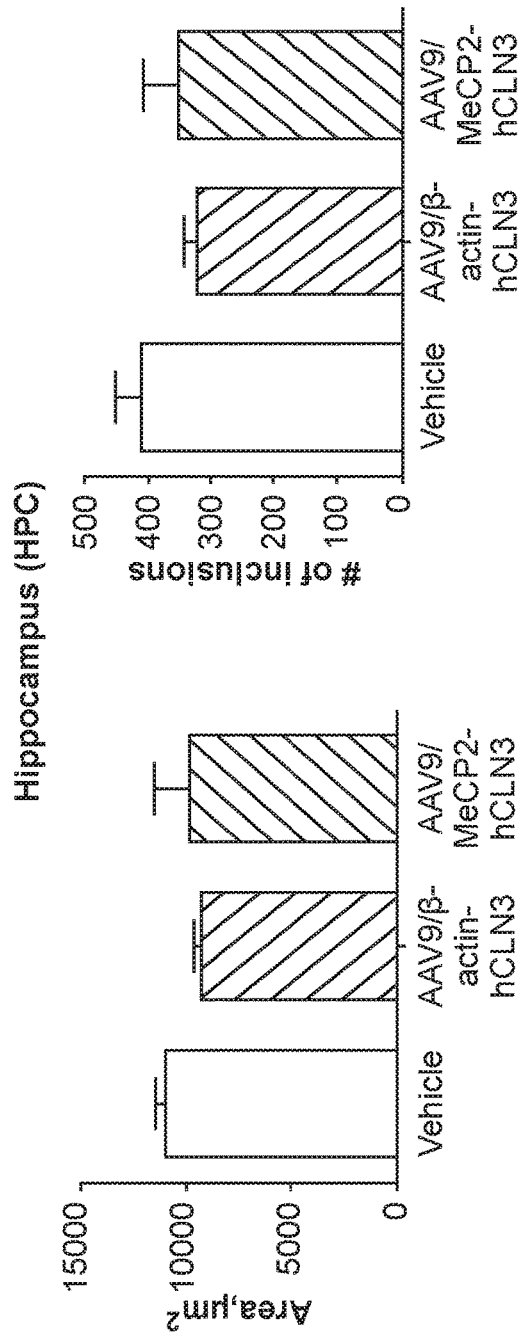
Figure 7F:
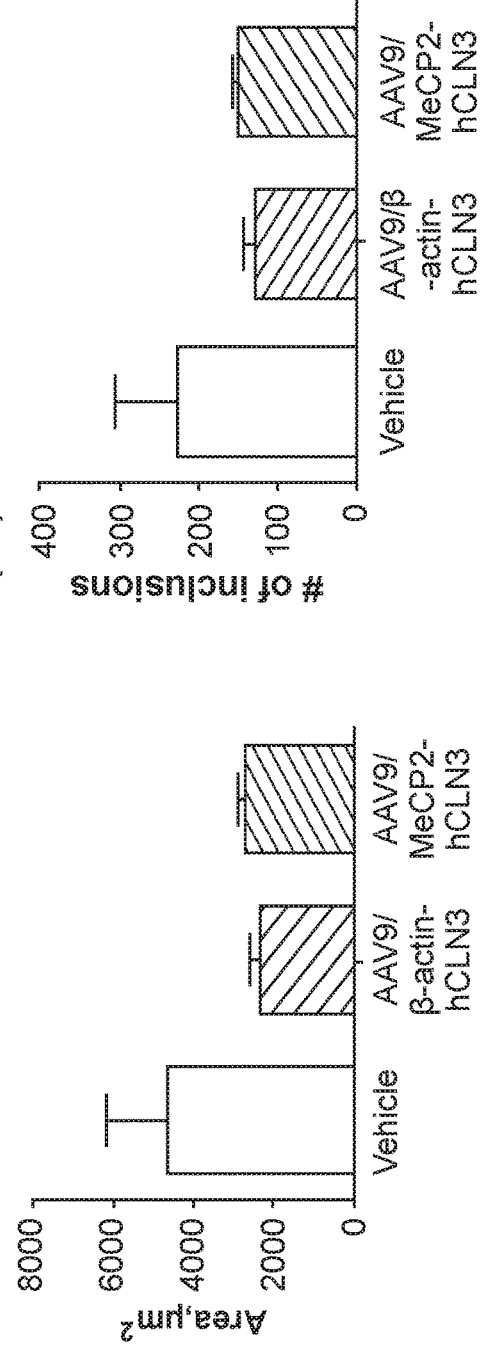
Figure 7G:
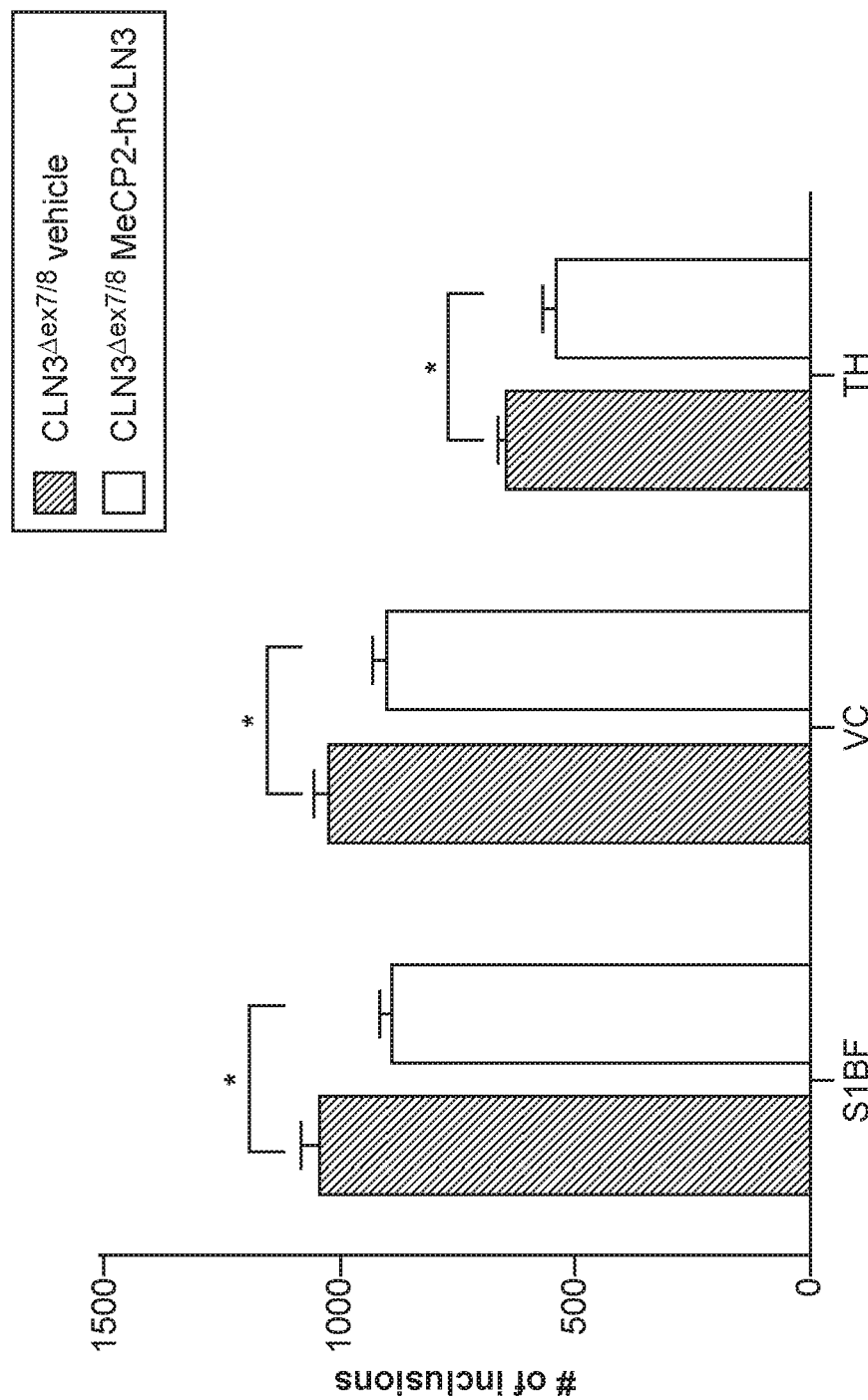

However, there was a disconnect between hCLN3 levels and neuroprotection, since only the scAAV9 construct driving low hCLN3 expression (scAAV9/MeCP2-hCLN3) was capable of correcting motor deficits in $CLN3^{\Delta ex7/8}$ mice (accelerating rotarod and pole descent), demonstrating the surprising result that high CLN3 expression in the brain was not advantageous for improved motor coordination. (see, FIG. 2A-2E). Similar benefits were observed with lysosomal storage material, which was significantly reduced in the somatosensory barrel field cortex (S1BF) (see, FIG. 7A), VC (see, FIG. 7C), and TH (see, FIG. 7D) of animals receiving scAAV9/MeCP2-hCLN3.

The beneficial effects of scAAV9/MeCP2-hCLN3 on motor behavior in CLN3$^{\Delta ex7/8}$ mice were not observed with scAAV9/GFP control constructs, confirming specificity of action for hCLN3 (see, FIG. 2A-2E). The extent of viral transduction in the brain was widespread, as evident by GFP expression in the S1BF, VC, STR, TH, HPC, and CB (see, FIG. 4). scAAV9/MeCP2-hCLN3 transduced NeuN$^+$ neurons and GFAP$^+$ astrocytes in 1 month-old CLN3$^{\Delta ex7/8}$ mice, whereas limited expression was detected in microglia (see, FIG. 6A-6C). Although wild type CLN3 expression was only restored in a subset of neurons and glia, this was sufficient to correct disease-associated pathology in CLN3$^{\Delta ex7/8}$ animals (as measured by improved motor function and decreased lysosomal storage material). Without wishing to be bound by theory, it is contemplated that this may reflect the redundancy of cells in behavioral circuits or compensation by other mechanisms to supplant circuits weakened by insufficient neuronal/glial CLN3, and/or may reflect an underestimate in the number of cells that are transduced.

Based on these observations, it is believed that scAAV9/MeCP2-hCLN3 gene therapy will target sufficient numbers of CNS cells to significantly improve JNCL outcome.

Methods and Results

Self-complementary AAV9 (scAAV9) persists as a stable episome in non-dividing cells with studies reporting stable transgene expression for years. scAAV9 vectors are 10- to 100-fold more efficient than traditional single-stranded (ss) AAV vectors (McCarty et al. (2003) *Gene Ther.* 10(26): 2112-2118; McCarty et al. (2001) *Gene Ther.* 8(16): 1248-1254), but can only package foreign DNA <2.2 kb, which was not a limitation for the approach described herein, since the hCLN3 cDNA is only 1.3 kb. The scAAV9 constructs were engineered to harbor hCLN3 to facilitate its translational potential (see, e.g., FIG. 1). In certain constructs the methylCpG binding protein 2 (MeCP2) promoter was selected to drive hCLN3 expression.

Figure 2A:
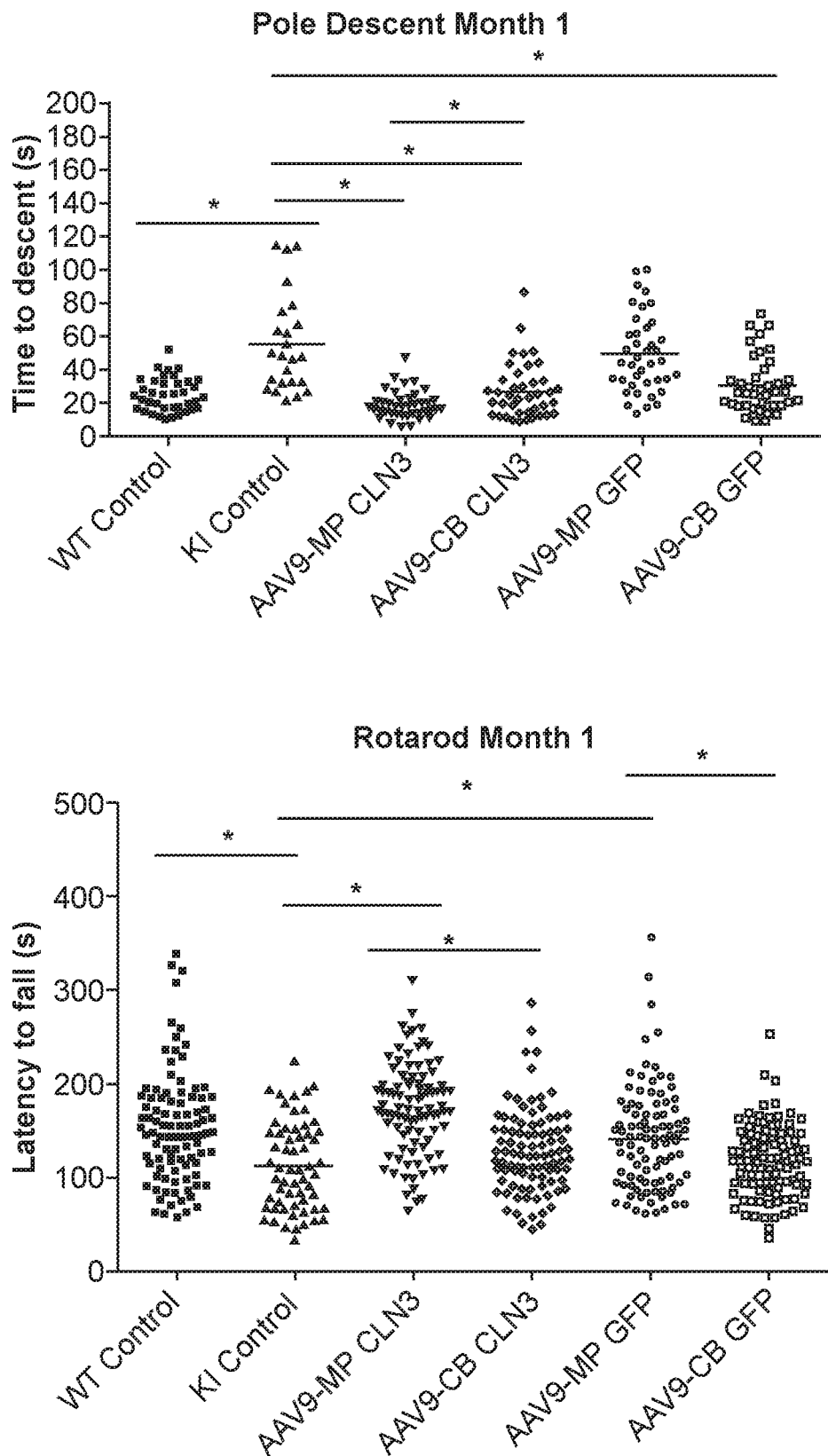
FIG. 2A-FIG. 2F, show that CLN3 replacement using scAAV9/MeCP2-hCLN3 improves motor behaviors in CLN3$^{\Delta ex7/8}$ mice. One month-old CLN3$^{\Delta ex7/8}$ mice (8/group) received one i.v. injection of 2×10$^{12}$ viral genomes (vg) of scAAV9/MeCP2-hCLN3, scAAV9/ β-actin-hCLN3, or GFP expressing viruses as controls, whereupon accelerating rotarod and pole descent tests were performed at 1 month (FIG. 2A), 2 months (FIG. 2B), 3 months (FIG. 2C), 4 months (FIG. 2D), and 5 months (FIG. 2E). *, p<0.05.
Figure 2B:
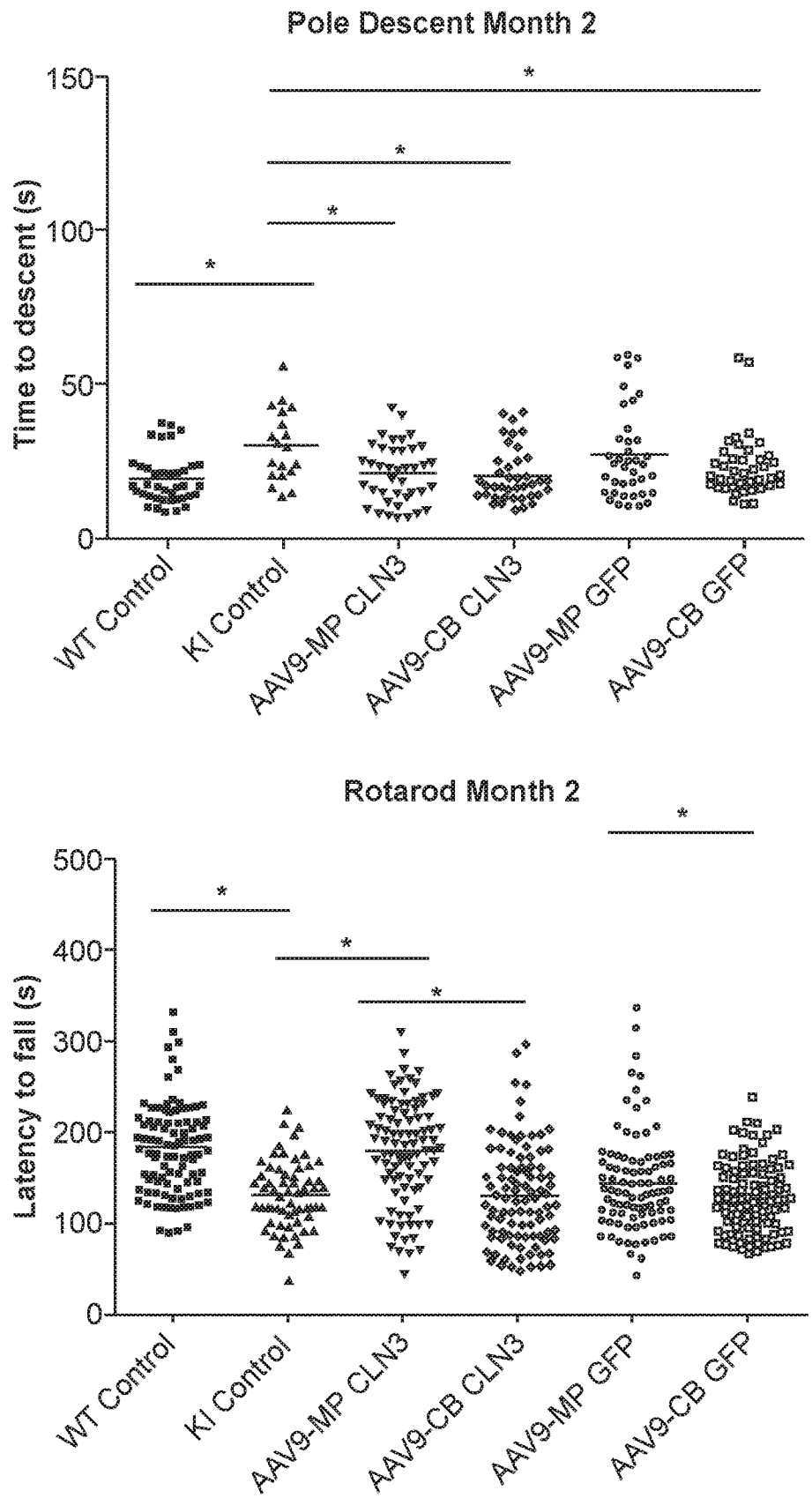
Figure 2C:
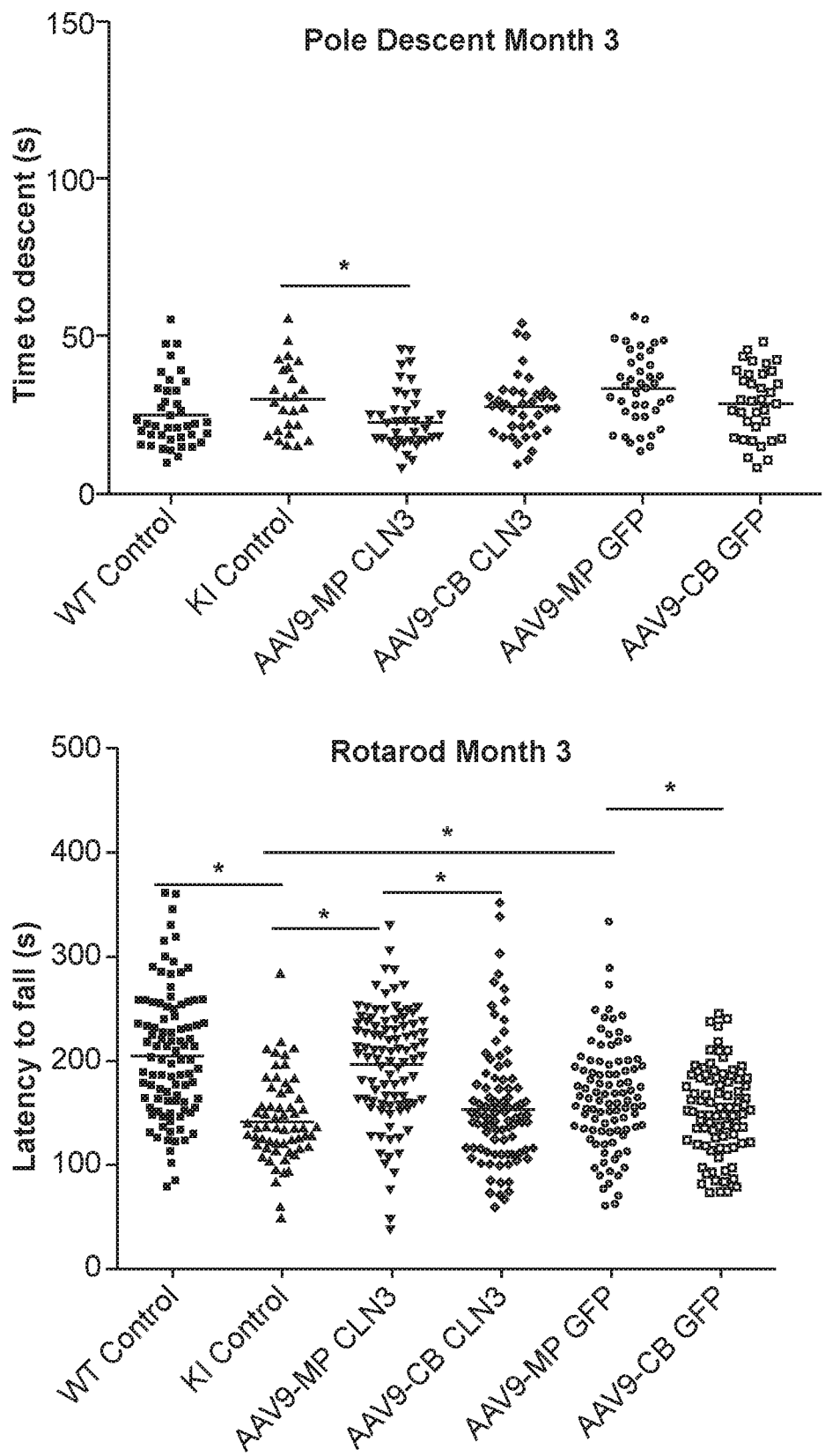
Figure 2D:
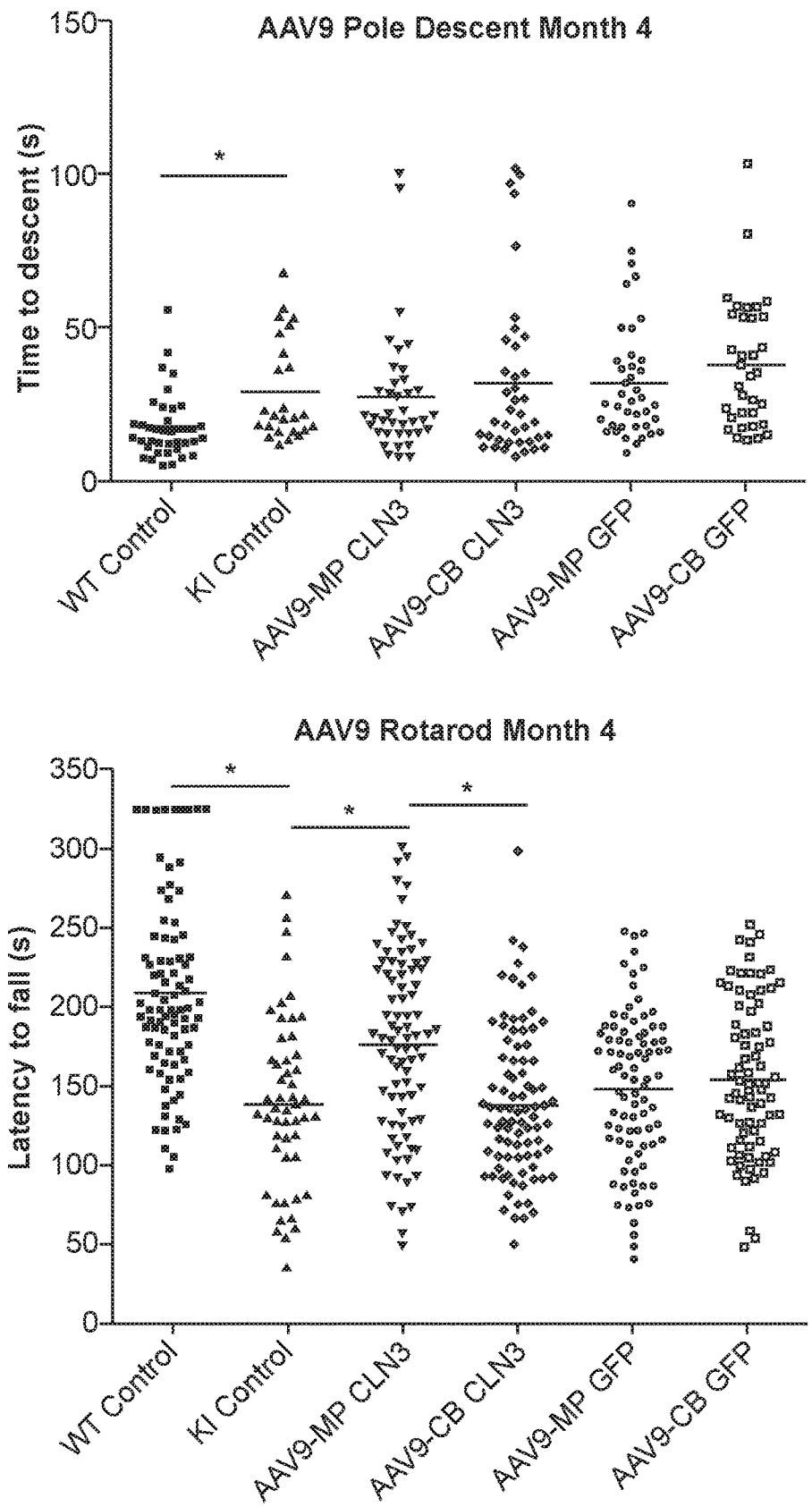
Figure 2E:
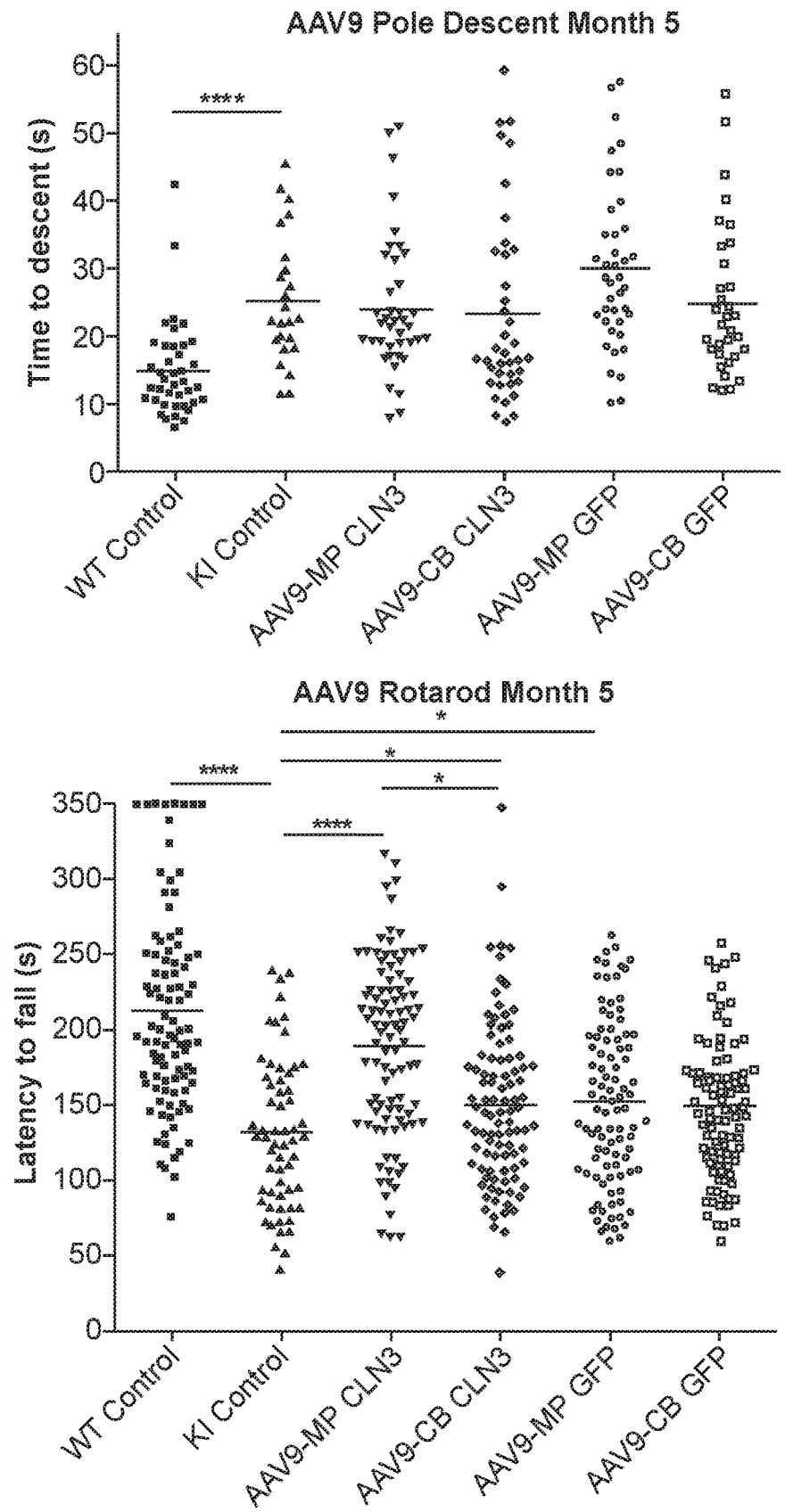
Figure 2F:
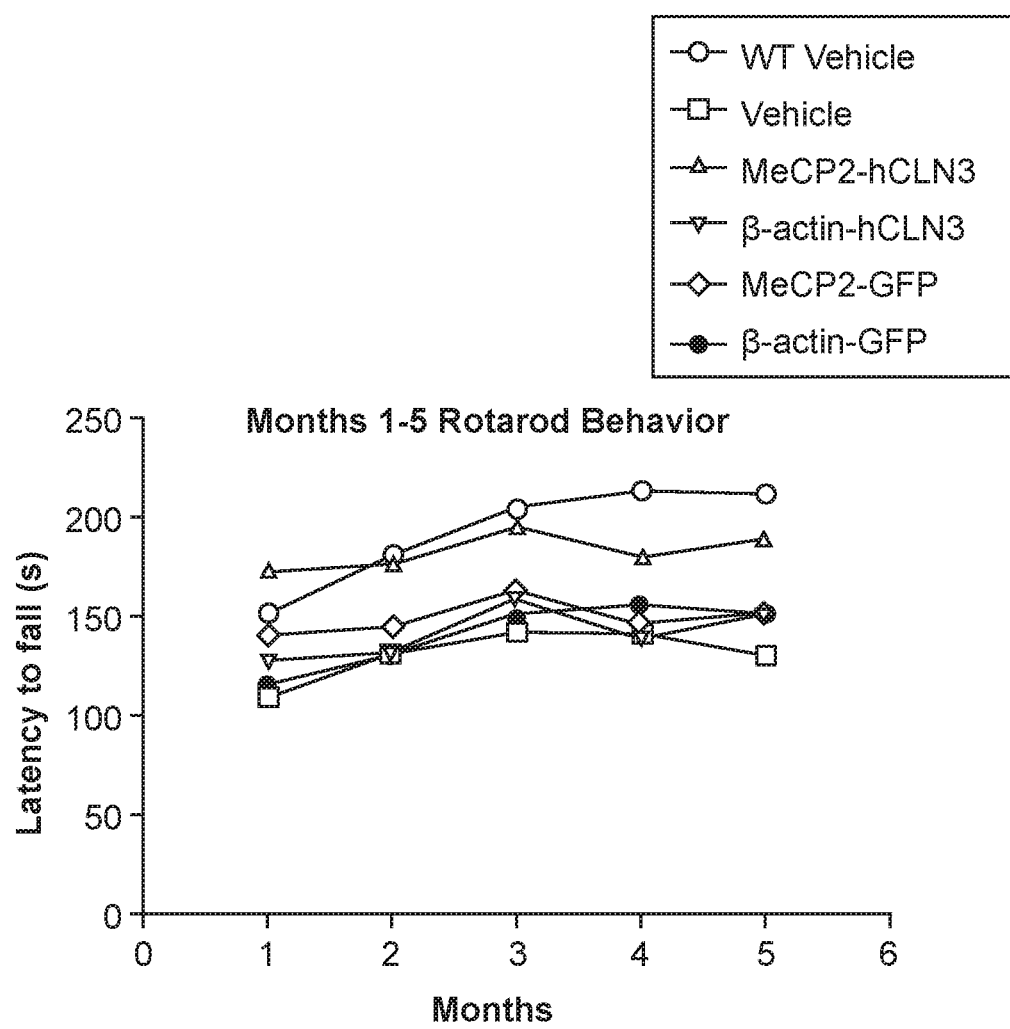
Figure 3:
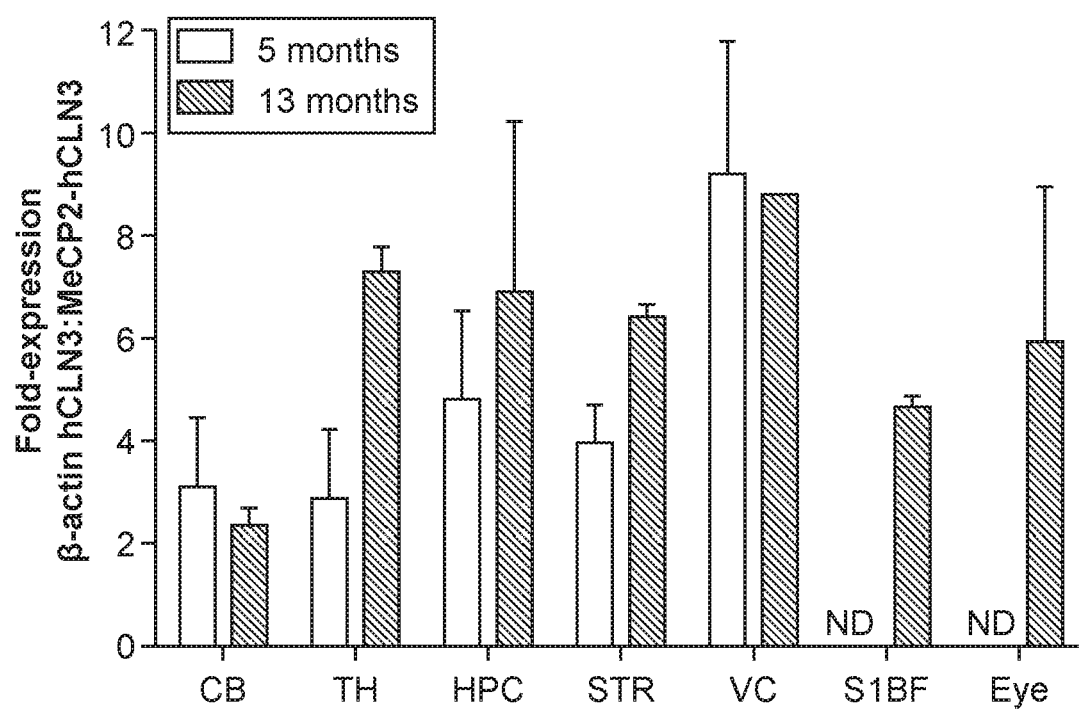
FIG. 3 illustrates dose-dependent hCLN3 expression in the brain following scAAV9 transduction. One month-old CLN3$^{\Delta ex7/8}$ mice (4/group) received one i.v. injection of 2×10$^{12}$ vg scAAV9/ β-actin-hCLN3 or scAAV9/MeCP2-hCLN3, whereupon hCLN3 mRNA expression was quantitated 5 months later in the indicated brain regions (CB, cerebellum; TH, thalamus; HPC, hippocampus; STR, striatum; and VC, visual cortex) by qRT-PCR. Results are expressed as the fold-increase in hCLN3 expression in mice receiving scAAV9/ β-actin-hCLN3 compared to scAAV9/MeCP2-hCLN3.
Figure 4:
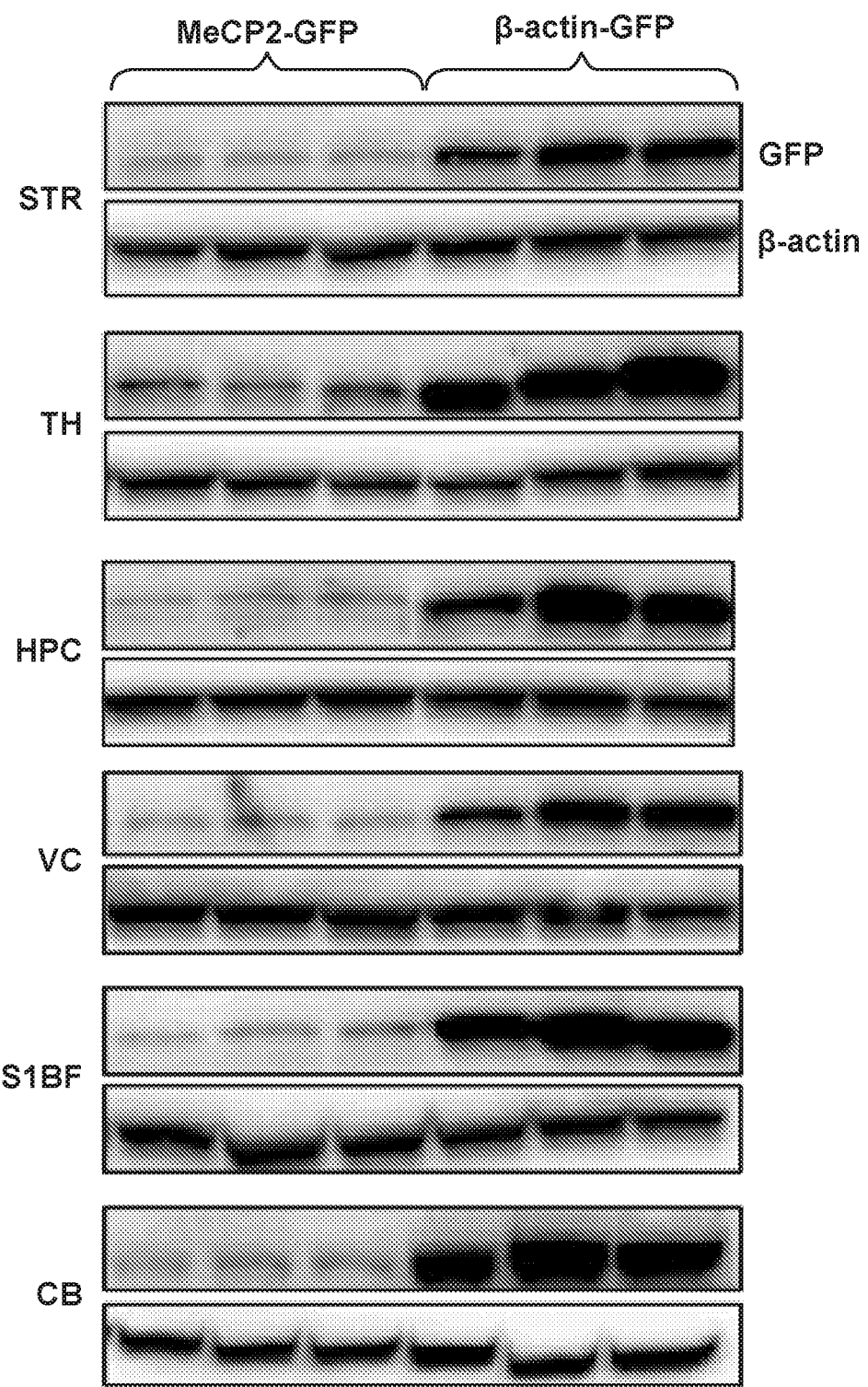
FIG. 4 illustrates dose-dependent GFP expression in the brain following scAAV9 transduction. One month-old CLN3$^{\Delta ex7/8}$ mice (3/group) received one i.v. injection of 2×10$^{12}$ vg scAAV9/ β-actin-GFP or scAAV9/MeCP2-GFP, whereupon GFP expression was quantitated 5 months later in the indicated brain regions (CB, cerebellum; TH, thalamus; HPC, hippocampus; STR, striatum; VC, visual cortex; S1BF, somatosensory barrel field cortex) by Western blot with β-actin as a loading control.

The feasibility of a gene therapy approach for JNCL is supported by data showing systemic i.v. delivery of scAAV9/MeCP2-hCLN3 (single dose) into one month-old CLN3$^{\Delta ex7/8}$ mice significantly improved motor behavior which was not observed with control viruses harboring GFP (FIG. 2A). Improved motor behavior continued to be observed at 2 months post-transduction (FIG. 2B), at 3 months post-transduction (FIG. 2C), at 4 months post-transduction (FIG. 2D), and at 5 months post-transduction (FIG. 2E). Analysis of blood chemistry profiles at 1 month and at 3 months revealed no abnormalities in any treatment group (data not shown).

scAAV9 constructs were engineered to achieve high versus low hCLN3 expression in transduced cells using the β-actin and MeCP2 promoters, respectively. 1 month old CLN3$^{\Delta ex7/8}$ mice were transduced with virus via the retroorbital sinus. Mice were sacrificed at 5 months and 13 months post-transduction, mice were 6 months and 14 months old, respectively. Brain regions were dissected from vibratome sections (300 μm thick). A promoter dosage effect was confirmed for both hCLN3, where expression was elevated from approximately 3- to 8-fold in the cerebellum (CB), thalamus (TH), hippocampus (HPC), striatum (STR), visual cortex (VC), somatosensory barrel field cortex (S1BF), and the eye of CLN3$^{\Delta ex7/8}$ mice treated with scAAV9/ β-actin-hCLN3 compared to the low expressing scAAV9/MeCP2-hCLN3 (FIG. 3), and GFP protein (FIG. 4).

Figure 5A:
FIGS. 5A-5B show biodistribution scAAV9/ β-actin-GFP or scAAV9/MeCP2-GFP as visualized by confocal microscopy in brain regions and retina 5 months and 13 months post-transduction, respectively.
Figure 5B:
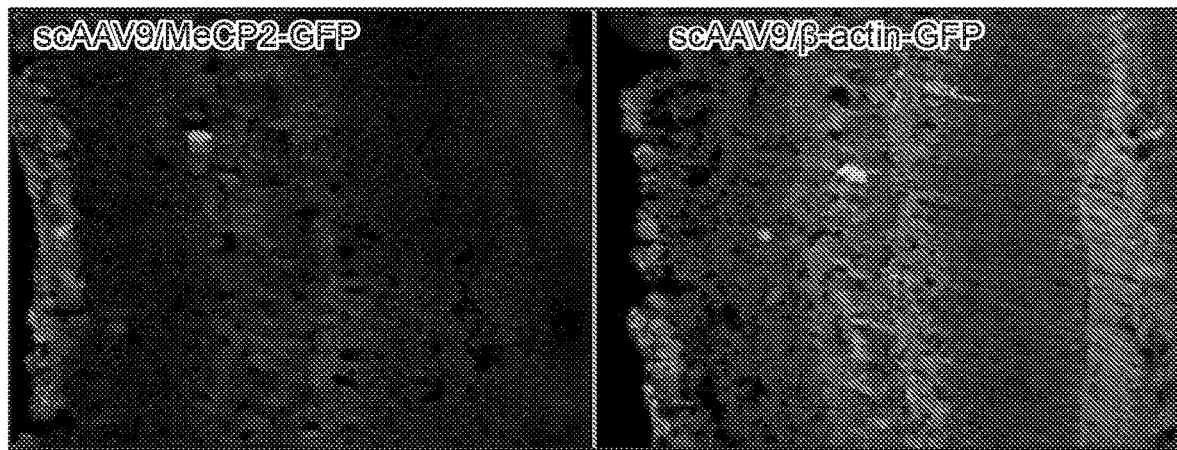

In addition, confocal images were acquired from brain cross sections collected from mice 5 months post-transduction to further visualize and confirm distribution and expression levels. Images were acquired using the same confocal settings to highlight expression differences. Results show wide biodistribution in both CLN3$^{\Delta ex7/8}$ mice treated with scAAV9/ β-actin-hCLN3 and scAAV9/MeCP2-hCLN3, with GFP intensity greater in the scAAV9/ β-actin-hCLN3 treated mice. FIG. 5A. Results also showed distribution of both scAAV9/ β-actin-hCLN3 and scAAV9/MeCP2-hCLN3 in retinal regions of mice 13 months following transduction. FIG. 5B.

Comparative biodistribution of scAAV9/ β-actin-GFP or scAAV9/MeCP2-GFP in the brains of CLN3$^{\Delta ex7/8}$ mice 5 months after administration of scAAV9/ β-actin-hCLN3 and scAAV9/MeCP2-hCLN3 was determined by counting GFP$^+$ cells and total cell number (DAPI$^+$). FIG. 6A. As summarized in FIG. 6B, scAAV9/MeCP2-hCLN3 treated mice displayed a significant increase in the percentage of GFP$^+$ cells in the S1BF, VPM/VPL, and VC regions of the brain.

The surprising finding of promoter dosage effect was further substantiated by similarities in the percentages of NeuN$^+$ and GFAP$^+$ cells transduced by both promoter constructs (data not shown). Importantly, the data show that CLN3$^{\Delta ex7/8}$ mice receiving a single injection of the low expressing construct (scAAV9/MeCP2-hCLN3) displayed consistent improvements in motor coordination out to five months post-transduction (latest interval examined to date) whereas the high expressing construct (scAAV9/ β-actin-hCLN3) was not effective (FIGS. 2A-2E).

Figure 8A:
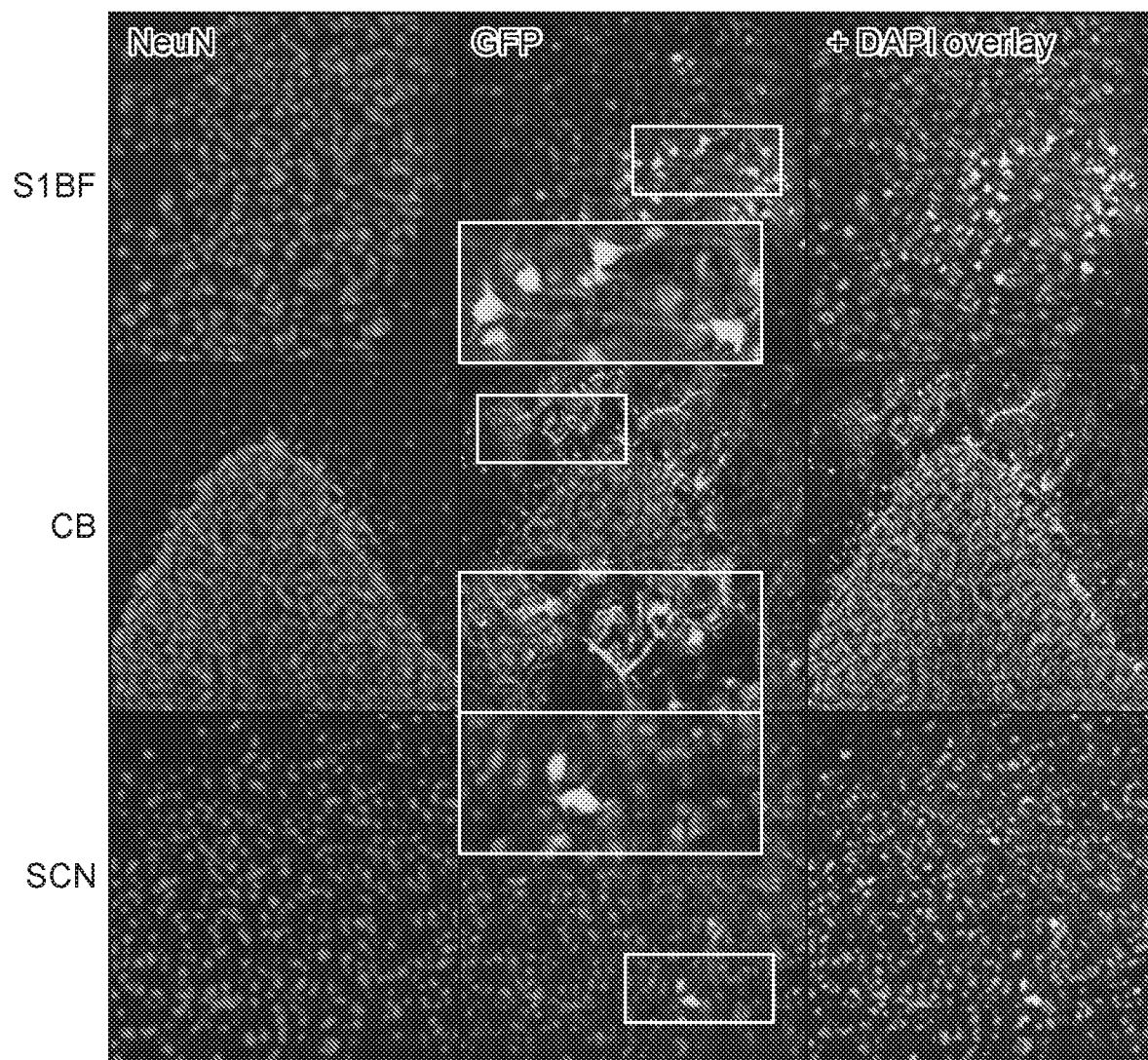
FIGS. 8A-8C shows the effect of systemic administration of scAAV9 on transduction of brain tissue.
Figure 8B:
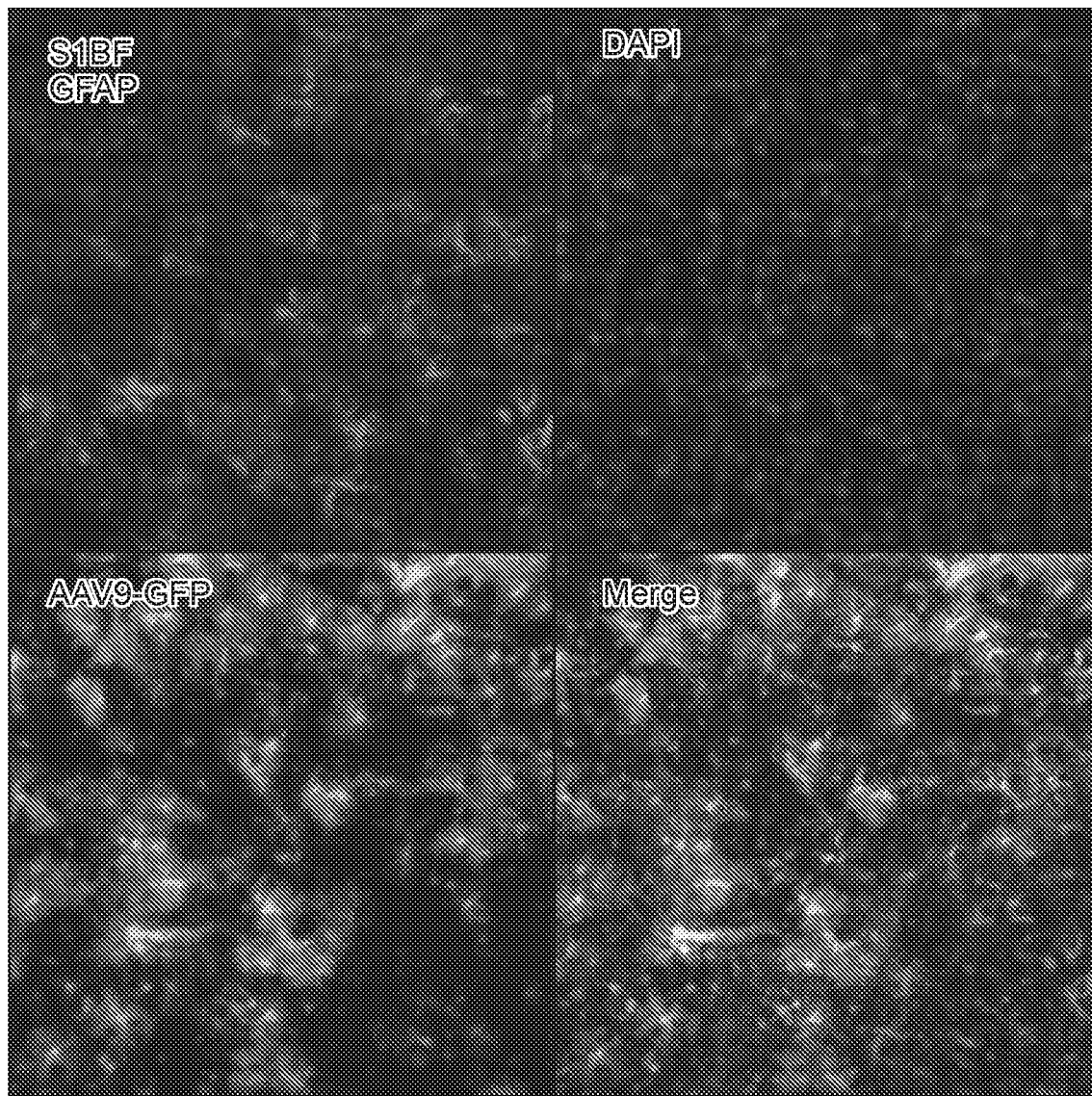
Figure 8C:
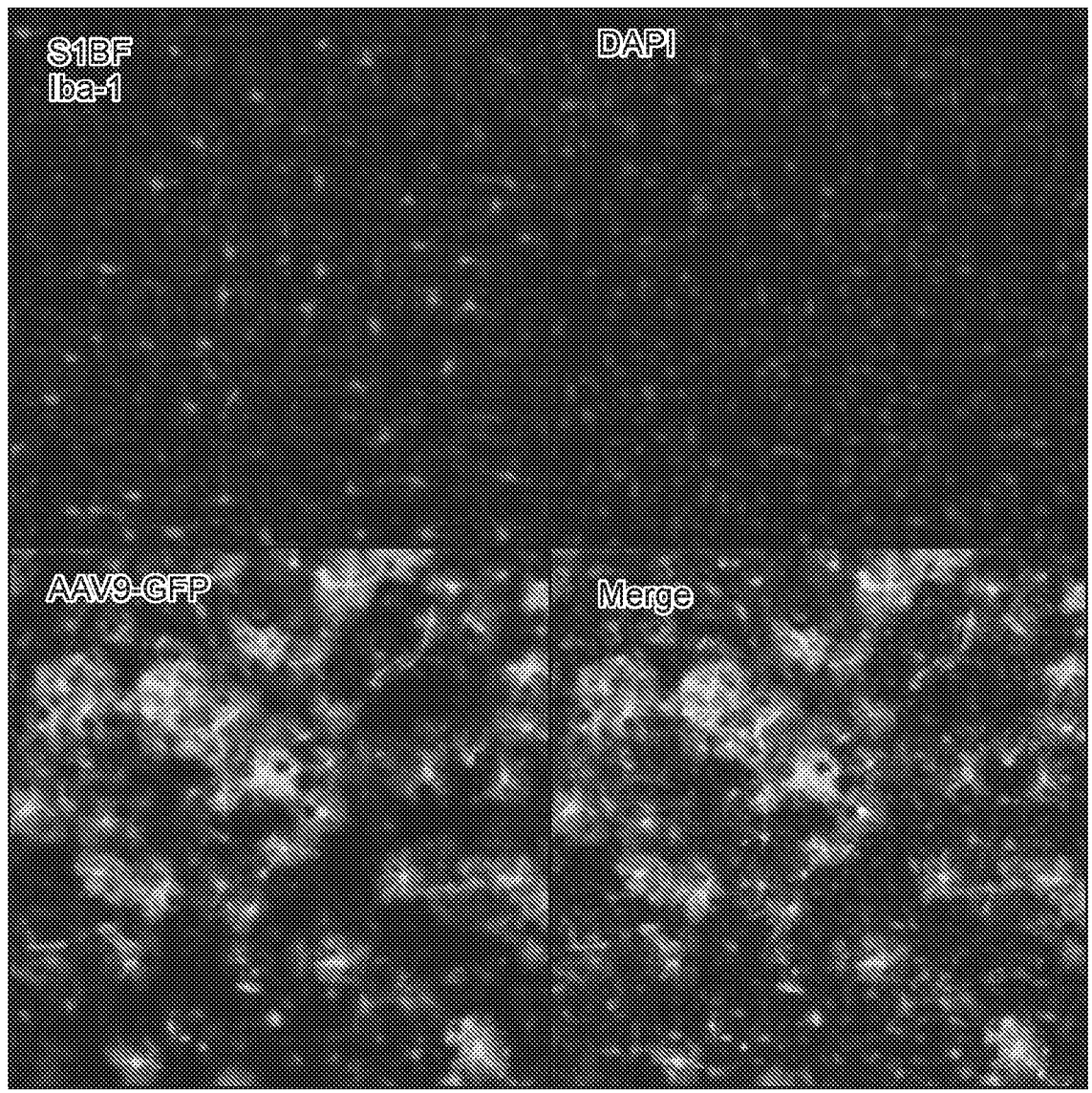
Figure 9:
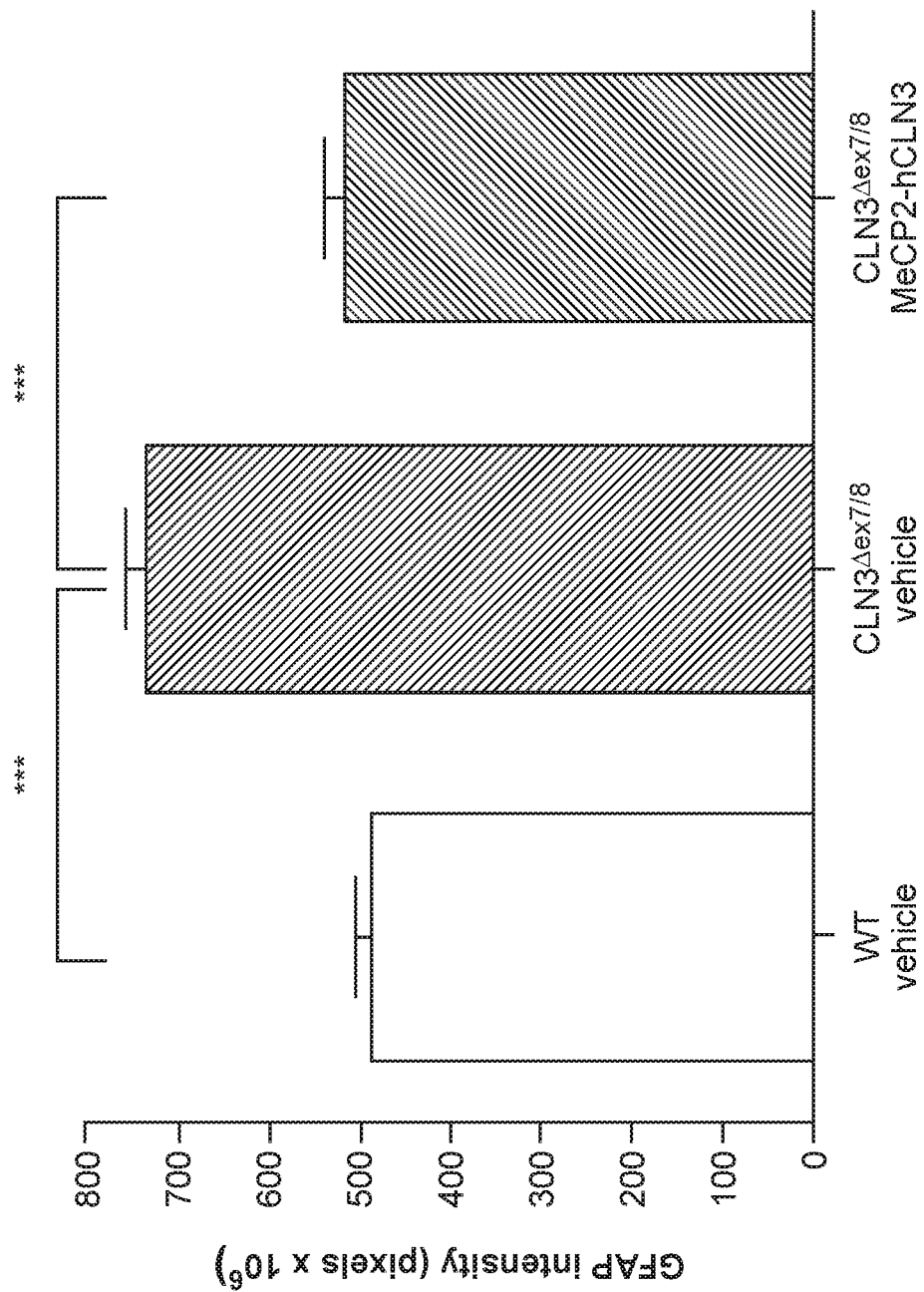
FIG. 9 shows that GFAP$^+$ reactive astrocytes, a hallmark of human Juvenile Batten Disease and also observed in the CLN3$^{\Delta ex7/8}$ brain, are significantly reduced in mice following the systemic administration of scAAV9/MeCP2-hCLN3. One month-old CLN3$^{\Delta ex7/8}$ mice (4/group) received one i.v. injection of scAAV9/MeCP2-hCLN3, whereupon reactive astrocytes (GFAP$^+$) were quantitated 5 months later in the somatosensory barrel field cortex by quantitative confocal microscopy. ***, p<0.001.
Figure 10:
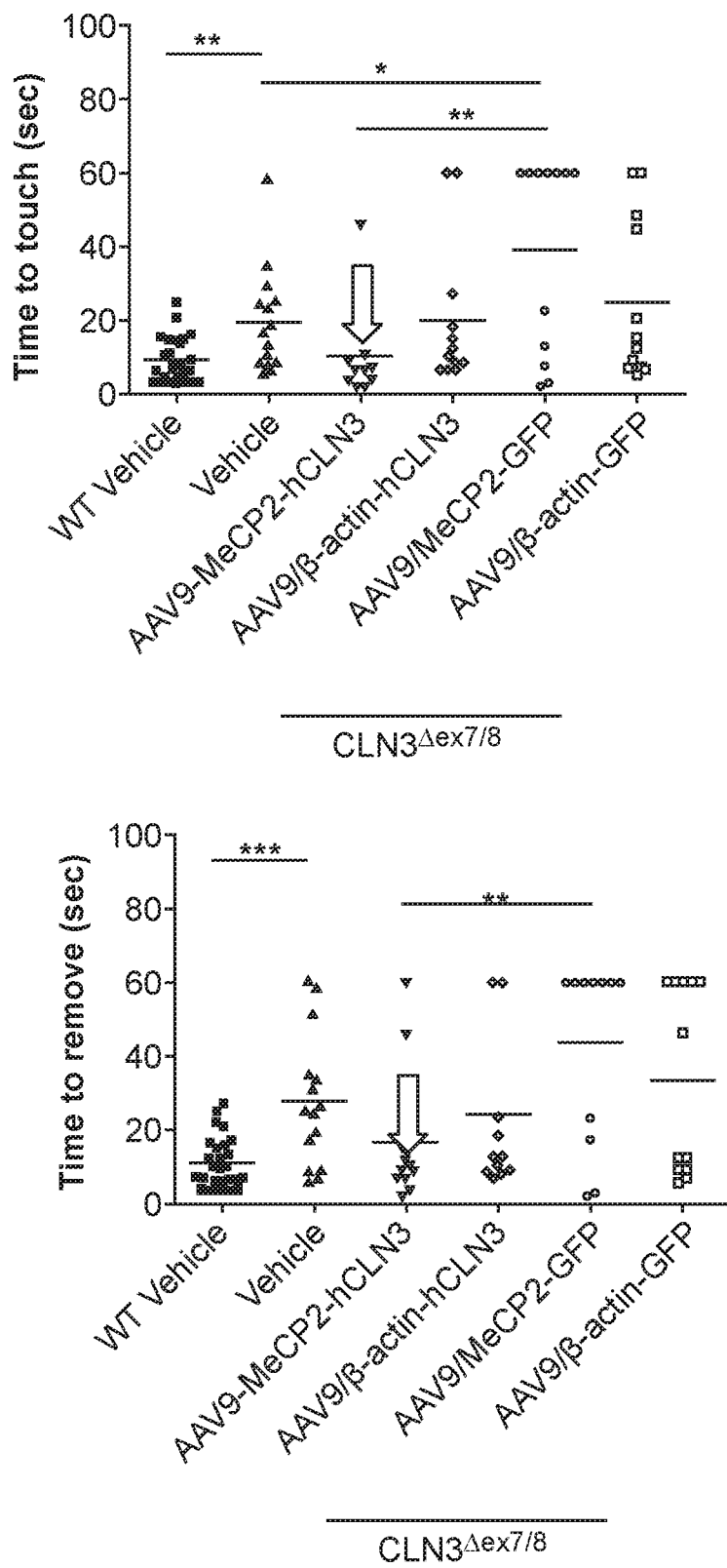
FIG. 10 show that CLN3 replacement using scAAV9/MeCP2-hCLN3 improves motor behaviors in CLN3$^{\Delta ex7/8}$ mice. One month-old CLN3$^{\Delta ex7/8}$ mice (8/group) received one i.v. injection of 2×10$^{12}$ vg of scAAV9/MeCP2-hCLN3, scAAV9/ β-actin-hCLN3, or GFP expressing viruses as controls, whereupon adhesive tape removal tests were performed at 11 months post-transduction showing reduced time to touch (left panel) and reduced time to remove (right panel) in CLN3$^{\Delta ex7/8}$ mice receiving scAAV9/MeCP2-hCLN3.

In addition, significant reductions in lysosomal storage material were observed in the brains of CLN3$^{\Delta ex7/8}$ mice receiving scAAV9/MeCP2-hCLN3 (FIGS. 7A-7G). The biodistribution of scAAV9 was widespread, with NeuN$^+$ neurons and GFAP$^+$ astrocytes transduced in the S1BF, VC, HPC, STR, TH, CB, and suprachiasmatic nucleus (SCN; FIG. 8A and data not shown), in agreement with other reports using scAAV9 in models of Rett syndrome and spinal muscular atrophy (SMA) (Garg et al. (2013) *J. Neurosci.* 33(34): 13612-13620; Foust et al. (2010) *Nat. Biotechnol.* 28(3): 271-274). As shown in FIG. 8B systemic administration of scAAV9 transduces astrocytes in the CLN3$^{\Delta ex7/8}$ brain. FIG. 8C shows that systemic administration of scAAV9 does not transduce microglia in the CLN3$^{\Delta ex7/8}$ brain.

Although, it appears that only a fraction of CNS cells were transduced by the virus, the behavioral improvements in CLN3$^{\Delta ex7/8}$ animals suggest beneficial intrinsic effects of hCLN3 in neurons and perhaps non-cell autonomous contributions from hCLN3 transduced glia. The latter would be expected to promote neuron survival based on the well appreciated role of astrocytes in regulating glutamate levels and neuron activity at the tripartite synapse (Perea et al. (2009) *Trends Neurosci.* 32(8): 421-431).

Figure 11:
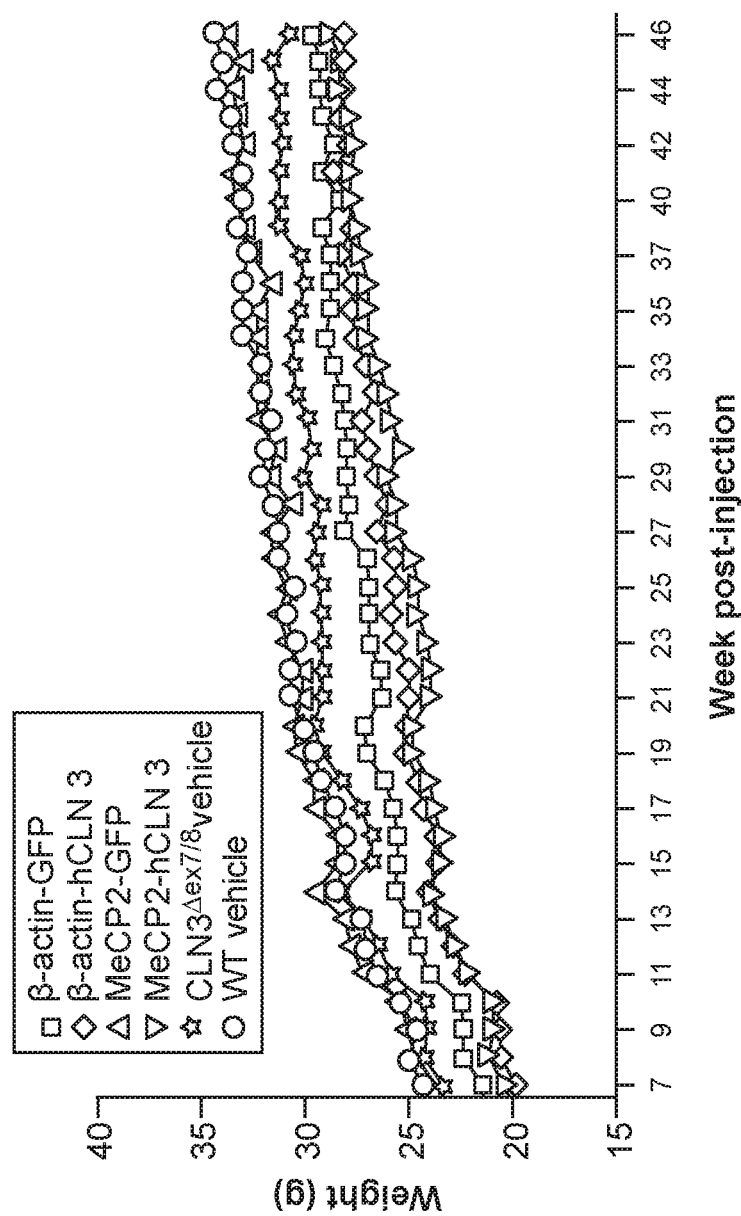
FIG. 11 illustrates effect of system AAV9 transgene delivery to CLN3$^{\Delta ex7/8}$ mice of AAV9/ β-actin-hCLN3, scAAV9/MeCP2-hCLN3, AAV9/ β-actin-GFP scAAV9/MeCP2-GFP. Results are expressed as weight in grams as determined weekly.

Another common symptom to JNCL is weight loss. The beneficial effects of scAAV9/MeCP2-hCLN3 on weight gain in CLN3$^{\Delta ex7/8}$ mice were not observed with the scAAV9/β-actin-hCLN3 or scAAV9/GFP control constructs confirming specificity of action for hCLN3 (FIG. 11).

It is noted that the approach described herein is advantageous over conventional therapies in that it can employ a systemic delivery route to enhance virus biodistribution and a unique promoter (MeCP2) to drive low CLN3 expression, since the preliminary data shows that high CLN3 levels are ineffective. In summary, several attributes of scAAV9/MeCP2-hCLN3 bolster the likelihood of success for improving JNCL outcome, namely; 1) this approach will correct the genetic defect at the root cause of the disease; 2) the virus can efficiently transduce CNS cells in juvenile and adult animals, which is critical because JNCL is not diagnosed until 5-10 years of age; 3) the MeCP2 promoter drives low level hCLN3 expression, which the data presented herein shows is essential for improving motor function in CLN3$^{\Delta ex7/8}$ mice; and 4) constructing the virus to harbor hCLN3 will accelerate its translation to clinical trials.

Example 2

Safety, Toxicity and Inflammation Assessment

Figure 12:
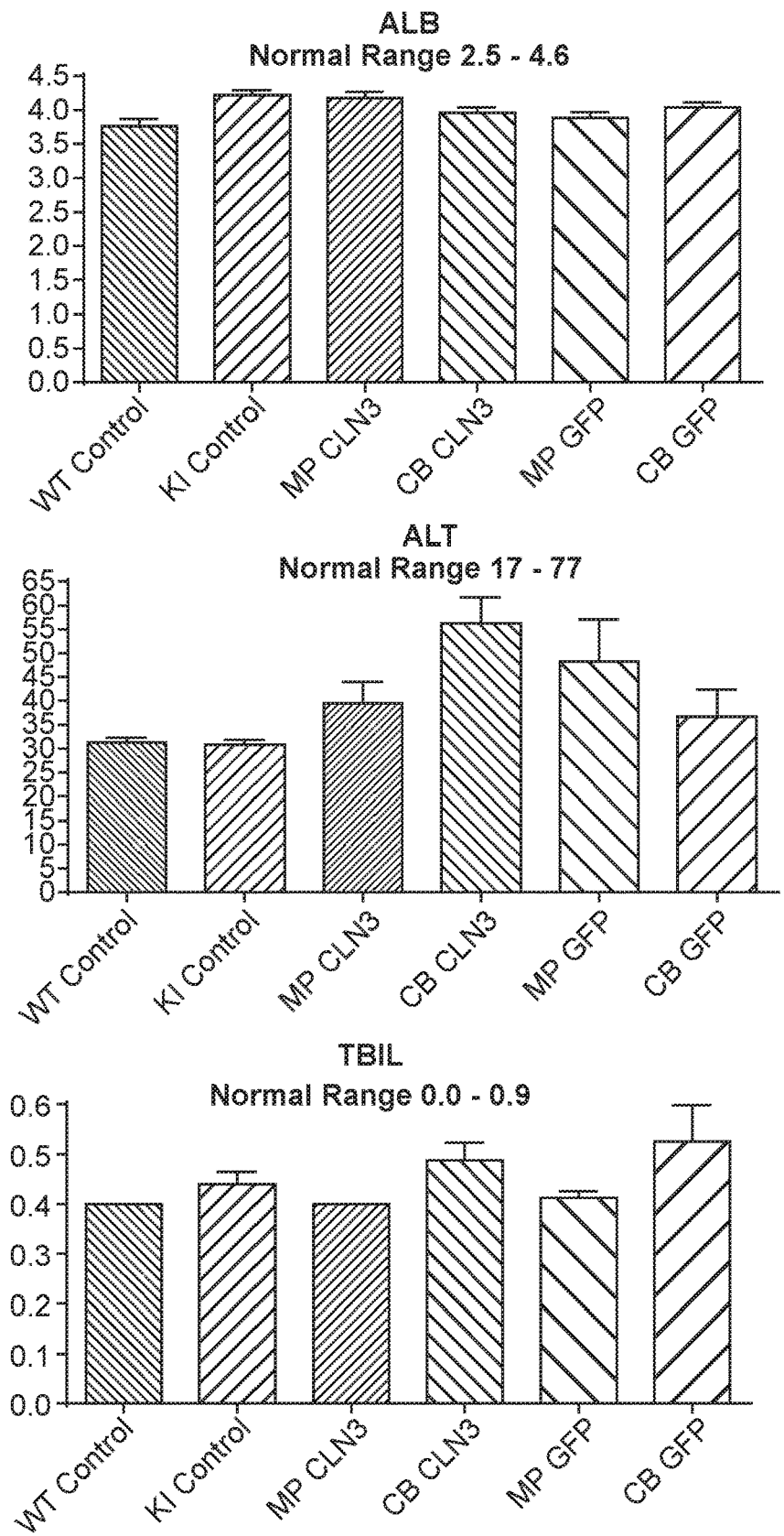
FIG. 12 demonstrates normal serum chemistry profiles for CLN3$^{\Delta ex7/8}$ mice administered AAV9/ β-actin-hCLN3, scAAV9/MeCP2-hCLN3, AAV9/ β-actin-GFP, or scAAV9/MeCP2-GFP 1-month post-infection.
Figure 12:
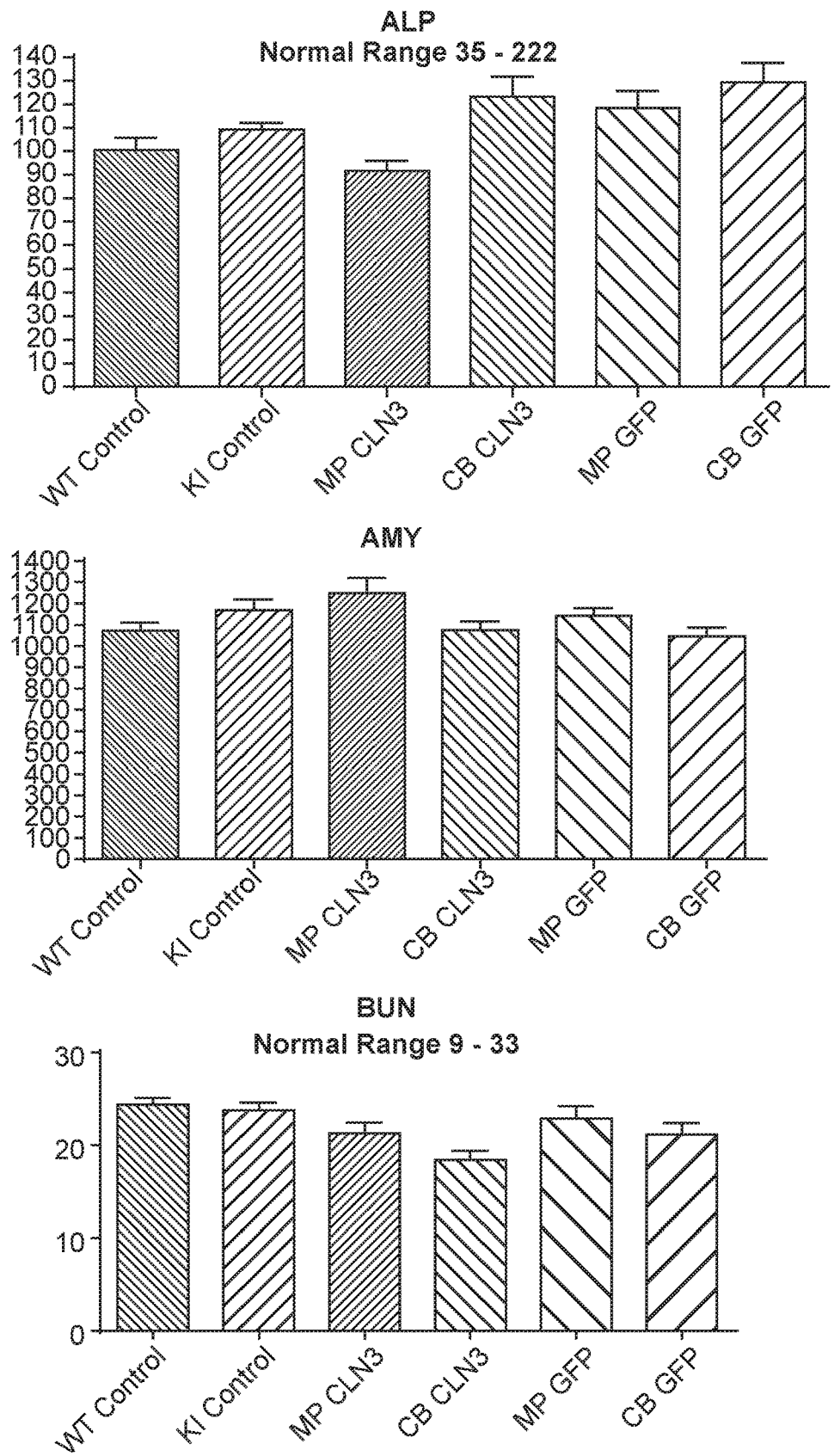
Figure 13:
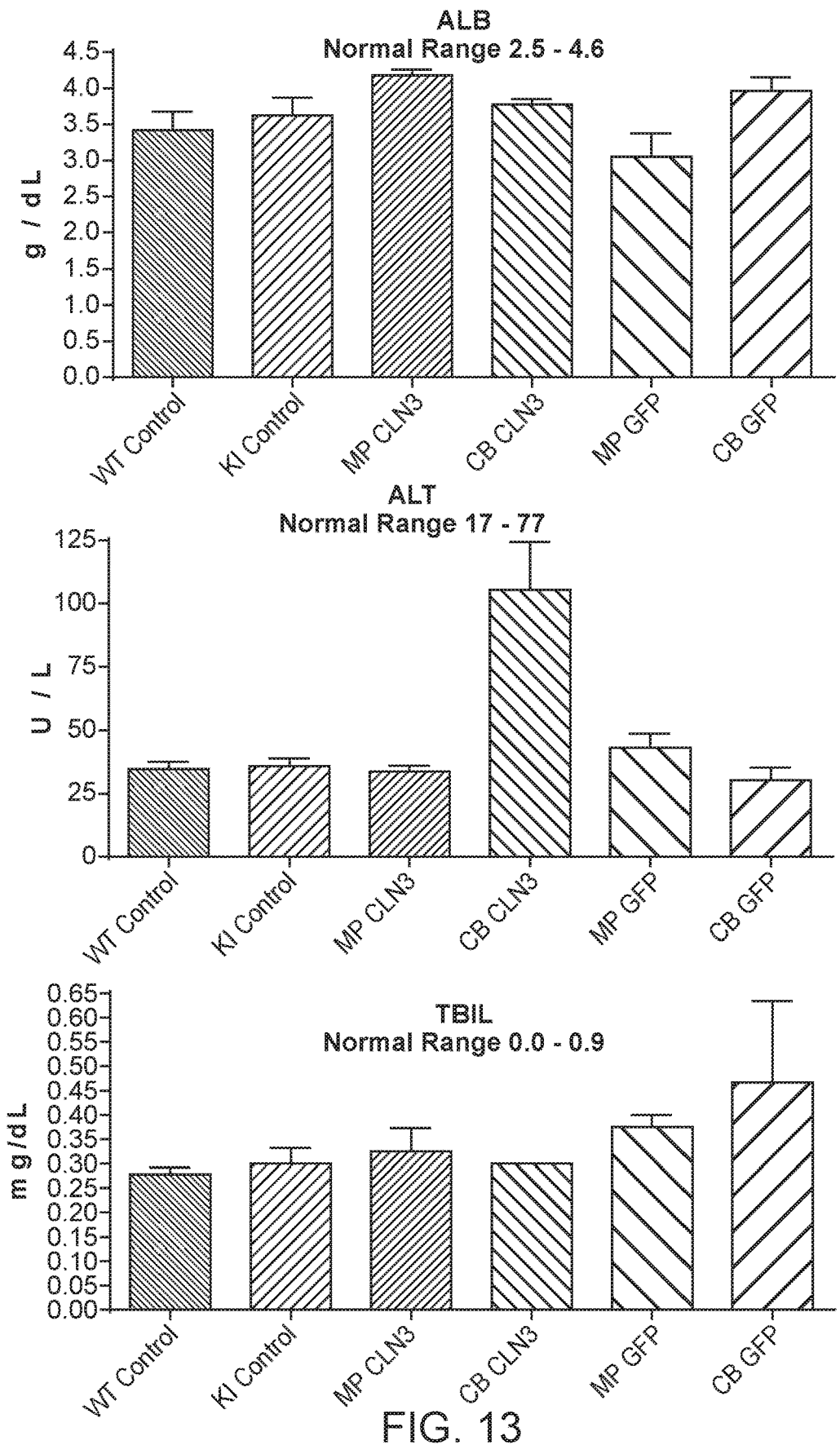
FIG. 13 demonstrates normal serum chemistry profiles for CLN3$^{\Delta ex7/8}$ mice administered AAV9/ β-actin-hCLN3, scAAV9/MeCP2-hCLN3, AAV9/ β-actin-GFP, or scAAV9/MeCP2-GFP 10-months post-infection.
Figure 13:
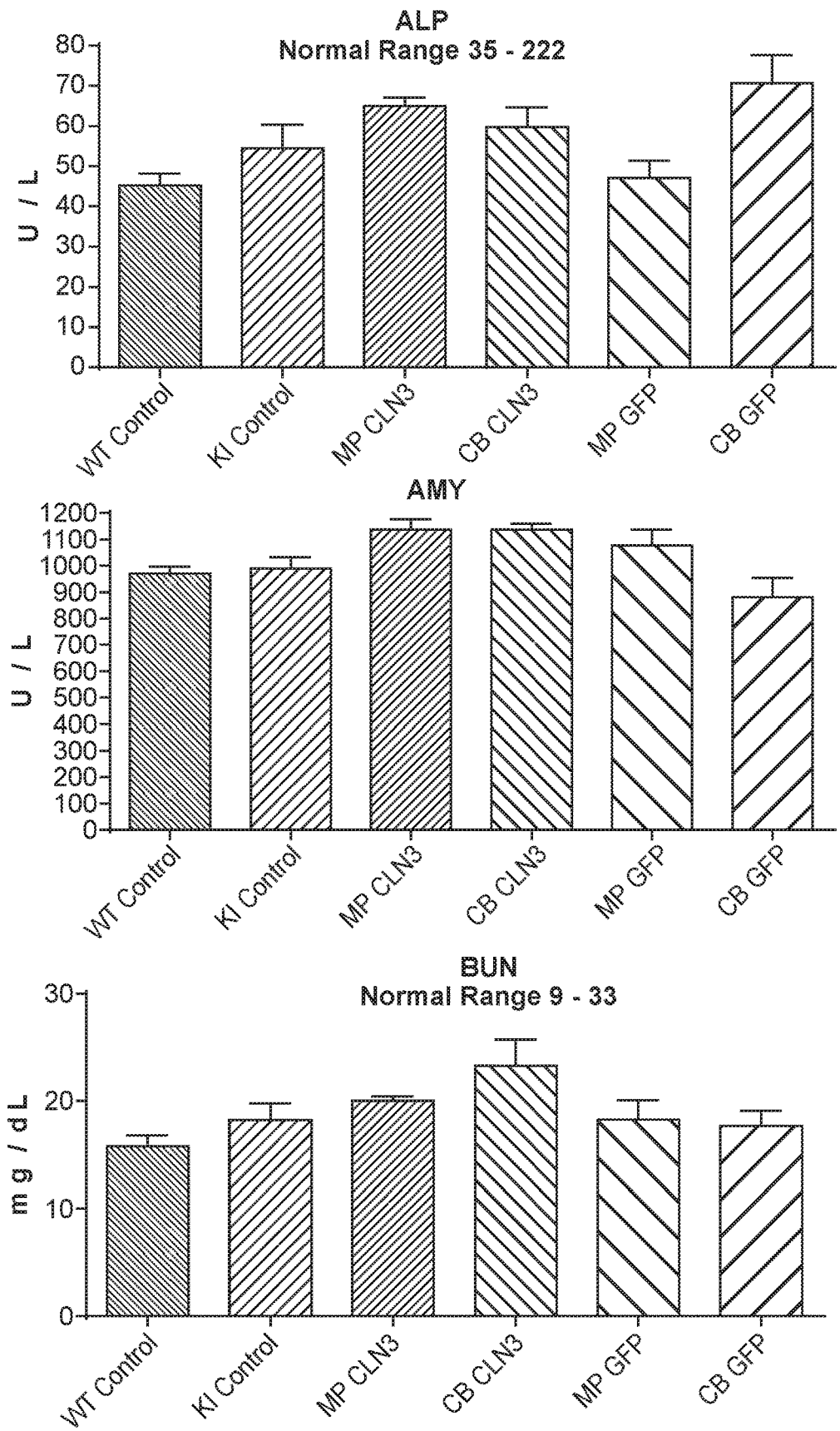
Figure 14:
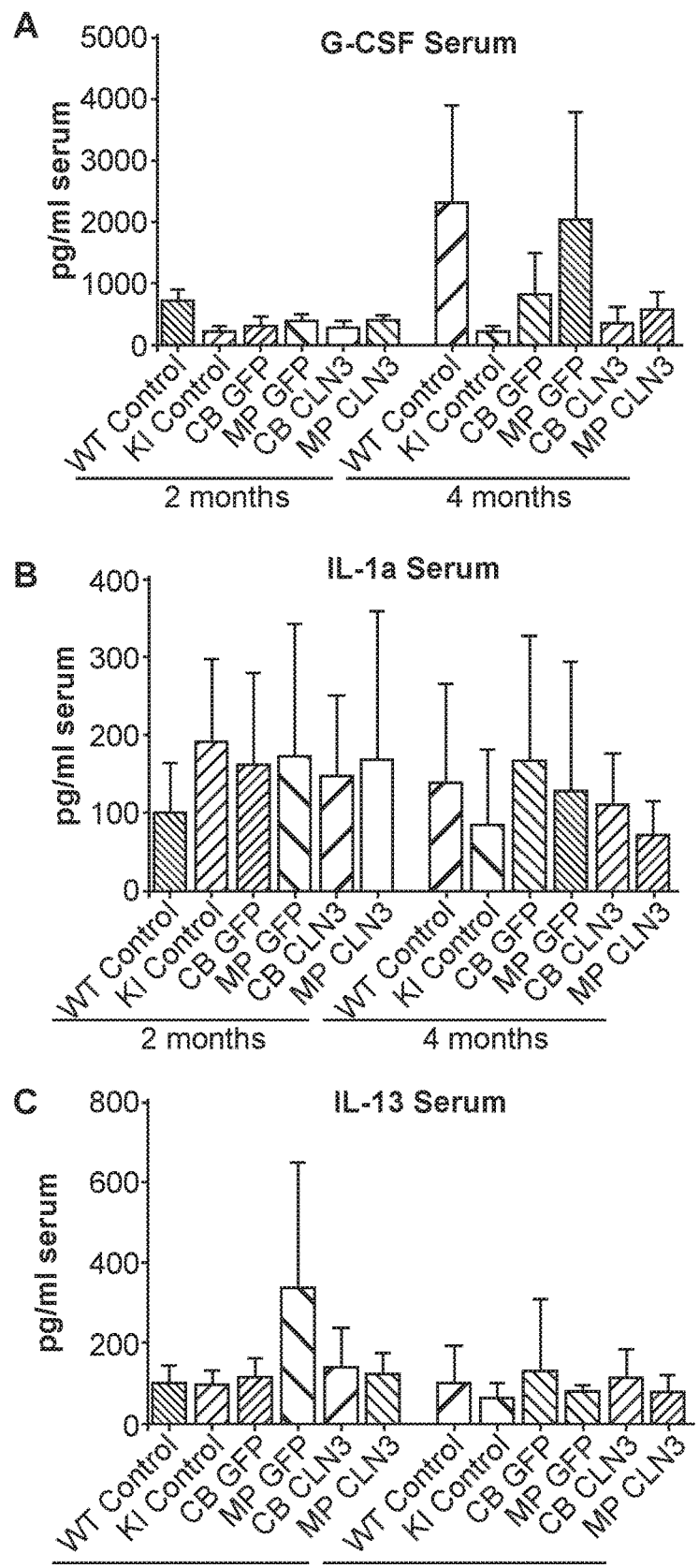
FIGS. 14A-F demonstrate CLN3$^{\Delta ex7/8}$ mice administered AAV9/ β-actin-hCLN3, scAAV9/MeCP2-hCLN3, AAV9/ β-actin-GFP, or scAAV9/MeCP2-GFP show no evidence of systemic inflammatory changes.
Figure 14:
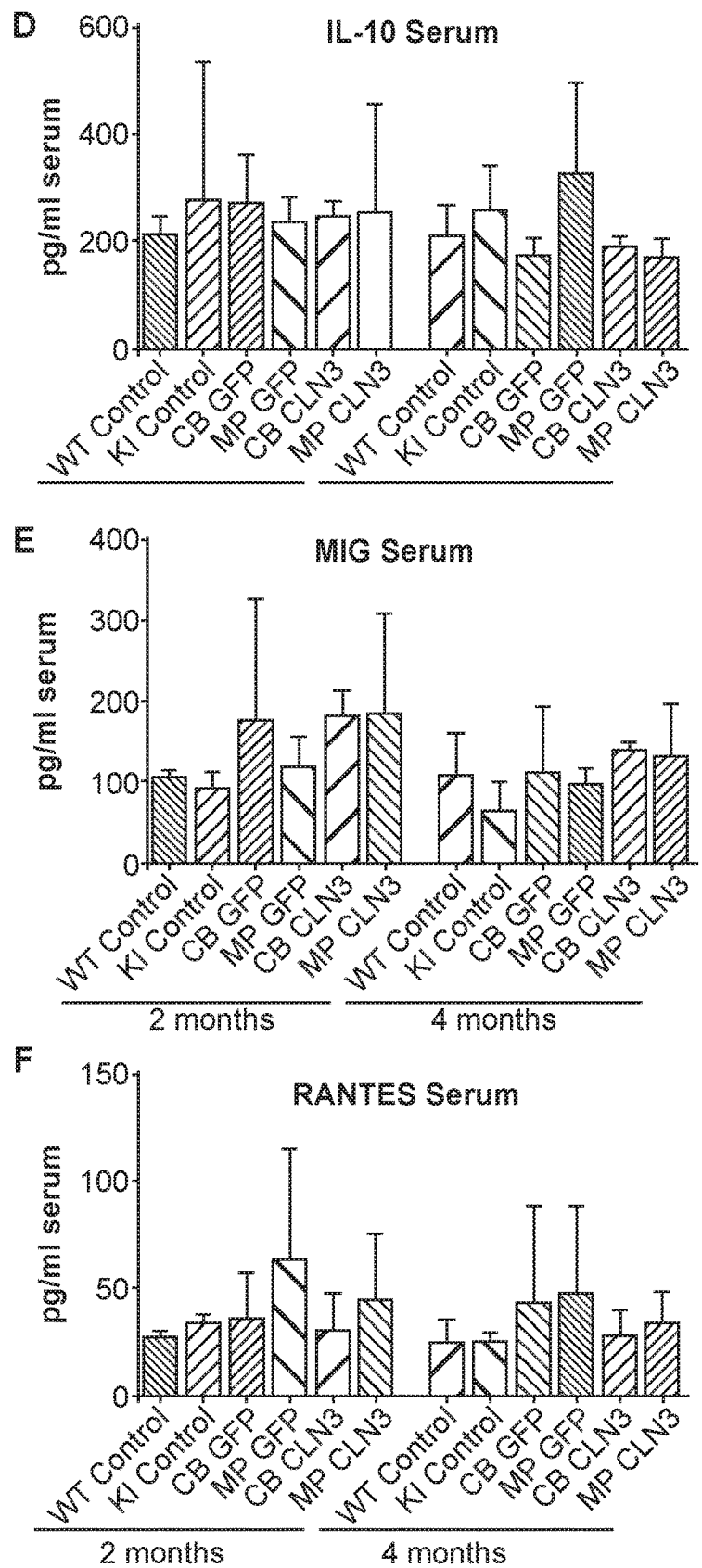

Serum chemistry panels (Abaxis, Union City, Calif., USA) were run on the different experimental mouse cohorts to assess safety and toxicity of the AAV treatments. Mediators measured included albumin (ALB), alkaline phosphatase (ALP), alanine aminotransferase (ALT), amylase (AMY), bilirubin (TBIL), blood urea nitrogen (BUN), calcium (CA), phosphorus (PHOS), glucose (GLU), sodium (Na$^+$), potassium (K$^+$), total protein (TP), globulin (GLOB), and creatinine (CRE). Virus was administered to one month old mice and testing was performed at 1-month (FIG. 12), 3-months (data not shown), 5-months (data not shown), 7-months (data not shown), and 10-months (FIG. 13) post-infection. Data revealed differences in certain analyte levels, for example, increased alanine aminotransferase levels in the mice receiving AAV9/ β-actin-hCLN3 as compared to the other experimental cohorts, but these were not statistically significant as to the normal ranges for each analyte.

Serum inflammatory mediator analyses were also performed using MILLIPLEX® panels (EMD Millipore, Billerica, Mass., USA). Mediators measured included granulocyte-colony stimulating factor (G-CSF), granulocyte-macrophage colony-stimulating factor (GM-CSF), interferon gamma (IFN-γ), interleukin-1 alpha (IL-1α), interleukin-1 beta (IL-1β), interleukin-2 (IL-2), interleukin-4 (IL-4), interleukin-5 (IL-5), interleukin-6 (IL-6), interleukin-7 (IL-7), interleukin-9 (IL-9), interleukin-10 (IL-10), interleukin-12p70 (IL-12p70), interleukin-13 (IL-13), interleukin-15 (IL-15), interleukin-17 (IL-17), chemokine (C—C) ligand 2 (CCL2), chemokine (C—C) ligand 3 (CCL3), chemokine (C—C) ligand 5 (CCL5/RANTES), chemokine (C—X—C) ligand 2 (CXCL2), chemokine (C—X—C) ligand 9 (CXCL9/MIG), chemokine (C—X—C) ligand 10 (CXCL10), tumor necrosis factor-alpha (TNF-α), and vascular endothelial growth factor (VEGF). Virus was administered to one month old mice. Samples were collected at 2- and 4-months post-transduction to assess whether AAV9 elicited evidence of systemic inflammation. Only those mediators that were detected are shown in FIGS. 14A-14F. Consistent with prior studies, there was little evidence of systemic inflammation in vehicle-treated CLN3$^{\Delta ex7/8}$ mice as these mice typically do not display overt systemic or CNS inflammation until approximately one year of age. In addition, the AAV9 viruses did not show evidence of systemic inflammatory changes. Together these data suggest the safety of AAV9 for treatment of JNCL.

Example 3

AAV Manufacture

AAV9 was produced by transient transfection procedures using a double-stranded AAV2-ITR-based CB-GFP vector, with a plasmid encoding Rep2Cap9 sequence along with an adenoviral helper plasmid pHelper (Stratagene) in 293 cells. The serotype 9 sequence was verified by sequencing and identical to that previously described (Gao et al. (2002) *Proc. Natl. Acad. Sci. USA,* 99: 11854-11859). Virus was purified by two cesium chloride density gradient purification steps, dialyzed against PBS and formulated with 0.001% Pluronic-F68 to prevent virus aggregation and stored at 4° C. All vector preparations were titered by quantitative PCR using Taq-Man technology.

The AAV construct contains two inverted terminal repeats flanking a gene expression cassette. A modification to the left inverted terminal repeat removed the site of Rep nicking thereby creating self-complementary AAV genomes. The expression cassette contains a fragment of the mouse MeCP2 promoter as previously described (Garg et al. (2013) *J. Neurosci.* 33: 13612-13620; Adachi et al. (2005) *Hum Mol Genet.* 14: 3709-3722) to drive transgene expression. The expression cassette contains an SV40 intron and the human CLN3 variant 2 cDNA (GenBank Accession No: NM_000086.2; SEQ ID NO: 11) followed by a bovine growth hormone polyadenylation sequence.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes, including sequence listings within.

What is claimed is:

1. A recombinant self-complementary adeno-associated virus serotype 9 (scAAV9) vector comprising a polynucleotide encoding human CLN3 operably linked to a methyl-CPG binding protein 2 (MeCP2) promoter.

2. The vector of claim 1, wherein the vector further comprises a 5'UTR/intron selected from SV40 or CBA-MVM and/or a minimal SV40 intron.

3. A method of transducing an isolated mammalian cell, the method comprising transducing the isolated mammalian cell with the vector of claim 2.

4. A pharmaceutical formulation comprising the recombinant self-complementary adeno-associated virus serotype 9 (AAV9) vector according to claim 2 and a pharmaceutically acceptable carrier or diluent.

5. The vector of claim 1, wherein the vector further comprises a polyadenylation signal selected from a bovine growth hormone polyadenylation sequence, a SV40 late polyadenylation sequence, a SV40 early polyadenylation sequence, an AATAAA (SEQ ID NO:3) polyadenylation signal, a CAATAAA (SEQ ID NO:4) polyadenylation signal, an ATTAAA (SEQ ID NO:5) polyadenylation signal, or a TANA (SEQ ID NO:6) polyadenylation signal.

6. A method of transducing an isolated mammalian cell, the method comprising transducing the isolated mammalian cell with the vector of claim 5.

7. A pharmaceutical formulation comprising the recombinant self-complementary adeno-associated virus serotype 9 (AAV9) vector according to claim 5 and a pharmaceutically acceptable carrier or diluent.

8. The vector of claim 1, wherein the vector further comprises a posttranslational regulatory element.

9. The vector of claim 8, wherein the posttranscriptional regulatory element is selected from the group of a Woodchuck Post-transcriptional Regulatory Element (WPRE), a WPRE2 containing a minimal gamma element and a partial alpha-beta element, a WPRE3 containing minimal gamma and alpha elements, or a hepatitis B virus posttranscriptional regulatory element (HPRE).

10. A method of transducing an isolated mammalian cell, the method comprising transducing the isolated mammalian cell with the vector of claim 9.

11. A pharmaceutical formulation comprising the recombinant self-complementary adeno-associated virus serotype 9 (AAV9) vector according to claim 9 and a pharmaceutically acceptable carrier or diluent.

12. A method of transducing an isolated mammalian cell, the method comprising transducing the isolated mammalian cell with the vector of claim 8.

13. A pharmaceutical formulation comprising the recombinant self-complementary adeno-associated virus serotype 9 (AAV9) vector according to claim 8 and a pharmaceutically acceptable carrier or diluent.

14. An isolated mammalian cell transduced with the vector according to claim 1.

15. A method of transducing an isolated mammalian cell, the method comprising transducing the isolated mammalian cell with the vector of claim 1.

16. The method of claim 15, wherein the isolated mammalian cell is a cell of the central nervous system.

17. A pharmaceutical formulation comprising the vector of claim 1 and a pharmaceutically acceptable carrier or diluent.

18. A method for treating Juvenile neuronal ceroid lipofuscinosis (JNCL) in a mammal, the method comprising administering a vector of claim 1 intravenously into a mammal diagnosed with JNCL.

19. The method of claim 18, wherein the mammal is homozygous for a CLN3 mutation.

20. The method of claim 18, wherein the mammal has at least one symptom of JNCL selected from the group consisting of blindness, seizures, motor loss, and cognitive decline.

21. The method of claim 18, wherein the vector is administered intravenously in a single administration.

22. The method of claim 18, wherein the vector is administered at least 2, 3, 4, 5, 6, 7, 8, 9, or 10 times.

23. The vector of claim 18, wherein about $10^{10}$ up to about $10^{16}$ copies of the scAAV9 are administered per kg of body weight of the mammal.

24. A method for treating Juvenile neuronal ceroid lipofuscinosis (JNCL) in a mammal, the method comprising administering a vector of claim 1 intravenously into a mammal presenting with at least one symptom selected from the group consisting of blindness, seizures, motor loss, and cognitive decline, wherein the genome of the mammal comprises a homozygous CLN3 mutation.

25. The method of claim 24, wherein the vector is administered intravenously in a single administration.

26. The method of claim 24, wherein the vector is administered at least 2, 3, 4, 5, 6, 7, 8, 9, or 10 times.

27. The method of claim 24, wherein about $10^{10}$ up to about $10^{16}$ copies of the polynucleotide encoding CLN3 are administered.

* * * * *